US011155885B2

(12) United States Patent
Li

(10) Patent No.: US 11,155,885 B2
(45) Date of Patent: Oct. 26, 2021

(54) REAL-TIME REVERSE TRANSCRIPTASE-POLYMERASE CHAIN REACTION ASSAY WITH MODIFIED PROBE FOR THE DIAGNOSIS OF RABIES VIRUSES AND OTHER LYSSAVIRUSES

(71) Applicant: The U.S.A., as represented by the Secretary, Department of Health and Human Services, Bethesda, MD (US)

(72) Inventor: Yu Li, Johns Creek, GA (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 249 days.

(21) Appl. No.: 16/303,006

(22) PCT Filed: May 8, 2017

(86) PCT No.: PCT/US2017/031595
§ 371 (c)(1),
(2) Date: Nov. 19, 2018

(87) PCT Pub. No.: WO2017/200790
PCT Pub. Date: Nov. 23, 2017

(65) Prior Publication Data
US 2019/0284646 A1 Sep. 19, 2019

Related U.S. Application Data

(60) Provisional application No. 62/339,323, filed on May 20, 2016.

(51) Int. Cl.
*C12Q 1/70* (2006.01)
*C12Q 1/6876* (2018.01)

(52) U.S. Cl.
CPC .............. *C12Q 1/70* (2013.01); *C12Q 1/6876* (2013.01); *C12Q 1/701* (2013.01); *C12Q 2600/16* (2013.01)

(58) Field of Classification Search
CPC ........ C12Q 1/70; C12Q 1/701; C12Q 1/6876; C12Q 2600/16
See application file for complete search history.

(56) References Cited

U.S. PATENT DOCUMENTS

| 7,544,791 | B2 | 6/2009 | Fu |
| 2004/0208900 | A1 | 10/2004 | Fu |
| 2011/0256174 | A1 | 10/2011 | Fu |

FOREIGN PATENT DOCUMENTS

| CN | 101113479 | 1/2008 |
| EP | 0237686 | 9/1987 |
| WO | WO 2006/116458 | 11/2006 |

OTHER PUBLICATIONS

Demas et al., PLOS one, vol. 3, Issue 4, e2057, pp. 1-6, Apr. 2008.*
Bourhyet al., Virology, 194(1)L 70-81, May 1993.*
Afonina et al., "Efficient Priming of PCR with Short Oligonucleotides Conjugated to a Minor Groove Binder," *Nucl. Acids Res.*, vol. 25:2657-2660, 1997.
Black et al., "A Rapid RT-PCR Method to Differentiate Six Established Genotypes of Rabies and Rabies-Related Viruses using TaqMan™ Technology," *J. Virol. Methods*, vol. 105:25-35, 2002.
Coertse et al., "Improved PCR Methods for Detection of African Rabies and Rabies-Related Lyssaviruses," *J. Clin. Microbiol.*, vol. 48:3949-3955, 2010.
Deubelbeiss et al., "Real-Time RT-PCR for the Detection of Lyssavirus Species," *J. Vet. Med.*, vol. 2014, 12 pp.
Dupuis et al., "Comparison of Automated Quantitative Reverse Transcription-PCR and Direct Fluorescent-Antibody Detection for Routine Rabies Diagnosis in the United States," *J. Clin. Microbiol.*, vol. 53:2983-2989, 2015.
Eurogentec, qPCR Guide, downloaded from https://secure.eurogentec.com/uploads/qPCR-guide.pdf, 68 pp., Jun. 14, 2017.
Fischer et al., "Molecular Double-Check Strategy for the Identification and Characterization of European Lyssaviruses," *J. Virol. Methods*, vol. 203:23-32, 2014.
Fischer et al., "Perspectives on Molecular Detection Methods of Lyssaviruses," *Berl. Münch. Tierärztl. Wochenschr.*, vol. 125:264-271, 2012.
Fooks et al., Emerging Technologies for the Detection of Rabies Virus: Challenges and Hopes in the 21$^{st}$ Century, *PLoS Negl. Trop. Dis.*, vol. 3:e530, 2009.
Hayman et al., "A Universal Real-Time Assay for the Detection of Lyssaviruses," *J. Virol. Methods*, vol. 177:87-93, 2011.
Heaton et al., "Heminested PCR Assay for Detection of Six Genotypes of Rabies and Rabies-Related Viruses," *J. Clin. Microbiol.*, vol. 35:2762-2766, 1997.
Hoffmann et al., "Improved Safety for Molecular Diagnosis of Classical Rabies Viruses by Use of a TaqMan Real-Time Reverse Transcription-PCR "Double Check" Strategy," *J. Clin. Microbiol.*, vol. 48:3970-3978, 2010.
Kutyavin et al., "3'-Minor Groove Binder-DNA Probes Increase Sequence Specificity at PCR Extension Temperatures," *Nucl. Acids Res.*, vol. 28:655-661, 2000.
Lembo et al., "Evaluation of a Direct, Rapid Immunohistochemical Test for Rabies Diagnosis," *Emerg. Infect. Dis.*, vol. 12:310-313, 2006.
Nadin-Davis et al., "Development of Real-Time Reverse Transcriptase Polymerase Chain Reaction Methods for Human Rabies Diagnosis," *J. Med. Virol.*, vol. 81:1484-1497, 2009.

(Continued)

*Primary Examiner* — Cynthia B Wilder
(74) *Attorney, Agent, or Firm* — Klarquist Sparkman, LLP

(57) ABSTRACT

A real-time reverse transcriptase-polymerase chain reaction (RT-PCR) assay that utilizes multiplex primers and probes with degenerate nucleotides to detect divergent species of lyssavirus is described. The probes used in the RT-PCR assay target a highly conserved region at the 5' end of the lyssavirus genome and are modified with either a minor groove binder (MGB) or locked nucleic acid (LNA) nucleotides to increase their melting temperature. The described assay detects all known lyssavirus species with a sensitivity and specificity superior to traditional hemi-nested PCR and the direct fluorescent antibody (DFA) test.

28 Claims, 2 Drawing Sheets

Specification includes a Sequence Listing.

(56) References Cited

OTHER PUBLICATIONS

Picard-Meyer et al., "Cross-Platform Evaluation of Commercial Real-Time SYBR Green RT-PCR Kits for Sensitive and Rapid Detection of European Bat *Lyssavirus* Type 1," *BioMed Res. Int.*, vol. 2015, 18 pp.

Schneider et al., "Improved Efficiency and Robustness in a qPCR and Multiplex End-Point PCR by Twisted Intercalating Nucleic Acid Modified Primers," *PLoS ONE*, vol. 7:e38451, 2012.

Suin et al., "A Two-Step Lyssavirus Real-Time Polymerase Chain Reaction Using Degenerate Primers with Superior Sensitivity to the Fluorescent Antigen Test," *BioMed Res. Int.*, vol. 2014, 12 pp.

Vázquez-Morón et al., "RT-PCR for Detection of All Seven Genotypes of *Lyssavirus* Genus," *J. Virol. Methods*, vol. 135:281-287, 2006.

Wadhwa et al., A Pan-*Lyssavirus* Taqman Real-Time RT-PCR Assay for the Detection of Highly Variable Rabies virus and Other Lyssaviruses, *PLoS Negl. Trop. Dis.*, vol. 11:e0005258, 2017.

Xi et al., "Differentiation of the Seven Major *Lyssavirus* Species by Oligonucleotide Microarray," *J. Clin. Microbiol.*, vol. 50: 619-625, 2012.

\* cited by examiner

| RABV strain ERA RNA dilutions | LN34 qPCR CT Value | Estimated RNA copies/μl by ddPCR |
|---|---|---|
| 1:25 | 31.15 | 89.8 |
| 1:125 | 34.3 | 15.8 |
| 1:625 | 36.48 | 3.66 |
| 1:3125 | 36.99 | 1.38 |
| 1:15625 | | 0.39 |
| 1:78125 | | 0.18 |
| LN34 positive control RNA dilutions | LN34 qPCR CT Value | Estimated RNA copies/μl by ddPCR |
| 1:390625 | 28.82 | 627 |
| 1:1953125 | 31.51 | 121 |
| 1:9765625 | 33.84 | 31.2 |
| 1:48828125 | 36.43 | 3.11 |
| 1:244140625 | 40.59 | 0.94 |
| 1:1220703125 | | 0.28 |

REAL-TIME REVERSE TRANSCRIPTASE-POLYMERASE CHAIN REACTION ASSAY WITH MODIFIED PROBE FOR THE DIAGNOSIS OF RABIES VIRUSES AND OTHER LYSSAVIRUSES

CROSS REFERENCE TO RELATED APPLICATIONS

This application is the U.S. National Stage of International Application No. PCT/US2017/031595, Filed May 8, 2017, published in English under PCT Article 21(2), which claims the benefit of U.S. Provisional Application No. 62/339,323, filed May 20, 2016, which is herein incorporated by reference in its entirety.

FIELD

This disclosure concerns a real-time, reverse transcriptase-polymerase chain reaction (RT-PCR) assay capable of detecting divergent lyssavirus species.

BACKGROUND

Rabies is an acute and progressive viral encephalitis characterized by central nervous disorders, ultimately leading to death. This disease is a major public health problem in Asia and Africa with a global annual human mortality of 59,000. Rabies is caused by several different lyssavirus species of the family Rhabdoviridae; however, rabies virus (RABV) is responsible for the majority of deaths. The lyssavirus species responsible for causing rabies are grouped into 3 phylogroups. Phylogroup I includes RABV, Aravan virus (ARAV), Khujand virus (KHUV), Bokeloh bat lyssavirus (BBLV), Duvenhage virus (DUVV), European bat lyssavirus-1 (EBLV-1), European bat lyssavirus-2 (EBLV-2), Australian bat lyssavirus (ABLV) and Irkut virus (IRKV); Phylogroup II includes Mokola virus (MOKV), Shimoni bat virus (SHIBV) and Lagos bat virus (LBV); and Phylogroup III includes Ikoma virus (IKOV), West Caucasian bat virus (WCBV) and Lleida bat virus (LLBV) (Marston et al., *Emerg Infect Dis* 18(4):664-667, 2012; Arechiga Ceballos et al., *Emerg Infect Dis* 19(5):793-795, 2013; Voloch et al., *Viruses* 6(11):4465-4478, 2014). The significant diversity of genome sequences among rabies and non-rabies lyssaviruses has previously presented challenges in developing a robust, easy to use, pan-lyssavirus diagnostic assay. Currently, definitive rabies diagnoses in both humans and animals depends on post-mortem laboratory results.

The World Health Organization (WHO) and the World Organization for Animal Health (OIE) have defined the direct fluorescent antibody (DFA) test as the gold standard method for post-mortem detection of rabies. DFA is a rapid and sensitive method for diagnosing rabies, but its accuracy depends on the quality of brain tissue, availability of high-quality anti-rabies diagnostic conjugates, accessibility to a fluorescence microscope, and most importantly, an experienced diagnostician (Lembo et al., *Emerg Infect Dis* 12(2):310-313, 2006). With the advent of highly sensitive and specific molecular methods, virus-targeted methods have proven useful to detect rabies virus antigen in nuchal skin biopsy, saliva, eyewashes and even in decomposed samples. Polymerase chain reaction (PCR) based assays are particularly useful as sequences of amplified amplicons can assist in phylogenetic analyses and viral typing. However, current rabies reverse transcriptase (RT)-PCR assays have limited sensitivity, and the current hemi-nested RT-PCR assays have frequently been shown to produce non-specific amplification products. Thus, amplicon sequencing is needed to rule out potential false positive results, which is both time-consuming and labor-intensive.

SUMMARY

A need exists for an improved assay for the detection of RABV and non-rabies lyssaviruses. Current assays, including hemi-nested PCR assays and the DFA test, exhibit limited specificity and sensitivity due to the sequence diversity of lyssaviruses, and typically require at least two separate assays to detect a broad range of RABV and lyssaviruses strains. To address this need, disclosed herein is a real-time RT-PCR assay that utilizes multiplex primers and probes with degenerate nucleotides to detect divergent species of lyssavirus. The probes used in the RT-PCR assay target a short, highly conserved region at the 5' end of the lyssavirus genome and are modified to increase their melting temperature. The disclosed assay detects all known lyssavirus species with a sensitivity and specificity superior to traditional hemi-nested PCR and DFA test.

Provided herein is a method for detecting lyssavirus nucleic acid in a sample. The method includes contacting the sample with at least one forward primer and at least one reverse primer to amplify lyssavirus nucleic acid present in the sample, and at least one probe that detects the amplified lyssavirus nucleic acid. In some embodiments, the at least one forward primer and the at least one reverse primer amplify a 5' region of the lyssavirus genome encompassing at least nucleotides 59-75 or 60-76. In some embodiments, the at least one probe is no more than 20 nucleotides and length and comprises the nucleotide sequence of AACACCYCTACAATGGA (SEQ ID NO: 1), AACACTACTACAATGGA (SEQ ID NO: 2) or ACACCYCTACAATGGAT (SEQ ID NO: 3). In some examples, the at least one probe includes modifications that increase the melting temperature of the probe(s).

Also provided is a kit for detecting lyssavirus nucleic acid. The kit includes primers to amplify lyssavirus nucleic acid, and at least one probe that detects the amplified nucleic acid. In some embodiments, the kit includes at least one forward primer and at least one reverse primer capable of amplifying a 5' region of the lyssavirus genome encompassing at least nucleotides 59-75 or 60-76; and at least one probe that is no more than 20 nucleotides and length and comprises the nucleotide sequence of AACACCYCTACAATGGA (SEQ ID NO: 1), AACACTACTACAATGGA (SEQ ID NO: 2) or ACACCYCTACAATGGAT (SEQ ID NO: 3). In some embodiments, the at least one probe includes modifications that increase the melting temperature of the probe(s).

The foregoing and other objects, features, and advantages of the invention will become more apparent from the following detailed description, which proceeds with reference to the accompanying figures.

BRIEF DESCRIPTION OF THE DRAWINGS

FIG. 1: Shown is an amplicon sequence alignment of assay LN34 from isolates of 14 species of lyssaviruses (SEQ ID NOS: 11-30). The sequences used in this alignment were selected from over 280 published lyssavirus genome sequences in Genbank. For the LN34 assay, the forward primers target nucleotide position 1 to 25, the reverse primer targets position 140-164, and the probe targets position 59 to 75.

FIG. 2: Shown is a table listing the limit of detection using the droplet digital RT-PCR assay.

SEQUENCE LISTING

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, created on Nov. 14, 2018, 169 KB, which is incorporated by reference herein. In the accompanying sequence listing:

SEQ ID NO: 1 is the nucleotide sequence of probes LN34 and LN34a.

SEQ ID NO: 2 is the nucleotide sequence of probe LN34lago.

SEQ ID NO: 3 is the nucleotide sequence of probe LN34m.

SEQ ID NO: 4 is the nucleotide sequence of forward primer 1.

SEQ ID NO: 5 is the nucleotide sequence of forward primer 2.

SEQ ID NO: 6 is the nucleotide sequence of reverse primer.

SEQ ID NO: 7 is the nucleotide sequence of a positive control RABV amplicon.

SEQ ID NO: 8 is the nucleotide sequence of a 13 actin probe.

SEQ ID NO: 9 is the nucleotide sequence of a 13 actin forward primer.

SEQ ID NO: 10 is the nucleotide sequence of a 13 actin reverse primer.

SEQ ID NOS: 11-30 are lyssavirus amplicon sequences from assay LN34.

SEQ ID NOS: 31-118 are lyssavirus N gene sequences.

DETAILED DESCRIPTION

I. Abbreviations

ABLY Australian bat lyssavirus
ARAV Aravan virus
BBLV Bokeloh bat lyssavirus
BS brain stem
ddPCR droplet digital polymerase chain reaction
DFA direct fluorescent antibody
DUVV Duvenhage virus
EBLV-1 European bat lyssavirus-1
EBLV-2 European bat lyssavirus-2
FITC fluorescein-isothiocyanate
IKOV Ikoma virus
IRKV Irkut virus
KHUV Khuj and virus
LBV Lagos bat virus
LNA locked nucleic acid
MGB minor groove binder
MOKV Mokola virus
N nucleoprotein
OIE World Organization for Animal Health
PCR polymerase chain reaction
RABV Rabies virus
RT-PCR reverse transcriptase polymerase chain reaction
SHIBV Shimoni bat virus
SNP single nucleotide polymorphism
TCS tissue culture supernatant
TINA twisted intercalating nucleic acid
Tm melting temperature
WCBV West Caucasian bat virus
WHO World Health Organization

II. Terms and Methods

Unless otherwise noted, technical terms are used according to conventional usage.

Definitions of common terms in molecular biology may be found in Benjamin Lewin, Genes V, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

2,6-Diaminopurine (2-Amino-dA): A base modification that can form three hydrogen bonds when base-paired with dT and can increase the Tm of short oligonucleotides by as much as 1-2° C. per insertion.

5-Hydroxybutynl-2'-deoxyuridine: A duplex-stabilizing modified base that increases oligonucleotide Tm. Oligonucleotides containing 5-hydroxybutynl-2'-deoxyuridine (also known as SUPER T™) can be extended normally by polymerases, including Taq polymerase.

5-Methyl deoxycytidine: A modified base that when substituted for dC increases the Tm of an oligonucleotide by as much as 0.5° C. per insertion.

Animal: Living multi-cellular vertebrate organisms, a category that includes, for example, mammals and birds. The term mammal includes both human and non-human mammals. The term "animal" includes both human and veterinary subjects, for example, humans, non-human primates, dogs, cats, horses, raccoons, bats, rats (and other rodents), mice, foxes, squirrels, opossum, coyotes, wolves, lions, shrews and cows.

Contacting: Placement in direct physical association; includes both in solid and liquid form. "Contacting" is often used interchangeably with "exposed." In some cases, "contacting" includes transfecting, such as transfecting a nucleic acid molecule into a cell. In other examples, "contacting" refers to incubating a molecule with a sample, such as a biological sample.

Degenerate variant: A degenerate variant of a probe or primer includes sequences that have altered nucleic acid sequences, but retain their ability to bind to the target sequences (and identify or amplify the target) with sufficient specificity. In some particular examples, no more than about 1, 2, 5, or 10 nucleic acids are changed from the original sequence. In other examples, the probe or primer retains at least 80%, 85%, 90%, 95%, or 98% sequence identity to the original sequence. Degenerate variants also include probe or primer sequences to which additional sequence has been added, while still retaining the noted specificity of the probe or primer.

Fluorophore: A chemical compound, which when excited by exposure to a particular wavelength of light, emits light (i.e., fluoresces), for example at a different wavelength than that to which it was exposed. Also encompassed by the term "fluorophore" are luminescent molecules, which are chemical compounds which do not require exposure to a particular wavelength of light to fluoresce; luminescent compounds naturally fluoresce. Therefore, the use of luminescent signals eliminates the need for an external source of electromagnetic radiation, such as a laser. An example of a luminescent molecule includes, but is not limited to, aequorin (Tsien, 1998, *Ann. Rev. Biochem.* 67:509).

In some embodiments herein, a probe is labeled with a fluorophore, such as at the 5' end of the probe. Probes used for real-time PCR assays typically include a fluorophore and a quencher.

Fluorophores suitable for use with real-time PCR assays, such as TAQMAN PCR, include, but are not limited to, 6-carboxyfluorescein (FAM), tetrachlorofluorescein (TET), tetramethylrhodamine (TMR), hexachlorofluorescein (HEX), JOE (reporter dye) (TherrnoFisher), ROX (carboxy-X-rhodamine), CAL FLUOR (Fluorescent reporter dye), PULSAR (fluorescent reporter dye), QUASAR (fluorescent reporter dye), TEXAS RED (rhodamine dye), Cy3 (Indocarbocyanine dyes) and Cy5 (Indodicarbocyanin dyes).

Other examples of fluorophores are provided in U.S. Pat. No. 5,866,366. These include: 4-acetamido-4'-isothiocyanatostilbene-2,2'disulfonic acid, acridine and derivatives such as acridine and acridine isothiocyanate, 5-(2'-aminoethyl) amino-naphthalene-1-sulfonic acid (EDANS), 4-amino-N-[3-vinylsulfonyl)phenyl]-naphthalimide-3,5 disulfonate (*Lucifer* Yellow VS), N-(4-anilino-1-naphthyl)-maleimide, anthranilamide, Brilliant Yellow, coumarin and derivatives such as coumarin, 7-amino-4-methylcoumarin (AMC, Coumarin 120), 7-amino-4-trifluoromethylcouluarin (Coumaran 151); cyanosine; 4',6-diaminidino-2-phenylindole (DAPI); 5', 5"-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansyl chloride); 4-(4'-dimethyl-aminophenylazo)benzoic acid (DABCYL); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein, fluorescein isothiocyanate (FITC), and QFITC (XRITC); fluorescamine; IR144; IR1446; Malachite Green isothiocyanate; 4-methylumbelliferone; ortho cresolphthalein; nitrotyrosine; pararosaniline; Phenol Red; B-phycoerythrin; o-phthaldialdehyde; pyrene and derivatives such as pyrene, pyrene butyrate and succinimidyl 1-pyrene butyrate; Reactive Red 4 (Cibacron.RTM. Brilliant Red 3B-A); rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, sulforhodamine B, sulforhodamine 101 and sulfonyl chloride derivative of sulforhodamine 101 (Texas Red® dye); N,N,N',N'-tetramethyl-6-carboxyrhodamine (TAMRA); tetramethyl rhodamine; tetramethyl rhodamine isothiocyanate (TRITC); riboflavin; rosolic acid and terbium chelate derivatives.

Other fluorophores include thiol-reactive europium chelates that emit at approximately 617 nm (Heyduk and Heyduk, *Analyt. Biochem.* 248:216-27, 1997; *J. Biol. Chem.* 274:3315-22, 1999).

Other fluorophores include cyanine, merocyanine, stryl, and oxonyl compounds, such as those disclosed in U.S. Pat. Nos. 5,627,027; 5,486,616; 5,569,587; and 5,569,766, and in published PCT application no. US98/00475, each of which is incorporated herein by reference. Specific examples of fluorophores disclosed in one or more of these patent documents include Cy3 and Cy5, for instance, and substituted versions of these fluorophores.

Other fluorophores include GFP, LISSAMINE(Lissamine green dye)™ dye, diethylaminocoumarin, fluorescein chlorotriazinyl, naphthofluorescein, 4,7-dichlororhodamine and xanthene (as described in U.S. Pat. No. 5,800,996 to Lee et al., herein incorporated by reference) and derivatives thereof. Other fluorophores are known to those skilled in the art, for example those available from Molecular Probes (Eugene, Oreg.).

Hybridization: Oligonucleotides (such as primers and probes) and their analogs hybridize by hydrogen bonding, which includes Watson-Crick, Hoogsteen or reversed Hoogsteen hydrogen bonding, between complementary bases. Generally, nucleic acid consists of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and the bonding of the pyrimidine to the purine is referred to as "base pairing." More specifically, A will hydrogen bond to T or U, and G will bond to C. "Complementary" refers to the base pairing that occurs between two distinct nucleic acid sequences or two distinct regions of the same nucleic acid sequence.

"Specifically hybridizable" and "specifically complementary" are terms that indicate a sufficient degree of complementarity such that stable and specific binding occurs between the oligonucleotide (or its analog) and the DNA or RNA target. The oligonucleotide or oligonucleotide analog need not be 100% complementary to its target sequence to be specifically hybridizable. An oligonucleotide or analog is specifically hybridizable when there is a sufficient degree of complementarity to avoid non-specific binding of the oligonucleotide or analog to non-target sequences under conditions where specific binding is desired, for example under physiological conditions in the case of in vivo assays or systems. Such binding is referred to as specific hybridization.

Hybridization conditions resulting in particular degrees of stringency will vary depending upon the nature of the hybridization method of choice and the composition and length of the hybridizing nucleic acid sequences. Generally, the temperature of hybridization and the ionic strength (especially the $Na^+$ and/or $Mg^{++}$ concentration) of the hybridization buffer will determine the stringency of hybridization, though wash times also influence stringency. Calculations regarding hybridization conditions required for attaining particular degrees of stringency are discussed by Sambrook et al. (ed.), *Molecular Cloning: A Laboratory Manual*, $2^{nd}$ ed., vol. 1-3, Cold Spring Harbor Laboratory Press, Cold Spring Harbor, N.Y., 1989, chapters 9 and 11; and Ausubel et al. *Short Protocols in Molecular Biology*, 4th ed., John Wiley & Sons, Inc., 1999. For purposes of the present disclosure, "stringent conditions" encompasses conditions under which hybridization will only occur if there is less than 25% mismatch between the hybridization molecule and the target sequence. "Stringent conditions" may be broken down into particular levels of stringency for more precise definition. Thus, as used herein, "moderate stringency" conditions are those under which molecules with more than 25% sequence mismatch will not hybridize; conditions of "medium stringency" are those under which molecules with more than 15% mismatch will not hybridize, and conditions of "high stringency" are those under which sequences with more than 10% mismatch will not hybridize. Conditions of "very high stringency" are those under which sequences with more than 6% mismatch will not hybridize.

Isolated: An "isolated" biological component (such as a nucleic acid, protein or virus) has been substantially separated or purified away from other biological components (such as cell debris, or other proteins or nucleic acids). Biological components that have been "isolated" include those components purified by standard purification methods. The term also embraces recombinant nucleic acids or proteins, as well as chemically synthesized nucleic acids or peptides.

Label: A detectable compound or composition that is conjugated directly or indirectly to another molecule to facilitate detection of that molecule. Specific, non-limiting examples of labels include radioactive isotopes, enzyme substrates, co-factors, ligands, chemiluminescent or fluorescent molecules, haptens and enzymes. Labels may be natural or synthetic, and may also be heterologous in the sense that they do not naturally occur in combination with the molecule to which it is conjugated. Conjugation can occur, for example, by covalent attachment of the label to the other molecule.

Locked nucleic acid (LNA): A bicyclic nucleic acid where a ribonucleoside is linked between the 2'-oxygen and the 4'-carbon atoms with a methylene unit. This link restricts the flexibility of the ribofuranose ring of the nucleotide, locking the ribose in the 3'-endo conformation. The LNA also induces adjacent bases to adopt a conformation of the more thermodynamically stable form of the A duplex. The locked ribose conformation enhances base stacking and backbone pre-organization, which significantly increases the melting temperature of the nucleic acid. LNA oligonucleotides can be synthesized by standard phosphoramidite chemistry using DNA-synthesizers. In addition, LNA can be mixed with DNA, RNA as well as other nucleic acid analogs.

Lyssavirus: A genus of viruses that is part of the Rhabdoviridae family within the order Mononegavirales (viruses with a single-stranded, negative sense genome). Lyssaviruses are the etiological agents of rabies encephalitis in warm-blooded animals and humans. The lyssavirus species responsible for causing rabies are grouped into 3 phylogroups. Phylogroup I includes rabies virus (RABV), Aravan virus (ARAV), Khuj and virus (KHUV), Bokeloh bat lyssavirus (BBLV), Duvenhage virus (DUVV), European bat lyssavirus-1 (EBLV-1), European bat lyssavirus-2 (EBLV-2), Australian bat lyssavirus (ABLY) and Irkut virus (IRKV); Phylogroup II includes Mokola virus (MOKV), Shimoni bat virus (SHIBV) and Lagos bat virus (LBV); and Phylogroup III includes Ikoma virus (IKOV), West Caucasian bat virus (WCBV) and Lleida bat virus (LLBV) (Marston et al., *Emerg Infect Dis* 18(4):664-667, 2012; Arechiga Ceballos et al., *Emerg Infect Dis* 19(5):793-795, 2013; Voloch et al., *Viruses* 6(11):4465-4478, 2014).

Melting temperature (Tm): In the context of an oligonucleotide duplex, Tm is the temperature at which half of the oligonucleotide molecules are single-stranded and half are double-stranded. Thus, the melting temperature of an oligonucleotide probe or primer is the temperature at which half of the probe or primer molecules are bound to their target (complementary) oligonucleotides and half are unbound.

Minor groove binder (MGB): A composition or moiety that binds in a non-intercalating manner into the minor groove of double stranded DNA, RNA or hybrids thereof. A variety of minor groove binders are known in the art (see, for example, U.S. Pat. Nos. 5,801,155; 6,492,346; 6,084,102; and 6,727,356; and Wemmer and Dervan, *Curr Opin Struct Biol* 7:355-361, 1997). In some embodiments herein, the MGB is a trimer of 1,2-dihydro-(3H)-pyrrolo[3,2-e]indole-7-carboxylate ($CDPI_3$) (Afonina et al., *Nucleic Acids Res* 25(13):2657-2660, 1997) or a pentamer of N-methylpyrrole-4-carbox-2-amide ($MPC_5$) (U.S. Pat. No. 7,943,752).

Probes and primers: A probe comprises an isolated nucleic acid molecule attached to a detectable label or other reporter molecule. Typical labels include radioactive isotopes, enzyme substrates, co-factors, ligands, chemiluminescent or fluorescent agents, haptens, and enzymes. Methods for labeling and guidance in the choice of labels appropriate for various purposes are discussed, for example, in Sambrook et al. (ed.), *Molecular Cloning: A Laboratory Manual*, $2^{nd}$ ed., vol. 1-3, Cold Spring Harbor Laboratory Press, Cold Spring Harbor, N.Y., 1989 and Ausubel et al. *Short Protocols in Molecular Biology*, 4th ed., John Wiley & Sons, Inc., 1999.

Primers are short nucleic acid molecules, for instance DNA oligonucleotides 10 nucleotides or more in length, for example that hybridize to contiguous complementary nucleotides or a sequence to be amplified. Primer oligonucleotides may be about 10, 12, 15, 18, 20, 25, 30, or 50 nucleotides or more in length. Primers can be annealed to a complementary target DNA strand by nucleic acid hybridization to form a hybrid between the primer and the target DNA strand, and then the primer extended along the target DNA strand by a DNA polymerase enzyme. Primer pairs can be used for amplification of a nucleic acid sequence, for example, by the polymerase chain reaction (PCR) or other nucleic-acid amplification methods known in the art. Other examples of amplification include strand displacement amplification, as disclosed in U.S. Pat. No. 5,744,311; transcription-free isothermal amplification, as disclosed in U.S. Pat. No. 6,033,881; repair chain reaction amplification, as disclosed in WO 90/01069; ligase chain reaction amplification; gap filling ligase chain reaction amplification, as disclosed in 5,427,930; and NASBA™ RNA transcription-free amplification, as disclosed in U.S. Pat. No. 6,025,134.

Methods for preparing and using nucleic acid probes and primers are described, for example, in Sambrook et al. (ed.), *Molecular Cloning: A Laboratory Manual*, $2^{nd}$ ed., vol. 1-3, Cold Spring Harbor Laboratory Press, Cold Spring Harbor, N.Y., 1989; Ausubel et al. *Short Protocols in Molecular Biology*, 4th ed., John Wiley & Sons, Inc., 1999; and Innis et al. PCR Protocols, *A Guide to Methods and Applications*, Academic Press, Inc., San Diego, Calif., 1990. Amplification primer pairs can be derived from a known sequence, for example, by using computer programs intended for that purpose such as Primer (Version 0.5, © 1991, Whitehead Institute for Biomedical Research, Cambridge, Mass.).

Quencher: A substance that absorbs excitation energy from a fluorophore when in close proximity. Probes used for real-time PCR assays, such as TaqMan®'PCR, typically include a fluorophore and a quencher. Quenchers suitable for use with real-time PCR assays include, but are not limited to, ZEN (quencher dye), IOWA BLACK (dark quencher dye)® dye FQ, tetramethylrhodamine (TAMRA), black hole quencher (BHQ)1, BHQ2, BHQ3, nonfluorescent quencher (NFQ) and 4-(4'-dimethylaminophenylazo)benzoic acid (DABCYL). In some cases, a probe contains two quenchers.

Rabies: A viral disease that causes acute encephalitis (inflammation of the brain) in warm-blooded animals. Rabies is zoonotic (transmitted by animals), most commonly by a bite from an infected animal but occasionally by other forms of contact. Rabies is almost frequently fatal if post-exposure prophylaxis is not administered prior to the onset of severe symptoms. Rabies is caused by viruses of the Lyssavirus genus.

Reverse-transcription PCR (RT-PCR): A method for detecting, quantifying, or utilizing RNA present in a sample by a procedure wherein the RNA serves as a template for the synthesis of cDNA by a reverse transcriptase followed by PCR to amplify the cDNA. RT-PCR can be used in combination with quantitative real time PCR as a method of measuring the quantity of starting template in the reaction.

Sample: Encompasses a sample obtained from an animal, plant, or the environment, whether unfixed, frozen, or fixed in formalin or paraffin. As used herein, samples include all clinical samples useful for detection of viral infection in subjects, including, but not limited to, cells, tissues, and bodily fluids. In some embodiments, the sample is a biological sample obtained from a human or veterinary subject, such as, for example, a fluid, cell and/or tissue sample. In some examples herein, the biological sample is a fluid sample. Fluid sample include, but are not limited to, serum, blood, plasma, urine, feces, saliva, cerebral spinal fluid (CSF) or other bodily fluid. Biological samples can also refer to cells or tissue samples, such as biopsy samples (for example, skin biopsies), tissue sections (such as brain tissue), corneal tissue samples, or isolated leukocytes. Samples also include samples obtained from inanimate objects or reservoirs within an indoor or outdoor environment, including, but not limited to: soil, water, dust, and air samples.

Sequence identity: The similarity between amino acid or nucleic acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a given gene or protein will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237-244, 1988; Higgins and Sharp, *CABIOS* 5:151-153, 1989; Corpet et al., *Nucleic Acids Research* 16:10881-10890, 1988; and Pearson and Lipman, *Proc. Natl. Acad. Sci. U.S.A.* 85:2444, 1988. Altschul et al., *Nature Genet.* 6:119-129, 1994.

The NCBI Basic Local Alignment Search Tool (BLAST™) (Altschul et al., *J. Mol. Biol.* 215:403-410, 1990) is available from several sources, including the National Center for Biotechnology Information (NCBI, Bethesda, Md.) and on the Internet, for use in connection with the sequence analysis programs blastp, blastn, blastx, tblastn and tblastx.

In some embodiments herein, provided are oligonucleotide sequences at least 80%, at least 85%, at least 90%, at least 95%, at least 96%, at least 97%, at least 98% or at least 99% identical to any one of SEQ ID NOS: 1-6.

Subject: Living multi-cellular vertebrate organisms, a category that includes both human and non-human mammals.

Twisted intercalating nucleic acid (TINA): An intercalator that can stabilize Watson-Crick antiparallel duplex DNA (Schneider et al., *PLoS One* 7(6):e38451, 2012). TINA molecules can be used at the at 5' end of an oligonucleotide to increase Tm.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. "Comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Introduction

Several real-time RT-PCR assays have been previously developed for the detection of RABV or non-rabies lyssaviruses. However, the prior assays exhibit limited specificity and sensitivity due to the sequence diversity of lyssaviruses, and usually require at least two separate assays to detect a broad range of RABV and lyssaviruses strains. SYBR Green based real-time RT-PCR assays are able to detect more RABV and lyssavirus strains than other diagnostic assays, but are relatively prone to generating false positive results due to the non-specific binding of SYBR Green (Dupuis et al., *J Clin Microbiol* 53(9):2983-2989, 2015; Hayman et al., *J Virol Methods* 177(1):87-93, 2011; Coertse et al., *J Clin Microbiol* 48(11):3949-3955, 2010; Vazquez-Moron et al., *J Virol Methods* 135(2):281-287, 2006). To address the need for an improved lyssavirus detection assay, disclosed herein is a new real-time RT-PCR assay that utilizes multiplex primers and probes with degenerate nucleotides, modified to increase their melting temperature (Tm). For example, the modified probes can include, for example, a minor groove binder (MGB) or locked nucleic acid (LNA) nucleotides. The assay disclosed herein detects all known lyssavirus species with a sensitivity and specificity superior to traditional hemi-nested PCR and DFA.

Figure 1:
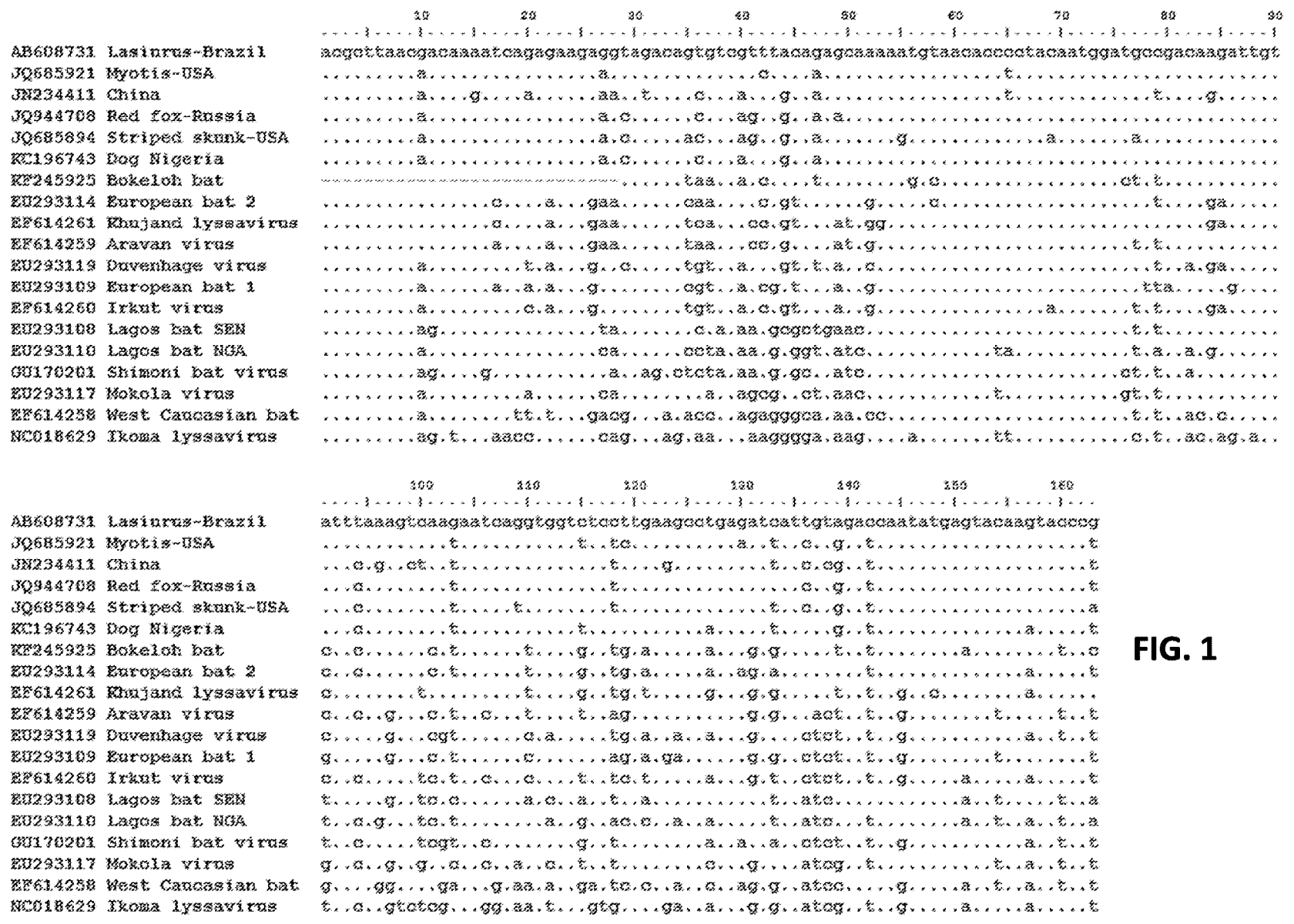

In particular, two assays are described herein, each utilizing a different type of probe. The LN34 assay utilizes nucleic acid probes that are modified by locked nucleic acid (LNA) nucleotides; the LN34m assay uses a probe modified at the 3' end with a minor groove binder (MGB). The probes are capable of hybridizing to divergent lyssavirus species by targeting a very short region of the lyssavirus genome (nucleotides 59-75 or 60-76) that is highly conserved near the ATG translation start site of the nucleoprotein (N) gene (see FIG. 1). Previously described assays have utilized longer probes in order for the probes to have a Tm compatible with RT-PCR. However, the longer the probe, the less likely it is that the probe will hybridize to divergent species of lyssavirus. Therefore, the assays disclosed herein use an alternative approach—modifying the probes to increase their Tm, such as with LNA nucleotides or a MGB, to enable their use in RT-PCR.

To further enable detection of divergent lyssavirus species, the primer and probe sequences were designed with degenerate nucleotides. The sequences of the primers and probes disclosed herein are shown in Table 3.

The LNA probes LN34 and LN34a allowed for the detection of nearly all lyssavirus species tested, except for a subspecies of Lagos virus (LNA probes LN34 and LN34a have the same nucleotide sequence, but differ by the location of the LNA nucleotides). A third LNA probe (LN341ago) was designed to specifically detect Lagos virus. All LNA probes include a 5' fluorescent label (FAM) and a 3' quencher (BHQ1). A single MGB-modified probe (LN34m) was designed for the LN34m assay. In addition to the 3' MGB, this probe includes a 5' fluorescent label (6FAM) and a 3' quencher (NFG). Both RT-PCR assays use a multiplex of two forward primers and a reverse primer that includes several degenerate nucleotides.

The RT-PCR assays disclosed herein were tested using a validation panel of 88 lyssavirus isolates, including 59 variants of RABV from Asia, Africa, Europe, South America and North America; eight non-rabies lyssavirus species from phylogroup I; two non-rabies lyssavirus species from phylogroup II; and one non-rabies lyssavirus species from phylogroup III. It was determined that the LN34 and LN34m assays were both capable of detecting all variants from the validation panel except for one subspecies of Lagos virus. However, this subspecies was detected using the multiplex LN34 or LN34m assay with the subspecies-specific Lagos virus probe LN341ago. The sensitivity and specificity of the two assays were similar for most of the variants in the panel.

IV. Lyssavirus Detection Assay

Disclosed herein is a real-time RT-PCR assay that utilizes multiplex primers and probes with degenerate nucleotides to detect divergent species of lyssavirus. The probes used in the RT-PCR assay target a highly conserved region at the 5' end of the lyssavirus genome and are modified to increase their melting temperature (Tm). In some examples, the probes are modified with either a MGB or LNA nucleotides to increase their Tm. The disclosed assay detects all known lyssavirus species with a sensitivity and specificity superior to traditional hemi-nested PCR and DFA test. The disclosed assay can be used, for example, to diagnose a rabies virus or non-rabies lyssavirus infection in a subject.

Provided herein is a method for detecting lyssavirus nucleic acid in a sample by contacting the sample with at least one forward primer and at least one reverse primer to amplify lyssavirus nucleic acid present in the sample; and at least one probe that detects the amplified lyssavirus nucleic acid. The at least one forward primer and the at least one reverse primer amplify a 5' region of the lyssavirus genome encompassing at least nucleotides 59-75 or 60-76 (see FIG. 1). In some embodiments, the at least one probe is no more than 20 nucleotides in length, such as no more than 19 nucleotides in length, no more than 18 nucleotides in length, or no more than 17 nucleotides in length, and includes the nucleotide sequence of AACACCYCTACAATGGA (SEQ ID NO: 1), AACACTACTACAATGGA (SEQ ID NO: 2) or ACACCYCTACAATGGAT (SEQ ID NO: 3). In some embodiments, the at least one probe comprises at least one modification to increase its melting temperature (Tm).

In some embodiments, the at least one forward primer is no more than 40 nucleotides in length, such as no more than 35 nucleotides in length, no more than 30 nucleotides in length, or no more than 25 nucleotides in length. In some examples, the nucleotide sequence of the at least one forward primer includes ACGCTTAACAACCAGATCAAAGAA (SEQ ID NO: 4) or ACGCTTAACAACCAGATCAAAGAAG (SEQ ID NO: 5). In specific examples, the at least one forward primer is no more than 40, 39, 38, 37, 36, 35, 34, 33, 32, 31, 30, 29, 28, 27, 26, 25 or 24 nucleotides in length and/or includes the sequence ACGCTTAACAACCAGATCAAAGAA (SEQ ID NO: 4) or ACGCTTAACAACCAGATCAAAGAAG (SEQ ID NO: 5).

In some embodiments, the at least one reverse primer is no more than 40 nucleotides in length, such as no more than 35 nucleotides in length, no more than 30 nucleotides in length, or no more than 25 nucleotides in length. In some examples, the nucleotide sequence of the at least one reverse primer includes the sequence CMGGGTAYTTRTAYTCATAYTGRTC (SEQ ID NO: 6). In specific examples, the at least one reverse primer is no more than 40, 39, 38, 37, 36, 35, 34, 33, 32, 31, 30, 29, 28, 27, 26 or 25 nucleotides in length and/or includes the sequence CMGGGTAYTTRTAYTCATAYTGRTC (SEQ ID NO: 6).

In particular embodiments, the method includes contacting the sample with a first forward primer including the sequence ACGCTTAACAACCAGATCAAAGAA (SEQ ID NO: 4), a second forward primer including the sequence ACGCTTAACAACCAGATCAAAGAAG (SEQ ID NO: 5), and a reverse primer including the sequence CMGGGTAYTTRTAYTCATAYTGRTC (SEQ ID NO: 6).

The at least one probe utilized in the provided assay includes at least one modification to increase melting temperature (Tm). When multiple modifications are present, the modifications can be the same modification or different modifications. Modifications that increase the Tm of an oligonucleotide are well-known in the art, and include but are not limited to, locked nucleic acid (LNA) nucleotides, minor groove binders (MGB), 5-hydroxybutyn1-2'-deoxyuridine (SUPER T™), 2,6-diaminopurine (2-Amino-dA), 5-methyl deoxycytidine, and twisted intercalating nucleic acid (TINA).

In some embodiments, the at least one probe is modified to include at least one, at least two, at least three, at least four or at least five LNA nucleotides. In some examples, the at least one probe is modified to include at least 6 or at least 7 LNA nucleotides.

In particular embodiments, the at least one probe includes the nucleotide sequence AACACCYCTACAATGGA (SEQ ID NO: 1), and the probe includes LNA nucleotides at positions 4, 9, 10, 13 and 14. In some examples, the probe further includes LNA nucleotides at positions 3 and 8.

In other particular embodiments, the at least one probe includes the nucleotide sequence AACACTACTACAATGGA (SEQ ID NO: 2), and the probe includes LNA nucleotides at positions 3, 4, 8, 9, 10, 13 and 14.

In some embodiments, the at least one probe is modified to include a MGB.

In particular embodiments, the at least one probe includes the nucleotide sequence ACACCYCTACAATGGAT (SEQ ID NO: 3), and the probe includes a MGB at the 3' terminus.

In some examples of the disclosed method, the method includes contacting the sample with a first forward primer comprising the sequence ACGCTTAACAACCAGATCAAAGAA (SEQ ID NO: 4), a second forward primer comprising the sequence ACGCTTAACAACCAGATCAAAGAA (SEQ ID NO: 5), a reverse primer comprising the sequence CMGGGTAYTTRTAYTCATAYTGRTC (SEQ ID NO: 6) and a first probe comprising the sequence AACACCYCTACAATGGA (SEQ ID NO: 1), wherein positions 4, 9, 10, 13 and 14 are LNA nucleotides; AACACCYCTACAATGGA (SEQ ID NO: 1), wherein positions 3, 4, 8, 9, 10, 13 and 14 are LNA nucleotides; or ACACCYCTACAATGGAT (SEQ ID NO: 3), wherein the probe comprises a MGB at the 3' terminus. In specific examples, the method further includes contacting the sample with a second probe comprising the sequence AACACTACTACAATGGA (SEQ ID NO: 2), wherein positions 3, 4, 8, 9, 10, 13 and 14 are LNA nucleotides.

In some embodiments, the at least one probe, the first probe, the second probe, or any combination thereof, comprise(s) a 5' fluorescent label, a 3' quencher, or both. In some examples, the fluorescent label is FAM. In some examples, the 3' quencher is BHQ1 or NFQ.

In some embodiments, the sample is a tissue sample, such as brain tissue sample, a skin biopsy or a corneal tissue sample. In other embodiments, the sample is a fluid sample, such as a saliva, blood, serum or cerebral spinal fluid (CSF) sample.

In some embodiments, the sample is a post-mortem sample. In other embodiments, the sample is an ante-mortem sample.

In specific examples, the sample is a post-mortem brain tissue sample.

In other specific examples, the sample is an ante-mortem saliva, serum, blood, CSF, skin biopsy or corneal tissue sample.

In some embodiments, the sample is obtained from a human. In other embodiments, the sample is obtained from a non-human animal. In some examples, the non-human animal is a dog, cat, coyote, skunk, fox, raccoon, mongoose, lion, shrew, rodent or civet.

In some embodiments, the lyssavirus nucleic acid is lyssavirus RNA or cDNA. For detection of lyssavirus RNA, the disclosed detection method further includes contacting the sample with a reverse transcriptase to generate cDNA.

V. Lyssavirus Diagnostic Kits

Further provided herein are kits for detecting lyssavirus nucleic acid, such as lyssavirus nucleic acid in a sample.

In some embodiments, the kit includes at least one forward primer and at least one reverse primer capable of amplifying a 5' region of the lyssavirus genome encompassing at least nucleotides 59-75 or 60-76 (see FIG. 1).

In some embodiments, the kit includes at least one probe that is no more than 20 nucleotides in length, such as no more than 19 nucleotides in length, no more than 18 nucleotides in length, or no more than 17 nucleotides in length, and includes the nucleotide sequence of AACACCYCTACAATGGA (SEQ ID NO: 1), AACACTACTACAATGGA (SEQ ID NO: 2) or ACACCYCTACAATGGAT (SEQ ID NO: 3). In particular embodiments, the at least one probe comprises at least one modification to increase melting temperature (Tm).

In some embodiments of the kit, the at least one forward primer is no more than 40 nucleotides in length, such as no more than 35 nucleotides in length, no more than 30 nucleotides in length, or no more than 25 nucleotides in length. In some examples, the nucleotide sequence of the at least one forward primer includes ACGCTTAACAACCAGATCAAAGAA (SEQ ID NO: 4) or ACGCTTAACAACCAGATCAAAGAAG (SEQ ID NO: 5). In specific examples, the at least one forward primer is no more than 40, 39, 38, 37, 36, 35, 34, 33, 32, 31, 30, 29, 28, 27, 26, 25 or 24 nucleotides in length and/or includes the sequence ACGCTTAACAACCAGATCAAAGAA (SEQ ID NO: 4) or ACGCTTAACAACCAGATCAAAGAAG (SEQ ID NO: 5).

In some embodiments of the kit, the at least one reverse primer is no more than 40 nucleotides in length, such as no more than 35 nucleotides in length, no more than 30 nucleotides in length, or no more than 25 nucleotides in length. In some examples, the nucleotide sequence of the at least one reverse primer includes the sequence CMGGGTAYTTRTAYTCATAYTGRTC (SEQ ID NO: 6). In specific examples, the at least one reverse primer is no more than 40, 39, 38, 37, 36, 35, 34, 33, 32, 31, 30, 29, 28, 27, 26 or 25 nucleotides in length and/or includes the sequence CMGGGTAYTTRTAYTCATAYTGRTC (SEQ ID NO: 6).

In particular embodiments, the kit includes a first forward primer, a second forward primer and a reverse primer, wherein the first forward primer comprises the sequence ACGCTTAACAACCAGATCAAAGAA (SEQ ID NO: 4), the second forward primer comprises the sequence ACGCTTAACAACCAGATCAAAGAA (SEQ ID NO: 5) and the reverse primer comprises the sequence CMGGGTAYTTRTAYTCATAYTGRTC (SEQ ID NO: 6).

The probes of the provided kit include at least one modification to increase their Tm. When multiple modifications are present, the modifications can be the same modification or different modifications. Modifications that increase the Tm of an oligonucleotide are well-known in the art, and include but are not limited to, LNA nucleotides, MGB, 5-hydroxybutyn1-2'-deoxyuridine, 2-Amino-dA, 5-methyl deoxycytidine, and TINA.

In some embodiments of the kit, the at least one probe is modified to include at least one, at least two, at least three, at least four or at least five LNA nucleotides. In some examples, the at least one probe is modified to include at least 6 or at least 7 LNA nucleotides.

In particular embodiments, the at least one probe includes the nucleotide sequence AACACCYCTACAATGGA (SEQ ID NO: 1), and the probe includes LNA nucleotides at positions 4, 9, 10, 13 and 14. In some examples, the probe further includes LNA nucleotides at positions 3 and 8.

In other particular embodiments, the at least one probe includes the nucleotide sequence AACACTACTACAATGGA (SEQ ID NO: 2), and the probe includes LNA nucleotides at positions 3, 4, 8, 9, 10, 13 and 14.

In some embodiments, the at least one probe is modified to include a MGB.

In particular embodiments, the at least one probe includes the nucleotide sequence ACACCYCTACAATGGAT (SEQ ID NO: 3), and the probe includes a MGB at the 3' terminus.

In particular examples, the kit includes a first forward primer comprising the sequence ACGCTTAACAACCAGATCAAAGAA (SEQ ID NO: 4), a second forward primer comprising the sequence ACGCTTAACAACCAGATCAAAGAA (SEQ ID NO: 5), a reverse primer comprising the sequence CMGGGTAYTTRTAYTCATAYTGRTC (SEQ ID NO: 6) and a first probe comprising the sequence AACACCYCTACAATGGA (SEQ ID NO: 1), wherein positions 4, 9, 10, 13 and 14 are LNA nucleotides; AACACCYCTACAATGGA (SEQ ID NO: 1), wherein positions 3, 4, 8, 9, 10, 13 and 14 are LNA nucleotides; ACACCYCTACAATGGAT (SEQ ID NO: 3), wherein the probe comprises a MGB at the 3' terminus. In specific examples, the kit further includes a second probe comprising the sequence AACACTACTACAATGGA (SEQ ID NO: 2), wherein positions 3, 4, 8, 9, 10, 13 and 14 are LNA nucleotides.

In some embodiments, the at least one probe, the first probe, the second probe, or any combination thereof, comprise(s) a 5' fluorescent label, a 3' quencher, or both. In some examples, the fluorescent label is FAM. In some examples, the 3' quencher is BHQ1 or NFQ.

The provided kits enable a user to detect lyssavirus nucleic acid (such as RNA) in a biological sample and/or to diagnose a lyssavirus infection. In some embodiments, the primer(s) and probe(s) are provided in individual containers. In other examples, mixtures of the primers and/or probe(s) are provided in a single container. Kits can optionally include instructions for carrying out the disclosed methods for detection of lyssavirus nucleic acid. In particular examples, the kits further include reagents useful in performing the RT-PCR reactions, such as a DNA polymerase, nucleotides and/or buffers.

The primers and probes provided in disclosed kits may be provided in any form practicable, such as suspended in an aqueous solution or as a freeze-dried or lyophilized powder, for instance. Kits according to this disclosure can also include instructions, usually written instructions, to assist the user in carrying out the detection methods disclosed herein. Such instructions can optionally be provided on a computer readable medium or as a link to an internet page.

The container(s) in which the reagents are supplied can be any conventional container that is capable of holding the supplied form, for instance, microfuge tubes, ampoules, or bottles. In some applications, the primers and probes, DNA polymerase(s), and/or other reagent mixtures useful for performing the RT-PCR detection assay may be provided in pre-measured single use amounts in individual, typically disposable, tubes, microtiter plates, or equivalent containers. The containers may also be compatible with a specific automated liquid handling apparatus.

The amount of a reagent supplied in the kit can be any appropriate amount, depending for instance on the market to which the product is directed. For instance, if the kit is adapted for research or clinical use, the amount of each reagent would likely be an amount sufficient for multiple screening assays. In other examples where the kit is intended for high throughput industrial use, the amounts could be sufficiently increased to accommodate multiple hundreds of assays.

The following examples are provided to illustrate certain particular features and/or embodiments. These examples should not be construed to limit the disclosure to the particular features or embodiments described.

EXAMPLES

Example 1: Materials and Methods

This example describes the materials and experimental procedures used for the studies described in Example 2.

Samples

Brain tissue samples from rabid animals were obtained via routine surveillance activity of the Centers for Disease Control and Prevention (CDC; Atlanta, Ga., USA). Moribund and dead animals, or animals involved in human rabies exposure were collected by the US State Health Departments, US Department of Agriculture and veterinary laboratories during routine surveillance and diagnostic service.

Validation Samples: A total of 88 representative lyssaviruses were selected in the validation panel. The virus isolates and the details about the host species, geographical location and source of extraction are summarized in Table 1. Viruses were amplified in tissue culture only if a limited amount of original material was available. Total RNA was extracted from brain as well as tissue culture supernatant using TRIZOL™ reagent (Invitrogen) according to the manufacturer's instructions.

TABLE 1

Validation samples-Rabies virus positive samples used to validate the sensitivity of the LN34 Real-Time RT-PCR assay

| S. No. | Isolate Origin | Host | Source | Virus Species | LN34m^ | LN34^ |
|---|---|---|---|---|---|---|
| 1 | Russia | Dog | TCS | RABV | 16.542 | ND |
| 2 | China | Dog | TCS | RABV | 28.989 | 28.895 |
| 3 | Argentina | Dog | TCS | RABV | 23.143 | 23.331 |
| 4 | Texas, USA | Coyote | TCS | RABV | 17.206 | ND |
| 5 | Thailand | Dog | TCS | RABV | 17.425 | 16.504 |
| 6 | Wisconsin, USA | Skunk | TCS | RABV | 19.871 | 18.374 |
| 7 | Mexico | Dog | TCS | RABV | 25.348 | 25.341 |
| 8 | Texas, USA | Coyote | TCS | RABV | 19.801 | 18.572 |
| 9 | Arizona, USA | Fox | TCS | RABV | 19.705 | 19.063 |
| 10 | California, USA | Skunk | TCS | RABV | 20.904 | 21.001 |
| 11 | Texas, USA | Fox | TCS | RABV | 16.542 | ND |
| 12 | Texas, USA | Skunk | TCS | RABV | 29.524 | 14.369 |
| 13 | Sri Lanka | Dog | TCS | RABV | 22.037 | 22.427 |
| 14 | Georgia, USA | Raccoon | TCS | RABV | 17.206 | 18.570 |
| 15 | Puerto Rico, USA | Mongoose | TCS | RABV | 20.715 | 19.749 |
| 16 | Tunisia | Dog | TCS | RABV | 22.318 | 22.089 |
| 17 | India | Dog | TCS | RABV | 20.767 | 19.454 |
| 18 | India | Dog | TCS | RABV | 19.801 | 21.066 |
| 19 | India | Dog | TCS | RABV | 25.703 | 26.135 |
| 20 | India | Dog | TCS | RABV | 29.210 | 28.878 |
| 21 | Arizona, USA | Bat-*Lasiurus* spp. | BS | RABV | 26.892 | 27.354 |
| 22 | Brazil | Bat-*Desmodus* spp. | BS | RABV | 25.617 | 24.447 |
| 23 | Mexico | Bat-*Desmodus* spp. | BS | RABV | 25.033 | 23.005 |
| 24 | Washington, USA | Bat-*Lasionycteris* spp. | BS | RABV | 25.117 | 25.164 |
| 25 | Washington, USA | Bat-*Myotis* spp. | BS | RABV | 29.953 | 28.473 |
| 26 | Tennessee, USA | Bat-*Lasiurus* spp. | BS | RABV | 23.068 | 22.452 |
| 27 | Tennessee, USA | Bat-*Lasiurus* spp. | BS | RABV | 22.096 | 20.957 |

TABLE 1-continued

Validation samples-Rabies virus positive samples used to validate the sensitivity of the LN34 Real-Time RT-PCR assay

| S. No. | Isolate Origin | Host | Source | Virus Species | LN34m^ | LN34^ |
|---|---|---|---|---|---|---|
| 28 | Tennessee, USA | Bat-*Lasiurus* spp. | BS | RABV | 27.265 | 26.518 |
| 29 | Puerto Rico, USA | Mongoose | BS | RABV | 31.710 | 29.956 |
| 30 | Argentina | Dog | BS | RABV | 30.328 | 30.465 |
| 31 | Texas, USA | Skunk | BS | RABV | 19.979 | 18.899 |
| 32 | Alaska, USA | Fox | BS | RABV | 30.119 | 28.494 |
| 33 | Texas, USA | Fox | BS | RABV | 30.963 | 29.303 |
| 34 | Thailand | Dog | BS | RABV | 26.354 | 24.969 |
| 35 | South Dakota, USA | Skunk | BS | RABV | 32.672 | 31.012 |
| 36 | USA | Laboratory strain | BS | RABV | 36.497 | 36.445 |
| 37 | Gabon | Dog | BS | RABV | 27.304 | 25.406 |
| 38 | Texas, USA | Coyote | BS | RABV | 27.739 | 27.046 |
| 39 | California, USA | Skunk | BS | RABV | 25.387 | 25.036 |
| 40 | Arizona, USA | Fox | BS | RABV | 29.856 | 28.819 |
| 41 | Arizona, USA | Bat-*Eptesicus* spp. | BS | RABV | 19.187 | 18.138 |
| 42 | Washington, USA | Bat-*Eptesicus* spp. | TCS | RABV | 24.808 | 25.394 |
| 43 | Mexico | Dog | TCS | RABV | 26.509 | 24.454 |
| 44 | Washington, USA | Bat-*Eptesicus* spp. | BS | RABV | 20.956 | 19.938 |
| 45 | Alabama, USA | Bat-*Tadarida* spp. | BS | RABV | 33.088 | 30.792 |
| 46 | Arizona, USA | Bat-*Lasiurus* spp. | BS | RABV | 20.186 | 17.338 |
| 47 | Greece * | Red Fox | BS | RABV | 16.859 | 16.239 |
| 48 | France* | Red Fox | BS | RABV | 15.502 | 15.363 |
| 49 | Italy * | Red Fox | BS | RABV | 15.963 | 14.833 |
| 50 | USA * | Laboratory strain | BS | RABV | 16.039 | 13.123 |
| 51 | Thailand | Dog | BS | RABV | 21.387 | 21.522 |
| 52 | Florida, USA | Feline | BS | RABV | 20.403 | 20.296 |
| 53 | Texas, USA | Dog | BS | RABV | 20.205 | 20.470 |
| 54 | California, USA | Bat-*Antrozous* spp. | BS | RABV | 21.599 | 20.024 |
| 55 | Namibia | Lion | BS | RABV | 21.102 | 21.164 |
| 56 | Peru | Dog | BS | RABV | 18.995 | 18.427 |
| 57 | Serbia * | Feline | TCS | RABV | 13.443 | 13.264 |
| 58 | France* | Red Fox | TCS | RABV | 12.039 | 11.788 |
| 59 | Europe * | Laboratory strain | TCS | RABV | 11.039 | 11.687 |
| 60 | Kyrgyzstan | Bat-*Myotis* spp. | TCS | ARAV | 34.127 | 33.961 |
| 61 | Tajikistan | Bat-*Myotis* spp. | TCS | KHUV | 36.589 | 34.605 |
| 62 | South Africa | Bat-*Miniopterus* spp. | TCS | DUVV | 36.803 | ND |
| 63 | South Africa | Bat-*Nycteris* spp. | TCS | DUVV | 30.741 | 31.024 |
| 64 | South Africa | Human | TCS | DUVV | 20.767 | 19.454 |
| 65 | South Africa * | Bat-*Miniopterus* spp. | TCS | DUVV | 16.722 | 15.051 |
| 66 | Australia | Bat-*Pteropus* spp. | TCS | ABLV | 31.025 | 28.786 |
| 67 | Australia | Bat-*Pteropus* spp. | BS | ABLV | 25.515 | 23.952 |
| 68 | Europe | Bat-*Eptesicus* spp. | TCS | EBLV-1 | 30.484 | 30.509 |
| 69 | Denmark | Bat-*Eptesicus* spp. | TCS | EBLV-1 | 26.640 | 26.334 |
| 70 | France * | Bat-*Eptesicus* spp. | TCS | EBLV-1 | 14.772 | 14.729 |
| 71 | Europe | Bat-*Myotis* spp. | TCS | EBLV-2 | 41.142 | 38.847 |
| 72 | United Kingdom * | Bat-*Myotis* spp. | TCS | EBLV-2 | 18.826 | 15.930 |
| 73 | Neitherlands | Bat-*Myotis* spp. | TCS | EBLV-2 | 25.577 | 24.847 |
| 74 | United Kingdom * | Bat-*Myotis* spp. | TCS | EBLV-2 | 16.263 | 17.978 |
| 75 | Russia | Bat-*Murina* spp. | TCS | IRKV | 23.988 | 13.290 |
| 76 | Germany * | Bat-*Myotis* spp. | TCS | BBLV | 20.276 | 19.442 |
| 77 | Zimbabwe | Feline | TCS | MOKV | 35.416 | 27.557 |
| 78 | Cameroon | *Crocidura* | TCS | MOKV | 30.726 | 22.380 |
| 79 | Central African Republic | Lophuromys | TCS | MOKV | 41.764 | 29.034 |
| 80 | South Africa | Feline | BS | MOKV | 30.130 | 20.149 |
| 81 | Nigeria | *Crocidura* | TCS | MOKV | 30.770 | 28.605 |
| 82 | South Africa | Bat-Epomophorous | TCS | LBV | 37.012 | 37.912 |
| 83 | Zimbabwe | Bat-*Nycteris* spp. | TCS | LBV | 26.932 | ND |
| 84 | Central African Republic | Bat-*Nycteris* spp. | TCS | LBV | 22.985 | 22.960 |
| 85 | South Africa | Mongoose | TCS | LBV | 23.723 | 24.441 |
| 86 | Kenya | Bat-Hipposideros | TCS | SHIBV | 18.835 | 17.042 |
| 87 | Russia | Bat-*Miniopterus* spp. | TCS | WCBV | 32.087 | 32.881 |
| 88 | Tanzania | African civet | TCS | IKOV | 43.269 | 20.916 |

All 88 samples (except ND = 5) in the validation panel were tested using both LN34m and LN34 assays in duplicate. Isolate origin represents the geographical location and/or distribution of the respective sample.
Source of the RNA isolation was either TCS (tissue culture supernatant) or BS (brain stem).
The samples in the validation panel can be divided into 3 phylogroups: Phylogroup I includes RABV, ARAV, KHUV, BBLV, DUVV, EBLV-1, EBLV-2, ABLV and IRKV; Phylogroup II includes MOKV, SHIBV and LBV; and Phylogroup III includes IKOV and WCBV.
* Sample that was part of the ANSES (French Agency for Food, Environmental and Occupational Health & Safety) panel.
^The mean Ct value of the samples run by both LN34m and LN34 assays.

Clinical Samples: Human ante-mortem as well as post-mortem samples, and those animal samples that had a history of known human exposure received by the Poxvirus and Rabies Branch for testing during November 2014-November 2015 were defined as clinical samples. A total of 205 clinical samples were included in this study and the details of these samples are included in Table 2.

TABLE 2

Clinical samples included in the study

Table 2A

|  | Human | | Animal | | |
| --- | --- | --- | --- | --- | --- |
|  | Positive | Negative | Positive | Negative | Total |
| Brain | 1 |  | 5 | 164 | 169 |
| Skin Biopsy | 2 | 14 |  |  | 15 |
| Saliva | 4 | 15 |  |  | 21 |
| Cornea | 1 |  |  |  |  |
| Total | 8 | 29 | 5 | 164 | 205 |

Table 2B

|  |  | Lab ID | LN34^ | Beta-actin^ |
| --- | --- | --- | --- | --- |
| Human | Skin | A15-2217 | 37.896 | 20.149 |
|  | Skin | A15-2460 | 32.207 | 19.759 |
|  | Saliva | A15-2218 | 32.376 | 17.307 |
|  | Saliva | A15-0728 | 33.310 | 19.432 |
|  | Saliva | A15-0729 | 35.347 | 21.456 |
|  | Saliva | A15-2461 | 32.747 | 24.4535 |
|  | Brain | A15-0731 | 14.003 | 18.068 |
|  | Cornea | K1 | 33.622 | ND |
| Animal | Brain | A15-2206 | 22.998 | 19.948 |
|  | Brain | A15-0755 | 16.121 | 13.888 |
|  | Brain | A15-1861 | 17.017 | 14.048 |
|  | Brain | A15-2026 | 15.098 | 15.528 |
|  | Brain | A15-2190 | 18.319 | 16.244 |

Table 2C

| Species |  | Lab ID | LN34 | Beta-actin |
| --- | --- | --- | --- | --- |
| Arctic Fox | Brain | A15-2672 | 26.675 | 25.673 |
| Bat | Brain | A15-2678 | 17.787 | 19.149 |
| Arctic Fox | Brain | A16-0742 | 20.100 | 20.617 |
| Arctic Fox | Brain | A16-0743 | 18.553 | 17.896 |
| Bat | Brain | A15-0283 | 14.739 | ND |
| Bat | Brain | A15-0284 | 34.104 | ND |
| Cow | Brain | A15-0287 | 15.965 | ND |
| Bat | Brain | A15-0396 | 16.363 | ND |

TABLE 2-continued

Clinical samples included in the study

| Bat | Brain | A15-0399 | 19.139 | ND |
| --- | --- | --- | --- | --- |
| Bat | Brain | A15-0401 | 17.347 | ND |
| Bat | Brain | A15-0407 | 15.326 | ND |
| Bat | Brain | A15-0409 | 19.500 | ND |
| Bat | Brain | A15-1903 | 14.061 | ND |
| Bat | Brain | A15-1905 | 18.525 | ND |
| Bat | Brain | A15-1907 | 24.119 | ND |
| Bat | Brain | A15-1908 | 30.276 | ND |
| Bat | Brain | A15-1910 | 24.881 | ND |
| Bat | Brain | A15-1912 | 28.720 | ND |

Table 2A: Includes a list of all the clinical samples (both human and animal) tested by the LN34 assay.
Table 2B: Includes Ct values of all the positive samples from both human and animals tested by the LN34 Real-Time RT-PCR assay and β-actin internal control.
Table 2C: Includes Ct values of all the positive animal samples collected from field studies tested by the LN34 Real-Time RT-PCR assay and β-actin internal control.
^The mean Ct value of the samples run by the LN34 Real-Time RT-PCR assay and β-actin internal control.
ND: Sample was not tested by this assay.

Field Samples: A total of 58 field samples were tested using LN34 as well as β-actin real-time RT-PCR assay. These samples were part of the annual surveillance testing (n=40) and supplemented with samples collected by USDA/APHIS/Wildlife services during passive surveillance (n=18). All were deemed unfit for testing by DFA test due to limited tissue and preservation conditions.

All clinical samples were tested for the presence of RABV antigens using the DFA test with fluorescein-isothiocyanate (FITC)-conjugated anti-RABV monoclonal antibody (Fujirubio Diagnostics Inc., Malvern, Pa., USA) (Dean and Atanasiu, "The fluorescent antibody test," In: Meslin F X K M, Koprowski H, editor. Laboratory techniques in rabies. 23. 4th ed. Geneva: World Health Organization monograph series; 1996. p. 88-93). Total RNA was extracted from brain as well as tissue culture supernatant using TRIZOL™ reagent (Invitrogen) according to the manufacturer's instructions.

Reverse transcriptase PCR and sequencing: Reverse transcriptase PCR amplification and sequencing of the N gene were performed as described by Kuzmin et al. (*J Clin Microbiol* 46(4):1451-1461, 2008).

Development of Real-Time RT-PCR

Designing Primers and Probes: The probe of the assay was designed by either modified LNA or by a MGB. The differences between those two probes were compared for their sensitivities and specificities in the validation process. All of the probes and primers contain degenerate nucleotides, which is an IUPAC nucleotide ambiguity code. Table 3 contains a list of the primer and probe modifications.

TABLE 3

Primer and Probe Sequences for the Assay LN34

| Name | Length | Sequences[a] | SEQ ID NO: | Position[b] |
| --- | --- | --- | --- | --- |
| Probe LN34 | 17 | (FAM) AA + C + ACCY + C + T + ACA + A + TGGA (BHQ1) | 1 | 59 - 75 |
| Probe LN34a | 17 | (FAM) AAC + ACCYC + T + ACA + A + TGGA (BHQ1) | 1 | 59 - 75 |
| Probe LN34lago | 17 | (FAM) AA + C + ACTA + C + T + ACA + A + TGGA (BHQ1) | 2 | 59 - 75 |
| Probe LN34m | 17 | (6FAM)-ACACCYCTACAATGGAT-(MGBNFQ) | 3 | 60 - 76 |
| Primer forward1 | 24 | ACGCTTAACAACCAGATCAAAGAA | 4 | 1 - 24 |

TABLE 3-continued

Primer and Probe Sequences for the Assay LN34

| Name | Length | Sequences[a] | SEQ ID NO: | Position[b] |
|---|---|---|---|---|
| Primer forward2 | 25 | ACGCTTAACAACAAAATCADAGAAG | 5 | 1 - 25 |
| Primer reverse | 25 | CMGGGTAYTTRTAYTCATAYTGRTC | 6 | 140 - 164 |

[a]The probes are labeled by fluorescent FAM at the 5' end, BLACK HOLE QUENCHER™ (BHQ1) at the 3' end, except probe LN34m, which is labeled by MGB and nonfluorescent quencher (NFQ). LNA nucleotides are indicated by a "+" preceding the base. Degenerate nucleotides are underlined: D = A, G or T; M = A or C; Y = T or C; R = G or A.
[b]The primer and probe positions are given relative to the full lyssavirus genome (FIG. 1).

LN34, LN34a and LN34Lagos: Probes modified by LNA. The name of the probe is followed by the 5' fluorescent label (in parentheses), probe sequence (a plus preceding the location of the LNA base in the sequence (e.g. +A, +G, +C, +T)), and 3' quencher (Table 3, in parentheses).

LN34Lagos is specific for the Lagos bat virus Nigeria subspecies diagnostics, which is mixed with LN34 in a multiplex format.

LN34m: MGB modified probe with a 5' 6FAM florescent label and a 3' MGB label and NFQ quencher.

The forward primers are a multiplex of two oligos that target the beginning of RABV genome sequences, whereas the reverse primer targets the N gene with 6 degenerate nucleotide modifications.

An artificial positive control for the assay (Hoffmann et al., *J Clin Microbiol* 48(11):3970-8, 2010) was used to minimize potential contamination. oLPC-rabies3-4: GCA CAG GGT ACT TGT ACT CAT ACT GAT CTG AAT CCA TTG TAG AGG TGT TAG AGC ACG ACA GGT TTC CCG ACT GGA TCT TTC TTT GAT CTG GTT AAG CGT TCG CCC TAT AGT GAG TCG TAT TAC A (SEQ ID NO: 7)

A β-actin real-time PCR assay was used in this study as an internal or negative control (Wakeley et al., *Dev Biol* 126:227-236, 2006).
β_actin probe, (TET)-TCC ACC TTC CAG ATG TGG ATC A-(BHQ1) (SEQ ID NO: 8) Forward primer: β_act for: CGATGAAGATCAAGATCATTGC (SEQ ID NO: 9) Reverse primer: β_act rev: AAGCATTTGCGGTGGAC (SEQ ID NO: 10)

Optimization

The reaction conditions were optimized for multiple factors, including annealing temperature, length of reverse transcription and PCR reactions, ratios of primer and probe, and master mix components. The optimized reaction conditions were as follows: Ag-Path ID One-Step RT-PCR Kit (Life Technologies), Assay LN34 primer and probe set, Assay β-actin primer and probe set, artificial positive RNA for assay LN34. One femto gram (about 10,000 copies of the RNA template) was used as positive control. One μl of forward and reverse primer stocks of 10 μM and 1.0 μl of 5 μM probe were used for the 25 μl reaction set up following the directions of the commercial kit.

The cycling conditions were as follows: Reverse transcription at 50° C. for 30 minutes, followed by RT inactivation/initial denaturation at 95° C. for 10 minutes, and amplification step repeated for 45 cycles at 95° C. for 1 second and 56° C. for 20 seconds.

Droplet digital PCR (ddPCR) for the limit of detection of LN34: One-step RT-ddPCR advanced kit (Bio-Rad, CA) was used, which provides improved efficiency and specificity for precise RNA target quantification by ddPCR. Details of the reaction set up and cycling conditions are provided in Example 2.

Similarity Matrix

N gene sequence similarity Matrix analysis: Eighty-eight whole N gene nucleotide sequences (SEQ ID NOS: 31-118) included in the validation panel were subjected for multiple sequence alignments using CLUSTALW. All of the sequences were edited to 1350 bp fragments using BioEdit (Hall, *Nucleic Acids Symposium Series* 41:95-98, 1999).

Example 2: Pan-Rabies Real-Time RT-PCR Assay for Detection of Highly Variable Lyssaviruses Assay LN34 amplifies a 165-nucleotide amplicon including the 58-nucleotide leader sequence, the 12-nucleotide transcription initiation signal, and 95 nucleotides of the nucleoprotein (N) gene (FIG. 1). This leader region and transcription signal sequence are strictly conserved in length among all lyssaviruses (Jackson, *Adv Virus Res* 79:xvii, 2011). The forward primers target the first 25 nucleotides of the leader sequences with a low level of degenerate nucleotides; the reverse primer uses 6 degenerate nucleotides to cover the significant diversity of its targeted sequence. The probe of LN34 targets mostly the transcription initiation signal sequence from position 59 to 75 and utilizes a single degenerate position of pyrimidine (C or T) at position 65. This duplex probe design made the probe sequences match perfectly to all published RABV and other lyssavirus sequences except a few striped skunk RABV variants, MOKV, IKOV, IRKV, and the Nigerian subspecies of LBV. To compensate for the low melting temperature of the 17-nucleotide probe sequences, the probe was modified either by MOB (assay LN34m) or LNA (assay LN34). The melting temperature of the modified probes was calculated using software Primer Express 3.01 for the MOB probe (Life Technology, California) or the Integrated DNA Technologies website (OligoAnalyzer 3.1) for the LNA modified probes. A comparison of LNA modified probes with 5 to 7 LNA nucleotides at different positions of the probe sequences was studied using a number of RABV and other lyssavirus samples. Two formats of the LNA modification, LN34 and LN34a, yielded the overall best results.

The validation panel (n=88) was selected from the CDC RABV repository which includes representative variant samples from around the world (Table 1), including 59 variants of highly divergent RABV isolates from Asia, Africa, Europe, South America and North America. The validation panel also included 13 other lyssavirus species, except LLBV, which is the newest identified lyssavirus species. The assays LN34m and LN34 were able to detect all of the variants from the validation panel except LBV Nigeria subspecies. For the majority of the isolates in the validation panel, assay LN34m and assay LN34 demonstrated similar sensitivity as demonstrated by their similar Ct values (Table 1). The validations of assays LN34m and LN34 were completed separately, which accounts for the Ct value variation for most of the samples in the validation panel. However, for those isolates having sequence variations from the probe sequences, the LN34m and LN34 assays perform considerable differently. The striped Skunk RABV and IRKV have a single nucleotide polymorphism (SNP) at position 69 of the probe sequence (FIG. 1), which reduces the sensitivity of LN34m at least 10 Ct values as compared to that of LN34 for one Texas skunk isolate (Table 1, S. No 12) and one Irkut virus isolate (Table 1 S. No 75). This equates to at least 100-fold differences in the sensitivity. The MGB modified probe is more sensitive to the SNP than the probe modified by LNA. Similarly, MOKV and IKOV have a SNP at position 63 (FIG. 1), which also lead to a Ct value difference of 8-14, also resulting in more than a 100-fold loss in sensitivity for assay LN34m (Table 1, S. No. 75-80 and 88). The Nigeria subspecies of LBV has two SNPs relative to the probe sequences and cannot be detected by either LN34m or LN34. A specific LNA modified probe was synthesized for the Nigerian LBV subspecies and added to the assay LN34; this additional multiplex does not affect the sensitivity and specificity of assay LN34.

The multiplex assay LN34 has overall better sensitivity and specificity. Assay LN34 was able to detect all of the positive samples of the validation panels (n=88) and all of the rabies positive clinical samples confirmed by DFA (n=12), yielding a sensitivity of 100%. Assay LN34 also correctly ruled out about 200 negative clinical samples confirmed by DFA and/or RT-PCR and hemi-nested RT-PCR (n=193), leading to a 100% specificity for this assay. Among those negative samples, many were initially unable to be diagnosed by DFA and were reported as inconclusive due to issues related to the reagent quality. Many of those negative samples produced non-specific amplifications by a conventional RT-PCR assay that was run in parallel with the real-time RT-PCR assays during assay validation. The non-specific amplifications with a similar molecular weight as positive controls from the hemi-nested RT-PCR were ruled out by sequencing the amplicon. These negative samples included skin biopsy (n=14) and saliva (n=15) from patients with neurological symptoms; and DFA-negative or inconclusive animal brain samples (n=164). The positive clinical samples included human ante-mortem samples of skin biopsy (n=2), saliva (n=4), cornea (n=1) and a brain biopsy (Table 2), as well as the animal brain samples. Comparing to the brain samples, the RABV viral load or RNA levels were much lower for the skin biopsy, saliva, and cornea as indicated by the Ct values. The ante-mortem samples with Lab ID A15-0728, A15-0729, and A15-0731 were collected from the same patient and had been stored at room temperature for an extended time due to a transportation delay. Although these samples did not meet the standard for regular DFA test, the results from assay LN34 showed that the brain biopsy had a very high level of viral load. The viral load or viral RNA of all three positive saliva samples of the ante-mortem cases had similar Ct values. The assay LN34 was used to test 58 field samples from US annual surveillance testing and Wildlife services during passive surveillance. Those samples were determined to be unfit to be tested by DFA assay due to limited tissues or unavailable of appropriate conjugates. Eighteen (31.03%) samples were positive (Table 2C).

Two different internal controls were used within the multiplexed assay: (1) detection of a β-actin housekeeping gene assay and (2) a positive control for RNA amplification. The β-actin housekeeping gene assay was adapted from a previous publication with modifications (Wakeley et al., *Dev Biol* 126:227-236, 2006) and used to assess the performance of RNA extraction and has to be positive for the diagnostic results for rabies negative samples (Table 2). The artificial positive controls were also adapted from a previous publication (Hoffmann et al., *J Clin Microbiol* 48(11):3970-8, 2010), with modification to include a short LacZ gene sequence to be used for the identification of the artificial RNA to rule out potential carry-over contamination. The artificially generated RNA positive control can be stored for an extended period by using the stabilization buffer, and can be used as a standard for the comparison of the assay LN34 performance among different laboratories and running conditions. The β-actin assay was labelled by fluorescent HEX and had the same running condition as that of LN34. A diagnostic sample can be run on the sample plate or the same well in a multiplex format. The efficiency of LN34 was estimated to be more than 93% by testing a serial dilution of RNA extracted from RABV strain CVS11. The limit of detection of the LN34 assay was measured by the ddPCR assay using both artificial positive control RNA and a RABV strain ERA. The LN34 assay detected a single copy of RNA for both RNA samples, as detailed below. The results are shown in FIG. 2. The protocol for the ddPCR assay is provided below.

Reaction Setup:
1. The reaction mix for the number of reactions needed was prepared according to the table below:

| Component | Volume per reaction, μl | final concentration |
|---|---|---|
| Supermix | 5 μl | 1X |
| Reverse transcriptase | 2 μl | 20 U/μl |
| 300 mM DTT | 1 μl | 15 mM |
| Target Forward primer 34F 10 μM | 2 μl | 1000 nM |
| Target Reverse primer 34R 10 μM | 2 μl | 1000 nM |
| Target probe 34P 2.5 μM | 1 μl | 125 nM |
| RNase-/DNase-free water | 2 μl | |
| | 15 μl mix them and then add: | variable |
| DNA (different dilution) | 5 μl | |
| Total: | 20 μl | |

2. 20 μl of each reaction mix was mixed thoroughly and loaded into a sample well of a DG8 cartridge for QX100 droplet generator, followed by 70 μl of droplet generator oil for probes into the oil wells. The DG8 cartridge was then put into droplet generator for 2 minutes.

Thermal Cycling Conditions:
3. After droplet generation with the QX100 droplet generator, droplets were transferred into a clean 96-well plate. The plate was heat sealed with foil by the PX1 PCR plate sealer before thermal cycling on an ABI GeneAmp 9700. The ramp rate setting of the thermal cycle was lowered to 3° C./s to allow thorough heating and cooling of the droplets.

4. After PCR, the 96-well plate was placed into a plate holder and loaded into the QX100 droplet digital reader for detection and analysis.

Cycling Conditions:

| Cycling step | temperature, °C. | time | number of cycles |
|---|---|---|---|
| Reverse transcription | 45° C. | 60 min | 1 |
| Enzyme activation | 95° C. | 10 min | 1 |
| Denaturation | 95° C. | 30 sec | 40 |
| Annealing/extension | 55° C. | 1 min | 40 |
| Enzyme deactivation | 98° C. | 10 min | 1 |
| Hold | 4° C. | | |

The N gene sequences of all samples used in the validation panel were sequenced and newly generated sequences were deposited in Genbank (set forth herein as SEQ ID NOS: 31-118). The similarity matrix of the N gene among the validation panel samples was calculated using Mega software (5.1). RABV has a similarity range from 82% or higher in which the lowest identities values are found among RABV in southeastern North America, from the vampire bat of Mexico, raccoon and South Central skunk of the U.S., which agrees with previous RABV variant classifications that suggest American indigenous RABV is one of the most divergent strains (Jackson, *Adv Virus Res* 79:xvii, 2011). The non-RABV lyssaviruses have lower similarity values ranging from 68% to 79%. In comparison, the most diverged lyssavirus was IKOV, which also agrees with previous studies (Arechiga Ceballos et al., *Emerg Infect Dis* 19(5): 793-795, 2013). The LN34 assay's ability to detect all available lyssaviruses confirms its robustness, and highlights its utility as a diagnostic tool applicable for rabies diagnosis.

Diagnostic Applications

Assay LN34 represents a major improvement over previously published real-time RT-PCR assays for rabies and other lyssavirus diagnostics as it can detect a broad range of phylogenetic diversity with superior sensitivity and specificity in a single step reaction. The assay was validated using a large and highly diverse panel containing major RABV variants and 13 other lyssaviruses. The initial assay development used over 280 published full genome sequences of all lyssavirus species except LLBV, and the RABV sequences covered all major geographic based clades, including American indigenous, India, Asia, Africa 2, Africa 3, Arctic-related and cosmopolitan strains. The forward primer sequences of the assay LN34 only needed degenerate nucleotides near the 3' end as the first 9 nucleotides of the forward primers are identical among all lyssaviruses. The reverse primer also targets a relatively conserved region that has been used for the design of rabies PCR primers (Hayman et al., *J Virol Methods* 177(1):87-93, 2011), but the reverse primer of the assay LN34 is longer compared to previous publications and uses a high level of degenerate nucleotides to balance the universal amplification of lyssaviruses alongside specificity for divergent viruses (Hayman et al., *J Virol Methods* 177(1):87-93, 2011). The probe sequence of the assay LN34 targets one of the most conserved regions among all lyssaviruses (Heaton et al., *J Clin Microbiol* 35(11):2762-2766, 1997). The LN34 probe has identity with known RABV when a single degenerate site is accounted for (excluding some striped skunk RABV variants). The low level of degeneration of the probe sequences allows the LN34 assay to maintain an optimal degree of sensitivity and specificity for RABV diagnostics. The validation results demonstrated that the Ct values with all RABV variants were highly positive even when all samples used in the validation cohort were diluted more than 10-fold. The non-RABV lyssaviruses are more diverse compared to RABV, but at least 8 lyssavirus species have a perfect match for the LN34 probe sequences (FIG. 1), and can be amplified efficiently as shown in the validation data (Table 1). Since the LBV Nigeria subspecies cannot be detected by the initial design of the probe, a multiplex format with a specific probe sequence for this subspecies of LBV was developed, and additional specific probes can be used for the detection of any newly identified lyssavirus if needed. Both MGB and LNA modified LN34 probes work well for most lyssaviruses except a few virus strains with variations within the probe sequences (FIG. 1). Previous studies showed that LNA and MGB probes have similar sensitivities (Letertre et al., *Mol Cell Probes* 17(5):227-35, 2003). In the validation studies disclosed herein, the MGB probe was very sensitive to a single nucleotide changes in the probe's target sequence, whereas the LNA probe had a higher tolerance to single nucleotide changes.

The validation results showed that the MGB and LNA probes had similar sensitivities for most of the RABV and lyssavirus strains. For those samples with more than 3 Ct value differences, the samples were re-run on the same plate to confirm such differences. Only RABV isolates from Gabon Africa (Table 1 S. No. 37) and a bat associated RABV from the U.S. (Table 1, S. No. 45 and 46) still had more than 2 Ct value differences, which may be due to the primer targeted sequence variations. Only the newest lyssavirus (LLBV) was not available for the validation of LN34 (Arechiga Ceballos et al., *Emerg Infect Dis* 19(5):793-795, 2013). LLBV is grouped with IKOV phylogenetically (Phylogroup 3).

Each year, rabies surveillance in the United States tests over 100,000 suspected rabid animal samples; over 6,000 rabid animals were diagnosed in 2014 (Monroe et al., *J Am Vet Med Assoc* 248(7):777-788, 2016). The inherent high throughput nature of assay LN34 can improve the speed of the testing and reduce the workload for diagnostic laboratories. For those thousands of samples unfit for DFA testing due to limited sample quantities or sample degradation, assay LN34 can be used as the confirmation test of choice, since it requires very little material for the testing and allows passive surveillance using sample stabilization reagents to preserve rabies suspicious samples. By applying the real-time RT-PCR assay LN34, the number of unsuitable samples for testing can be further reduced, which will improve the surveillance and control of rabid animals in the U.S.

The LN34 assay was able to detect a single copy the RNA template of rabies clinical samples. As the majority of RABV and the other lyssaviruses have identical sequences to that of the LN34 probe, the amplification efficiency and the limit of detection for most lyssavirus species should be maintained relatively constant for LN34, as demonstrated during the validation process. The high sensitivity of LN34 is important for the diagnosis of samples that have been stored or transported under non-optimal conditions and cannot to be diagnosed by other technologies.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

The invention claimed is:

1. A method for detecting lyssavirus nucleic acid in a sample, comprising contacting the sample with (i) at least one forward primer and at least one reverse primer to amplify lyssavirus nucleic acid present in the sample; and (ii) at least one probe that detects the amplified lyssavirus nucleic acid, in a real-time polymerase chain reaction (PCR) assay wherein:
   the at least one forward primer and the at least one reverse primer amplify a 5' region of the lyssavirus genome encompassing a region corresponding to at least nucleotides 59-75 or 60-76 of any one of SEQ ID NOS: 11-30; and
   the at least one probe is no more than 20 nucleotides in length and comprises the nucleotide sequence of SEQ ID NO: 1, SEQ ID NO: 2 or SEQ ID NO: 3, wherein the at least one probe comprises at least one modification to increase melting temperature (Tm).

2. The method of claim 1, wherein the at least one forward primer is no more than 40 nucleotides in length and comprises the nucleotide sequence of SEQ ID NO: 4 or SEQ ID NO: 5.

3. The method of claim 1, wherein the at least one reverse primer is no more than 40 nucleotides in length and comprises the nucleotide sequence of SEQ ID NO: 6.

4. The method of claim 1, comprising contacting the sample with a first forward primer comprising SEQ ID NO: 4, a second forward primer comprising SEQ ID NO: 5, and a reverse primer comprising SEQ ID NO: 6.

5. The method of claim 1, wherein the at least one probe is modified to include at least one locked nucleic acid (LNA) nucleotide.

6. The method of claim 1, wherein the at least one probe is modified to include at least three LNA nucleotides.

7. The method of claim 1, wherein the at least one probe is modified to include at least five LNA nucleotides.

8. The method of claim 1, wherein the at least one probe is modified to include at least seven LNA nucleotides.

9. The method of claim 1, wherein the at least one probe comprises the nucleotide sequence of SEQ ID NO: 1, and wherein the probe comprises LNA nucleotides at positions 4, 9, 10, 13 and 14.

10. The method of claim 9, wherein the probe further comprises LNA nucleotides at positions 3 and 8.

11. The method of claim 1, wherein the at least one probe comprises the nucleotide sequence of SEQ ID NO: 2, and wherein the probe comprises LNA nucleotides at positions 3, 4, 8, 9, 10, 13 and 14.

12. The method of claim 1, wherein the at least one probe is modified to include a minor groove binder (MGB).

13. The method of claim 1, wherein the at least one probe comprises the nucleotide sequence of SEQ ID NO: 3, and wherein the probe comprises a MGB at the 3' terminus.

14. The method of claim 1, comprising contacting the sample with a first forward primer comprising SEQ ID NO: 4, a second forward primer comprising SEQ ID NO: 5, a reverse primer comprising SEQ ID NO: 6, and a first probe comprising:
  SEQ ID NO: 1, wherein positions 4, 9, 10, 13 and 14 are LNA nucleotides;
  SEQ ID NO: 1, wherein positions 3, 4, 8, 9, 10, 13 and 14 are LNA nucleotides; or
  SEQ ID NO: 3, wherein the probe comprises a MGB at the 3' terminus.

15. The method of claim 14, further comprising contacting the sample with a second probe comprising SEQ ID NO: 2, wherein positions 3, 4, 8, 9, 10, 13 and 14 are LNA nucleotides.

16. The method of claim 1, wherein the at least one probe, the first probe, the second probe, or any combination thereof, comprise(s) a 5' fluorescent label and a 3' quencher.

17. A kit for detecting lyssavirus nucleic acid, comprising:
  at least one forward primer and at least one reverse primer capable of amplifying a 5' region of the lyssavirus genome encompassing a region corresponding to at least nucleotides 59-75 or 60-76 of any one of SEQ ID NOS: 11-30; and
  at least one probe that is no more than 20 nucleotides and length and comprises the nucleotide sequence of SEQ ID NO: 1, SEQ ID NO: 2 or SEQ ID NO: 3, wherein the at least one probe comprises at least one modification to increase melting temperature (Tm).

18. The kit of claim 17, wherein the at least one forward primer is no more than 40 nucleotides in length and comprises the nucleotide sequence of SEQ ID NO: 4 or SEQ ID NO: 5.

19. The kit of claim 17, wherein the at least one reverse primer is no more than 40 nucleotides in length and comprises the nucleotide sequence of SEQ ID NO: 6.

20. The kit of claim 17, comprising a first forward primer, a second forward primer and a reverse primer, wherein the first forward primer comprises SEQ ID NO: 4, the second forward primer comprises SEQ ID NO: 5 and the reverse primer comprises SEQ ID NO: 6.

21. The kit of claim 17, wherein the at least one probe is modified to include at least one, at least two, at least three, at least four or at least five locked nucleic acid (LNA) nucleotides.

22. The kit of claim 17, wherein the at least one probe is modified to include a minor groove binder (MGB).

23. The kit of claim 15, wherein the at least one probe is selected from:
  SEQ ID NO: 1, wherein positions 4, 9, 10, 13 and 14 are LNA nucleotides;
  SEQ ID NO: 1, wherein positions 3, 4, 8, 9, 10, 13 and 14 are LNA nucleotides; and
  SEQ ID NO: 3, wherein the probe comprises a MGB at the 3' terminus.

24. The kit of claim 23, further comprising a probe comprising SEQ ID NO: 2, wherein positions 3, 4, 8, 9, 10, 13 and 14 are LNA nucleotides.

25. The kit of claim 23, wherein the at least one probe comprises:
  SEQ ID NO: 1, wherein positions 4, 9, 10, 13 and 14 are LNA nucleotides, or SEQ ID NO: 1, wherein positions 3, 4, 8, 9, 10, 13 and 14 are LNA nucleotides; and
  SEQ ID NO: 2, wherein positions 3, 4, 8, 9, 10, 13 and 14 are LNA nucleotides.

26. The kit of claim 23, wherein the at least one probe comprises:
  SEQ ID NO: 3, wherein the probe comprises a MGB at the 3' terminus; and
  SEQ ID NO: 2, wherein positions 3, 4, 8, 9, 10, 13 and 14 are LNA nucleotides.

27. The kit of claim 17, wherein the at least one probe comprises a heterologous or synthetic label.

28. The method of claim 1, wherein the at least one probe comprises a heterologous or synthetic label.

* * * * *

SEQUENCE LISTING

<160> NUMBER OF SEQ ID NOS: 118

<210> SEQ ID NO 1
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1
aacaccycta caatgga                                                   17

<210> SEQ ID NO 2
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 2
aacactacta caatgga                                                   17

<210> SEQ ID NO 3
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 3
acaccyctac aatggat                                                   17

<210> SEQ ID NO 4
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 4
acgcttaaca accagatcaa agaa                                           24

<210> SEQ ID NO 5
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 5
acgcttaaca acaaaatcad agaag                                          25

<210> SEQ ID NO 6
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 6
cmgggtaytt rtaytcatay tgrtc                                          25

<210> SEQ ID NO 7
<211> LENGTH: 124
<212> TYPE: DNA
<213> ORGANISM: Artificial sequence -continued

```
<220> FEATURE:
<223> OTHER INFORMATION: Synthetic oligonucleotide

<400> SEQUENCE: 7
gcacagggta cttgtactca tactgatctg aatccattgt agaggtgtta gagcacgaca 60
ggtttcccga ctggatcttt ctttgatctg gttaagcgtt cgccctatag tgagtcgtat 120
taca 124

<210> SEQ ID NO 8
<211> LENGTH: 22
<212> TYPE: DNA
<213> ORGANISM: Artificial sequence
<220> FEATURE:
<223> OTHER INFORMATION: Synthetic oligonucleotide
<400> SEQUENCE: 8
tccaccttcc agatgtggat ca 22

<210> SEQ ID NO 9
<211> LENGTH: 22
<212> TYPE: DNA
<213> ORGANISM: Artificial sequence
<220> FEATURE:
<223> OTHER INFORMATION: Synthetic oligonucleotide
<400> SEQUENCE: 9
cgatgaagat caagatcatt gc 22

<210> SEQ ID NO 10
<211> LENGTH: 17
<212> TYPE: DNA
<213> ORGANISM: Artificial sequence
<220> FEATURE:
<223> OTHER INFORMATION: Synthetic oligonucleotide
<400> SEQUENCE: 10
aagcatttgc ggtggac 17

<210> SEQ ID NO 11
<211> LENGTH: 163
<212> TYPE: DNA
<213> ORGANISM: Rabies virus
<400> SEQUENCE: 11
acgcttaacg acaaaatcag agaagaggta gacagtgtcg tttacagagc aaaaatgtaa 60
cacccctaca atggatgccg acaagattgt atttaaagtc aagaatcagg tggtctcctt 120
gaagcctgag atcattgtag accaatatga gtacaagtac ccg 163

<210> SEQ ID NO 12
<211> LENGTH: 163
<212> TYPE: DNA
<213> ORGANISM: Rabies virus
<400> SEQUENCE: 12
acgcttaaca acaaaatcag agaagaagta gacagtgtcg tctacaaagc aaaaatgtaa 60
cacctctaca atggatgccg acaagattgt atttaaagtc aataatcagg tggtttctct 120
gaagcctgaa attatcgtgg atcaatatga gtacaagtac cct 163

<210> SEQ ID NO 13
<211> LENGTH: 163
<212> TYPE: DNA

<213> ORGANISM: Rabies virus

<400> SEQUENCE: 13

```
acgcttaaca acaagatcaa agaagaaata tacagcgtca tttgcaaagc aaaaatgtaa      60
cacctctaca atggatgctg acaggattgt attcagagct aataatcagg tggtctcttt     120
gaggcctgag attatcgcgg atcaatatga gtacaagtac cct                       163
```

<210> SEQ ID NO 14
<211> LENGTH: 163
<212> TYPE: DNA
<213> ORGANISM: Rabies virus

<400> SEQUENCE: 14

```
acgcttaaca acaaaatcag agaagaagca gacagcgtca gttgcaaaac aaaaatgtaa      60
caccccctaca atggatgccg acaagattgt attcaaagtc aataatcagg tggtctcttt    120
gaagcctgag atcatcgtgg atcaatatga gtacaagtac cct                       163
```

<210> SEQ ID NO 15
<211> LENGTH: 163
<212> TYPE: DNA
<213> ORGANISM: Rabies virus

<400> SEQUENCE: 15

```
acgcttaaca acaaaatcag agaagaagca gacaacgtca gttgcaaagc aaaagtgtaa      60
caccccctaaa atggataccg acaagattgt attcaaagtc aataatcatg tggtctcttt    120
gaagcctgag attatcgtgg atcaatatga gtacaagtac cca                       163
```

<210> SEQ ID NO 16
<211> LENGTH: 163
<212> TYPE: DNA
<213> ORGANISM: Rabies virus

<400> SEQUENCE: 16

```
acgcttaaca acaaaatcag agaagaagca gacagcgtca tttgcaaagc aaaaatgtaa      60
caccccctaca atggatgccg acaagattgt attcaaagtc aataatcagg tggtttcctt    120
gaagccagag attattgtgg atcaatatga gtacaaatac cct                       163
```

<210> SEQ ID NO 17
<211> LENGTH: 163
<212> TYPE: DNA
<213> ORGANISM: Australian bat lyssavirus

<400> SEQUENCE: 17

```
acgcttaacg acaaaaccag agaaggagta gacatgatca tttgcgaagc aaaaatgtaa      60
caccccctaca atggattctg ataagattgt ctttaaggtc aacaatcagt tggtgtctgt    120
taagccggag gtgatagtag atcaatatga gtacaaaatat ccc                      163
```

<210> SEQ ID NO 18
<211> LENGTH: 135
<212> TYPE: DNA
<213> ORGANISM: Bokeloh bat lyssavirus

<400> SEQUENCE: 18

```
tagacataat catctacata gcaaaaaggc aacacccccta caatggactc tgacaagatt      60
gtcttcaaag tccataatca gttggtgtct gtaaagccag aggtgattgt tgatcaatat     120
gaatacaagt atccc                                                      135
```

<210> SEQ ID NO 19
<211> LENGTH: 163
<212> TYPE: DNA
<213> ORGANISM: European bat lyssavirus-2

<400> SEQUENCE: 19
acgcttaacg acaaaaccag aaaaggaata gacacaatcg tctgtagagc agaaatgcaa      60
cacccctaca atggatgctg acagaattgt cttcaaagtc cataatcagt tggtgtctgt     120
aaagccagaa gtaattgtag atcaatatga gtacaaatac cct                       163

<210> SEQ ID NO 20
<211> LENGTH: 163
<212> TYPE: DNA
<213> ORGANISM: Khujand virus

<400> SEQUENCE: 20
acgcttaacg acaaaaccag aaaaggaata gacatcatcg cctgtagaat aggaatgtaa 60
cacccctaca atggatgccg acagaattgt ctttaaagtt aagaatcagt tggtgtctgt 120
taagccggag gtgattgttg atcagtacga gtacaaatac ccg 163

<210> SEQ ID NO 21
<211> LENGTH: 163
<212> TYPE: DNA
<213> ORGANISM: Aravan virus

<400> SEQUENCE: 21
acgcttaacg acaaaaacag aaaaggaata gacataatcg cctgcagaat agaaatgtaa 60
cacccctaca atggattctg acaagattgt cttcaaggtc cataaccagt tggtttcagt 120
gaagcctgag gtgattactg atcagtatga gtataagtat cct 163

<210> SEQ ID NO 22
<211> LENGTH: 163
<212> TYPE: DNA
<213> ORGANISM: Duvenhage virus

<400> SEQUENCE: 22
acgcttaaca acaaaatcat aaaaggggca gacatgttca tttgtataac acaaatgtaa 60
cacccctaca atggatgctg aaagaattgt ctttaaggtc cgtaatcagc tagtctctgt 120
aaaaccagag gtcatctctg atcagtatga gtacaaatat cct 163

<210> SEQ ID NO 23
<211> LENGTH: 163
<212> TYPE: DNA
<213> ORGANISM: European bat lyssavirus-1

<400> SEQUENCE: 23
acgcttaaca acaaaaacaa aaaaggggta gacacgttca tcgatagaac agaaatgtaa 60
cacccctaca atggatgtta acaaggttgt gtttaaggtc cataatcagc tggtctcagt 120
aagacctgag gtgatctctg atcagtatga gtataagtac cct 163

<210> SEQ ID NO 24
<211> LENGTH: 163
<212> TYPE: DNA
<213> ORGANISM: Irkut virus

```
<400> SEQUENCE: 24
acgcttaaca acaaaatcac aaaaggggta gacatgttca tctgtagaac agaaatgtaa      60 caccccctaaa atggattctg acagaattgt cttcaaagtt cataaccagc tggtttctct    120
taagccagag gttatctctg atcagtatga atacaaatac cct                       163

<210> SEQ ID NO 25
<211> LENGTH: 163
<212> TYPE: DNA
<213> ORGANISM: Lagos bat virus

<400> SEQUENCE: 25
acgcttaaca gcaaaatcag agaagatata gacagcgaca atgcgctgaa caaaatgtaa     60 caccccctaca atggattctg acaagattgt ttttaaggtt cacaatcaga tcgtatcttt    120
aaagcctgag attatatcag accaatatga atataagtat cca                       163

<210> SEQ ID NO 26
<211> LENGTH: 163
<212> TYPE: DNA
<213> ORGANISM: Lagos bat virus

<400> SEQUENCE: 26
acgcttaaca acaaaatcag agaagacata gacacctaca atgaggtaat caaaatgtaa     60
cactactaca atggattcag aaaggattgt tttcagagtt cataatcagg tagtgtcact    120
caaaccagag attatatcag atcaatatga atataaatat cca                       163

<210> SEQ ID NO 27
<211> LENGTH: 163
<212> TYPE: DNA
<213> ORGANISM: Shimoni bat virus

<400> SEQUENCE: 27
acgcttaaca gcaaagtcag agaagagata agcctctaca atgagcgaat caaaatgtaa     60 caccccctaca atggactctg aaaagattgt tttcaaagtt cgtaaccagg tggtgtcttt    120
gaagccagaa ataatctctg atcagtatga gtacaaatat cct                       163

<210> SEQ ID NO 28
<211> LENGTH: 163
<212> TYPE: DNA
<213> ORGANISM: Mokola virus

<400> SEQUENCE: 28
acgcttaaca acaaaatcaa agaagacata gacagtatca gcgacctaaa caaaatgtaa     60
cactcctaca atggagtctg acaagattgt gttcaaggtg aacaaccaag tcgtttcttt    120
gaagcccgag gtcatatcgg atcaatatga gtataaatat cct                       163

<210> SEQ ID NO 29
<211> LENGTH: 163
<212> TYPE: DNA
<213> ORGANISM: West Caucasian bat virus

<400> SEQUENCE: 29
acgcttaaca acaaaatctt ataaggacga gaaaacctca gagggcaaaa accaatgtaa     60 caccccctaca atggattctg aacacattgt gtttagggtc agaaatgaaa tagtgactct    120
caaacccgaa gtgatatccg accagtatga atataaatat cct                       163
```

<210> SEQ ID NO 30
<211> LENGTH: 163
<212> TYPE: DNA
<213> ORGANISM: Ikoma virus

<400> SEQUENCE: 30
acgcttaaca gctaaaaacc agaagacaga gaaggaatcg aaggggaaaa gaaaaagtaa 60
cacttctaca atggatcctg aacaagtagt tttcaagtct cggaaggaaa ttgtcgtgtt 120
gagaccagag gtgatatcgg atcagtatga atacaaatac cct 163

<210> SEQ ID NO 31
<211> LENGTH: 1350
<212> TYPE: DNA
<213> ORGANISM: Rabies virus

<400> SEQUENCE: 31
atggatgccg acaagattgt gttcaaggtc aataatcagg tggtctcttt gaagcctgag 60
attatagtgg atcaatatga gtacaagtac cctgctatca aggatttgaa gaagcccagt 120
atcactctag ggaaagcccc cgatttgaac aaagcataca agtcagtttt atcaggtttg 180
aatgctgcca agcttgatcc tgatgatgta tgttcctact tagcagctgc aatgcagttc 240
tttgaaggga catgtcccga agattggacc agctacggga tcttgatcgc aagaaaagga 300
gataagatca ccccggattc tcttgtggag ataaagcgta ctgatgtaga ggggaattgg 360
gctttgacgg gaggaatgga attgacgagg gaccccactg ttcctgagca tgcgtcttta 420
gtcggtcttc tcttgagtct gtacaggttg agcaaaatat ctgggcaaaa caccggtaac 480
tataaaacaa atattgcaga caggatagag cagatcttcg agacagcccc ttttattaaa 540
atcgtggaac accatactct gatgacaact cacaaaatgt gcgctaattg gagtactaca 600
ccaaacttca gattcttggc agggacctac gacatgtttt tctcccggat tgagcacctg 660
tattcagcga tcagagtagg cacggtagtc actgcttatg aggactgctc ggggctagtg 720
tcgttcactg ggttcataaa gcagataaat ctcactgcaa gggaggcaat actatatttc 780
ttccacaaga acttcgagga agagataaga agaatgtttg agccggggca agagacagct 840
gttcctcact cctatttcat tcacttccgt tcactgggct tgagtgggaa gtccccttat 900
tcatcaaatg cagttggtca tgtgtttaat ctcattcact ttgttggatg ctacatgggg 960
caagtaaggt ccctgaatgc aacggtcatt gccggatgtg ctcctcatga gatgtctgtt 1020
ttagggggct atttagggga ggagtttttt ggaaagggaa cgttcgaaag gagattcttc 1080
agagacgaaa aagaacttca agaatatgag acggcagaat tgacaaagac tgacgtagcg 1140
ctggcagatg acgggactgt caattcggat gacgaggact acttctccgg tgaaaccaga 1200
agccccgaag ctgtttatgc tcgaatcatg atgaacggag gccgactaaa gagatcgcac 1260
ataagaagat atgtttcagt cagctccaat caccaagctc gtccgaactc gtttgccgag 1320
tttctaaata agacatattc tagtgactca 1350

<210> SEQ ID NO 32
<211> LENGTH: 1350
<212> TYPE: DNA
<213> ORGANISM: Rabies virus

<400> SEQUENCE: 32
atggatgccg acaagattgt gttcaaagtc aataatcagg tggtctcttt gaagcctgag 60
attatcgtgg atcaatatga gtacaagtac cctgccatca aggatttgaa aaagccttgt 120

```
atcacccctag ggaaagcccc cgacttgaac aaagcataca aatcagtttt atcaggcatg      180
aatgccgcca aacttgatcc ggatgatgta tgctcctact tggcagcagc aatgcagttc      240
tttgagggga catgtccgga agactggacc agctatggaa tcctgattgc acgaaaagga      300
gacaggatca ccccaaactc tctagtggag ataaagcgta ctgatgtaga cgggaattgg      360
gctctgacag gaggcatgga attgacaagg accccactg tctctgaaca tgcatcttta      420
gtcggtcttc tcctgagtct gtacaggttg agcaaaatat caggacagaa cactggtaac      480
tataagacaa acattgcaga ttggatagag cagattttcg agacagcacc ttttgttaag      540
atcgtggaac accatacccct aatgacaact cacaagatgt gtgctaactg gagcactata      600
ccgaacttca gattttggc cggaacctac gacatgtttt tctcacggat tgagcatctg      660
tattcggcaa tcagagtggg cacagtcgtc accgcttatg aagactgctc aggactggta      720
tcgtttacag ggttcataaa gcagatcaat ctcaccgcaa gggaagcaat actatatttc      780
ttccacaaga actttgagga agagataaga agaatgttcg agccagggca agagacagct      840
gttcctcact cttatttcat ccacttccgt tcactaggct tgagtgggaa gtctccttat      900
tcatcaaatg cagtcggcca cgtatttaat ctcatccact tgtttggtg ctacatgggt      960 caagtcagat ctctaaatgc gacggttatt gctgcatgtg cccctcatga gatgtctgtt     1020
ctagggggct atttgggaga ggaattcttc ggaaaaggga catttgaaag aaggttcttc     1080
agagacgaga aagaacttca agaatatgag gcggctgaac taacaaagac cgacgtggca     1140
ctggcagatg acgaaccgt caactctgat gacgaggact attttctccgg tgaaaccaga     1200 agtccagaag ctgtctatac tcgaatcatg atgaatggag gtcgactgaa gagatctcat     1260
atacggagat atgtctcagt cagttccaat catcaagccc gtccaaactc attcgccgaa     1320 ttttaaaca agacgtattc gaatgactca                                       1350

<210> SEQ ID NO 33
<211> LENGTH: 1350
<212> TYPE: DNA
<213> ORGANISM: Rabies virus

<400> SEQUENCE: 33
atggatgccg acaagattgt attcaaagtc aataatcaag tggtctcttt gaagcctgag       60
attatcgtgg atcaatatga gtacaagtac cctgctatca agatttgaa aaaccctgt      120 ataaccctag ggaaagctcc cgacctgaac aaggcataca gtcagtttt atcaggcatg      180 aatgccgcca aacttgatcc tgatgatgta tgttcttact tggcagcagc aatgcagttc      240
tttgaaggga cgtgtccaga agactggacc agctatggaa tcttgattgc acggaaagga      300
gacaagatcc cccagattc tctggtagag ataaagcgca ctgatgtgga agggaattgg      360
gccctgacag gaggcatgga actgacaagg gatcccactg tttctgagca tgcatctttg      420
gtaggccttc tcttgagtct gtacaggttg agcaaaatat caggacaaaa caccggcaac      480
tacaagacaa acattgcaga taggatagag cagattttcg agacagcccc ttttgtcaaa      540
atcgtggaac accatactct aatgacaact cacaaaatgt gtgctaattg gagtactata      600
ccaaacttca gattttggc cggaacctac gacatgtttt tttcccggat tgggcatcta      660
tattcagcaa tcagagtggg cacagttgtc actgcttata agactgtcc agggctggta      720 tcatttaccg ggttcataaa gcagatcaat cccactgcaa gagaagcaat actatatttc      780
ttccacaaga actttgagga agagataaga agaatgtttg agccagggca ggaaacagct      840
```

| | |
|---|---|
| gttcctcact cttatttcat ccatttccgt tcactaggct tgagtgggaa gtctccttat | 900 |
| tcatcaaatg ccgttggtca tgtgttcaat ctcattcact tgttggatg ttatatgggt | 960 |
| caagtcagat ccctaaatgc aacggttatt gctgcatgtg ctcctcatga gatgtctgtt | 1020 |
| ttgggggtt atctggggga ggaattcttc ggaaaaggaa catttgaaag aagattcttc | 1080 |
| agagatgaga aagaacttca ggaatacgag gcggctgaat tgacaaagac tgatgtggca | 1140 |
| ctggcagatg atggaactgt caactccgac gacgaggact acttttccgg tgaaactaga | 1200 |
| agtcctgagg ctgtttatac tcgaatcatg atgaatggag gtcgactaaa gagatcgcat | 1260 |
| atacggagat atgtctcggt cagttccaat catcaagccc gtccaaactc attcgccgag | 1320 |
| tttttgaaca agacatattc tagtgactca | 1350 |

<210> SEQ ID NO 34
<211> LENGTH: 1350
<212> TYPE: DNA
<213> ORGANISM: Rabies virus

<400> SEQUENCE: 34

| | |
|---|---|
| atggatgccg acaagattgt attcaaagtc aataatcagg tgctctcttt gaagcctgag | 60 |
| attatcgtgg accaatatga gtacaagtac cctgctatca aagatttgaa aaagccctgt | 120 |
| ataaccctag ggaaagctcc cgacttaaac aaagcataca agtcagtttt atcaggcatg | 180 |
| aatgctgcca actggatcc cgatgatgta tgctcctact ggcagcagc aatgcagttt | 240 |
| tttgaggga catgtccgga agactggacc agctatggaa tcctgattgc aagaaaagga | 300 |
| gacaagatca ctccagactc tctagtggag ataaagcgta ctgatgtaga agggaactgg | 360 |
| gctctgacag gaggcatgga actgacaagg accccacta tctccgagca tgcatcttta | 420 |
| gttggtcttc tcttgagtct gtacaggctg agcaaaatat caggacaaaa cactgtacgc | 480 |
| tttacgacaa acattgcaga taggatagag cagattttcg agacagcccc ttttgttaag | 540 |
| atcgtggagc atcatacct aatgacaact cacaagatgt gcgctaactg gagtactata | 600 |
| ccaaacttca gattttggc cggaacctac gacatgttct tctcacggat tgagcatttg | 660 |
| tattcagcaa tcagagtggg cacagttgtt actgcttatg aagactgctc agggttggta | 720 |
| tcgtttacag ggttcataaa acagatcaat ctcaccgcaa gagaagcaat actatatttc | 780 |
| ttccacaaga attttgagga agagataagg aggatgttcg agccagggca ggagacagct | 840 |
| gttcctcact cttatttcat tcatttccgt tcactaggct tgagtgggaa gtctccttat | 900 |
| tcatcaaatg ctgttggtca tgtgttcaat ctcattcact tgtcggatg ctacatgggt | 960 |
| caagtcagat ctctaaatgc aacggttatt gctgcatgtg cccctcatga gatgtctgtt | 1020 |
| ctaggggtt attgggaga ggagttcttt ggaaaaggaa catttgaaag aagattcttc | 1080 |
| agagatgaga aagaacttca agaatatgag gcggctgaac tgacgaagac tgatgtggca | 1140 |
| ctggcagatg atggaactgt caactccgac gacgaggact acttctccgg tgaaaccagg | 1200 |
| agtccagaag ctgtctatac tagaatcatg atgaatggag gtcgattgaa gagatcacat | 1260 |
| atacggagat atgtcacagt cagttctaat catcaagccc gtccaaactc attcgcagag | 1320 |
| tttctaaaca agacatactc gagtgactca | 1350 |

<210> SEQ ID NO 35
<211> LENGTH: 1350
<212> TYPE: DNA
<213> ORGANISM: Rabies virus

<400> SEQUENCE: 35

```
atggatgccg acaagattgt attcaaagtc aataatcagg tggtctcctt gaagccagag      60
attatcgtgg atcagtatga gtacaaatac ccagctatca aggacttgaa gaaacctagt     120
ataactctag ggaaggctcc tgacctgaat aaagcataca agtcagtcct gtctggcatg     180
aacgctgcca agcttgatcc tgatgatgtg tgttcctact ggcagctgc aatgcaattc      240
tttgagggat catgccctga agactggacc agttatggaa tcttgattgc acgaaaagga     300
gacaagatca ctcctgactc tcttgtagag ataaaacgta ctgatgtaga aggtaattgg     360
gcactgacgg gaggtatgga agtgacgaga acccaccg ttgctgaaca tgcatcttta       420
gttggtcttc tcttgagtct atataggttg agcaaaatat cggggcaaaa cactggcaac     480
tataagacaa acattgcaga caggatagag cagattttg agactgcccc ctttgtaaag      540
atcgtagaac accatactct aatgacaact cacaagatgt gcgctaactg gagtaccatc     600
ccgaacttta gattcttagc tggaacctac gacatgtttt tctctcggat tgagcatttg     660
tactcagcta aagagtggg cacagttgtc actgcttatg aagactgctc agggttggta      720
tcgttcacag ggttcataaa gcaaataaat ctcaccgcga gagaggcaat cctatatttc     780
ttccacaaga actttgagga agaaataaga agaatgttcg aaccagggca agaaactgca     840
gtccctcact cctatttcat ccacttccgc tcattgggcc tgagtggaaa gtctccctat     900
tcatcgaatg cagttggtca tgtgttcaat ctcattcact ttgtcggatg ttatatgggt     960
caggtcaggt ctcttaatgc cacggttatt gccgcttgtg ccccccatga aatgtcagtt    1020
ctcggaggct atttgggaga ggagtttttt ggaaggggga cgtttgaaag acgattcttt    1080
agggacgaga aggaacttca ggagtatgag gcagctgagc tgatgaagac tgacgtagca    1140
ctggcagacg acggaaccgt caattctgat gacgaggatt acttctccgg tgagacgagg    1200
agccctgagg ccgtctatac tcgaatcatg atgaacggag gtcgactaaa gagatcacac    1260
ataaggagat atgttgccgt cagttctaac catcaagccc gcccaaactc atttgccgag    1320
tttctaagca agacatattc aagtgactcg                                     1350
```

<210> SEQ ID NO 36
<211> LENGTH: 1350
<212> TYPE: DNA
<213> ORGANISM: Rabies virus

<400> SEQUENCE: 36

```
atggatgccg acaagattgt attcaaagtc aataatcaag tggtttctct gaagcctgag      60
attatcgtgg atcaatatga gtacaagtac cctgccatca agatttgaa aaagccctgt     120
ataaccctcg ggaaagcccc tgatttaaat aaagcataca atcagttttt atcaggcatg     180
aatgccgcca aacttgatcc ggatgatgta tgttcctatt ggcagcagc aatgcagttc      240
ttcgagggga tatgtccgga agattggacc agctatggga tcctgattgc acgaaaagga     300
gataagatca ccccagattc tctggtggag ataaagcgta ctgatgtaga agggaattgg     360
gctctgacgg gaggtatgga actgacaagg accccactg tctctgagca tgcatcttta     420
gtcggtcttc tcttgagtct atataggttg agcaaaatat caggacaaaa cactggcaac     480
tataagacaa acattgcaga caggatagag cagattttcg agacagcccc tttcgtcaaa     540
atcgtggaac accatactct aatgacaact cacaaaatgt gcgctaactg gagtactaca    600
ccgaacttca gattttggc tggaacctat gacatgtttt tctcccggat tgagcatcta     660
```

| | |
|---|---|
| tattcagcaa tcagagtggg cacagttgtc actgcttatg aagactgttc agggctggta | 720 |
| tcgtttacgg ggttcataaa gcaaatcaat ctcactgcaa gagaagcgat actatatttc | 780 |
| ttccacaaga actttgagga agagataaga agaatgttcg agccaggaca agagacagct | 840 |
| gttcctcact cttatttcat tcacttccgt tcactaggct tgagcgggaa atctccttat | 900 |
| tcatcaaatg ccgttggtca tgtgtttaat ctcattcact ttgttggatg ctatatgggt | 960 |
| caagtcagat ccctaaatgc aacagttatt ggcgcatgtg ctcctcatga gatgtctgtt | 1020 |
| ctcgggggct atctgggaga ggaattcttc gggaaaggaa catttgaaag aagattcttc | 1080 |
| agagatgaga aagaacttca gaatacgag gcggctgaac taacgaagac tgacgtagca | 1140 |
| ctggcagatg atggaactgt caactctgac gacgaggact acttctccgg tgaaaccaga | 1200 |
| agtccggaag ctgtttatac tcgaatcatg atgaatggag gtcgactaaa gagatcgcat | 1260 |
| atacggagat atgtctcagt cagttccaat catcaagctc gtccaaactc attcgccgag | 1320 |
| tttctaaaca agacgtattc gagtgactca | 1350 |

<210> SEQ ID NO 37
<211> LENGTH: 1350
<212> TYPE: DNA
<213> ORGANISM: Rabies virus

<400> SEQUENCE: 37

| | |
|---|---|
| atggatgccg acaagattgt attcaaagtc aataatcagg tggtctcttt gaagcctgag | 60 |
| attatcgtgg accaatatga gtacaaatac cctgctatca agatttgaa aaagccctgt | 120 |
| ataaccctag ggaaagcccc tgatttaaac aaagcataca agtccgtttt atcaggcatg | 180 |
| aatgctgcca aacttgatcc cgatgatgta tgctcctact tggcagcagc aatgcagttc | 240 |
| tttgagggga catgtccaga agactggacc agctatggaa tcctgattgc aagaaaagga | 300 |
| gacaagatca ctccagactc tctagtggag ataaagcgta ctgatgtaga agggaactgg | 360 |
| gctctgacag gaggcatgga actgacaaga gaccccactg tctccgagca tgcatctttg | 420 |
| gttggtctcc tcttgagtct gtacaggctg agcaaaatat caggacaaaa cactggtaac | 480 |
| tataagacaa acattgcaga taggatagag cagattttcg agacagcccc ttttgttaag | 540 |
| atcgtggaac atcataccct aatgacaact cacaagatgt gcgctaattg gagtacgcac | 600 |
| ccaaacttca gagttttggc cggaacctac gacatgtttt tctcacggat tgagcatctg | 660 |
| tattcagcga tcagagtggg cacagttgtc actgcgtatg aagactgctc agggttagta | 720 |
| tcgtttacag ggttcataaa gcagatcaat ctcaccgcaa gagaagcaat actgtatttc | 780 |
| ttccacaaga actttgagga agagataaga aggatgttcg agccagggca ggaaactgct | 840 |
| gtccctcact cttatttcat tcatttccgt tcactaggct tgagtgggaa gtctccttat | 900 |
| tcgtctaatg ccgttggtca tgtgttcaat ctcattcact ttgtcggatg ttatatgggt | 960 |
| caagtcagat ctctaaatgc aacggttatt gctgcatgtg cccctcatga gatgtccgtt | 1020 |
| ctgggaggtt atttgggaga ggaattcttc gggaaaggaa catttgaaag gagattcttc | 1080 |
| agggatgaga aggaacttca gaatatgag gcggctgaac tgacaaagac tgatgtggca | 1140 |
| ctggcagatg atggaactgt caactcagac gacgaagact acttctctgg tgaaaccaga | 1200 |
| agtccagaag ctgtctatac tcgaatcatg atgaatggag gtcgactgaa gagatcgcat | 1260 |
| atacggagat atgtatcagt cagttccaat catcaagctc gtccaaactc attcgcagag | 1320 |
| tttctaaaca agacatattc gagcgactca | 1350 |

<210> SEQ ID NO 38
<211> LENGTH: 1350
<212> TYPE: DNA
<213> ORGANISM: Rabies virus

<400> SEQUENCE: 38
atggatgccg acaagattgt attcaaagtc aataatcagg tggtctcttt gaagcctgag 60
attatcgtgg accaatatga gtacaagtac cctgctatca aagatttgaa aaagccctgt 120
ataaccctag ggaaagctcc cgacttaaac aaagcataca agtcagtttt atcaggcatg 180
aatgctgcca aactggatcc cgatgatgta tgctcctact tggcagcagc aatgcagttt 240
tttgagggga catgtccgga agactggacc agctatggaa tcctgattgc aagaaaagga 300
gacaagatca ctccagactc tctagtggag ataaagcgta ctgatgtaga agggaactgg 360
gctctgacag gaggcatgga actgacaagg gaccccacta tatccgagca tgcatcttta 420
gttggtcttc tcttgagtct gtacaggctg agcaaaatat caggacaaaa cactggtaat 480
tataagacaa acattgcaga taggatagag cagattttcg agacagcccc ttttgttaag 540
atcgtggagc atcataccct aatgacaact cacaagatgt gcgctaattg gagtactata 600
ccaaacttca gatttttggc cggaacctac gacatgttct tctcacggat tgagcatttg 660
tattcagcaa tcagagtggg cacagttgtt actgcttatg aagactgctc agggttggta 720
tcgtttacag ggttcataaa acagatcaat ctcaccgcaa gagaagcaat actatatttc 780
ttccacaaga attttgagga agagataagg aggatgttcg agccagggca ggagacagct 840
gttcctcact cttatttcat tcatttccgt tcactaggct tgagtgggaa gtctccttat 900
tcatcaaatg ctgttggtca tgtgttcaat ctcattcact ttgtcggatg ctacatgggt 960
caagtcagat ctctaaatgc aacggttatt gctgcatgtg cccctcatga gatgtctgtt 1020
ctagggggtt atttgggaga ggagttcttt ggaaaaggaa catttgaaag aagattcttc 1080
agagatgaga aagaacttca agaatatgag gcggctgaac tgacgaagac tgatgtggca 1140
ctggcagatg atggaactgt caactccgac gacgaggact acttctccgg tgaaaccagg 1200
agtccagaag ctgtctatac tagaatcatg atgaatggag gtcgattgaa gagatcacat 1260
atacggagat atgtcacagt cagttctaat catcaagccc gtccaaactc attcgcagag 1320
tttctaaaca agacatactc gagtgactca 1350

<210> SEQ ID NO 39
<211> LENGTH: 1350
<212> TYPE: DNA
<213> ORGANISM: Rabies virus

<400> SEQUENCE: 39
atgagtgctg aaaagattgc cttgaaggtc aatcataatg tggtcacttt gaagcccgag 60
attatcgtgg atcaatatga gtacaaatac cctgctatca aagacctgaa aaagccctgc 120
ataaccctag ggaaagcccc tgacttaaac aaggcataca agtcggtttt atcaggcatg 180
aatgccgcca aacttgatcc tgatgatgta tgctcctatt tggcggctgc aatgcagttc 240
tttgagggaa catgtccaga agattggacc agctatggaa tcctgattgc gcgaaaagga 300
gacaagatca cccctgactc tctagtggag ataaagcgga ctgatgtgga ggggaattgg 360
gctctgacag gaggcatgga attgacaagg gaccccactg tctctgagca cgcatcttta 420
gttggtctcc tcttgagtct gtacaggttg agcaaaatat caggacaaaa caccggcaac 480
tacaagacaa acattgcgga taggatagag cagattttcg agacagcccc ttttgtcaag 540

| | |
|---|---:|
| atcgtggaac accatacect aatgacaact cacaagatgt gcgctaactg gagtacaaca | 600 |
| ccgaacttca gattttggc cggaacctac gacatgttct tctcacggat tgagcatctg | 660 |
| tattcagcca tcagggtggg cacagttgta accgcttatg aagactgctc agggctggta | 720 |
| tcgtttacag ggttcataaa gcatatcaat ctcaccgcga gagaagcaat attatatttc | 780 |
| ttccacaaaa acttcgaaga agagattaga agaatgttcg agccagggca ggagacagct | 840 |
| gttcctcact cttatttcat tcacttccgc tcgctaggct tgagtgggaa gtctccttat | 900 |
| tcatcgaatg ccgttggtca tgttttcaat ctcattcact ttgttggatg ctatatgggt | 960 |
| caagttagat ccctaaatgc aacggttatt gctgcatgtg ccctcatga gatgtctgtt | 1020 |
| ctaggggat atttgggaga ggaattcttc gggaaaggta catttgaaag aaggttcttc | 1080 |
| agagatgaaa aagagcttca agaatatgag gcagctgaac tgacaaagac tgacgtggca | 1140 |
| ctggcagatg atggaactgt caactccgac gacgaggatt atttctccgg tgaggccaga | 1200 |
| agtccagaag ctgtctatgc tcgaatcatg atgaatggag tcggctaaa gagatcgcat | 1260 |
| gtacggagat atgtctcagt cagttccaat catcaagccc gtccgaactc atttgctgag | 1320 |
| tttctaaaca agacgtattc tagtgattca | 1350 |

<210> SEQ ID NO 40
<211> LENGTH: 1350
<212> TYPE: DNA
<213> ORGANISM: Rabies virus

<400> SEQUENCE: 40

| | |
|---|---:|
| atggataccg acaagattgt attcaaagtc aataatcatg tggtctcttt gaagcctgag | 60 |
| attatcgtgg atcaatatga gtacaagtac ccagctatca aggatttgaa gaagccctgt | 120 |
| ataactctgg ggaaagcccc cgacttaaac aaagcataca agtcagtctt atcaggcatg | 180 |
| aatgccgcca aacttgatcc tgatgatgta tgttcttact tggcagcagc aatgcagttt | 240 |
| ttcgaggga catgtccaga agattggacc agctatggaa tcctaatcgc acgaaaagga | 300 |
| gacaagatta ctccagattc tcttgtggag ataaagcgca ctgatgtaga agggaattgg | 360 |
| gccttgacag gaggcatgga actgacaagg gatcccactg tctctgagca tgcgtcttta | 420 |
| gtcggtcttc tcttgagttt gtataggttg agcaaaatat cagggcaaaa caccggtaac | 480 |
| tataagacaa acattgcaga caggatagag cagatctttg agacagcccc ttttgttaag | 540 |
| atcgtggaac accatactct gatgacaact cacaaaatgt gtgctaattg gagtactata | 600 |
| ccgaacttca gatttctggc cggaacatac gacatgtttt tctctcggat tgaacatctg | 660 |
| tattcagcaa tcagagtagg cacagttgtc actgcttatg aagactgctc agggctggta | 720 |
| tcgtttacag ggttcataaa acaaatcaat ctcaccgcaa gagaagcaat actatatttc | 780 |
| ttccacaaga actttgagga agagataaaa aggatgttcg agccagggca ggagacagct | 840 |
| gtcccgcact cttatttcat tcacttccgt tcactaggct tgagtgggga atctccttac | 900 |
| tcatcaaatg ccgtcggtca tgtgttcaat ctcattcact ttgtcggatg ctatatgggt | 960 |
| caggtcagat ctctaaatgc aacggttatt gctgcatgtg ctcctcatga gatgtctgtt | 1020 |
| ctaggggct atctgggaga ggaattcttc gggaaaggga catttgaaag aagattcttc | 1080 |
| agagatgaga aagaactcca agagcacgag gcggctgaac tgacaaagat tgacgtggcg | 1140 |
| ctggcagatg atggaactgt caactccgac gacgaagact acttttccgg tgaaaccaga | 1200 |
| agtccagaag ctgtgtatac tcgaatcatg atgaatggag tcgactcaa gagatcgcat | 1260 |

| | | |
|---|---|---|
| atacggagat atgtctcagt cagttccaat catcaagctc gtccaaattc attcgccgag | 1320 |
| tttctgaaca agacgtattc gagtgactca | 1350 |

<210> SEQ ID NO 41
<211> LENGTH: 1350
<212> TYPE: DNA
<213> ORGANISM: Rabies virus

<400> SEQUENCE: 41

| | | |
|---|---|---|
| atggatgccg acaagattgt gttcaaagtc aataatcagg tggtctcttt gaagcctgaa | 60 |
| attatcgtgg atcaatatga atacaagtac cctgcaatca agatttgaa aaagccttgt | 120 |
| ataaccctag ggaaggcccc cgacttaaac aaagcataca atcagttttt atcaggcatg | 180 |
| aatgccgcca acttgatccc tgatgatgta tgctccctac tggcagcagc aatgcagttc | 240 |
| tttgagggta catgtccgga agactggacc agctatggaa tcctgattgc acgaaaagga | 300 |
| gacaagatca ctccagactc tctagtggag ataaaagcgta cggatgtaga aggaaattgg | 360 |
| gctctgacag gaggtatgga attgacaagg accccactg tctctgaaca tgcatcttta | 420 |
| gtcggccttc tcctaagtct gtacagattg agcaaaatat caggacagaa cactggtaac | 480 |
| tataagacga acattgcgga taggatagag cagatttcg agacagcccc tttgttaag | 540 |
| atcgtggaac accacaccct aatgacaact cacaagatgt cgctaactg gagtagaaca | 600 |
| ccgaatttca gatttttggc cggaacctac gacatgttct tctcacggat tgagcatctg | 660 |
| tattcggcaa tcagagtggg cacagttgtc accgcttatg aagactgctc aggactggta | 720 |
| tcgtttacag ggttcataag gcagatcaat ctcactgcaa gagaagcaat actatatttc | 780 |
| ttccacaaaa actttgaaga agagataaga gaatgttcg agccagggca agagacagcc | 840 |
| gttcctcact cttatttcat tcacttccgt tcgctaggct tgagtgggaa gtctccctat | 900 |
| tcatcaaatg ccgtcggtca tgtgttcaat ctcattcact tgttggatg ctatatgggt | 960 |
| caagtcagat ccctaaatgc aacggttatt gctgcatgtg cccctcatga gatgtctgtt | 1020 |
| ttaggggct atttgggaga ggaattcttt ggaaaaggga catttgaaag aaggttcttc | 1080 |
| agagatgaga aagaacttca agaatatgag gcggctgaac tgacaaagac tgacgtggca | 1140 |
| ctggcagatg acggaaccgt caattccgat gacgaggact acttctccgg tgaaaccaga | 1200 |
| agtccagaag ctgtctatac tcgaatcatg atgaatggag gtcgactgaa gagatcgcat | 1260 |
| atacggagat atgtctcagt cagttccaat catcaagccc gtccaaactc atttgccgaa | 1320 |
| ttttaaaca agacgtattc aagtgactca | 1350 |

<210> SEQ ID NO 42
<211> LENGTH: 1350
<212> TYPE: DNA
<213> ORGANISM: Rabies virus

<400> SEQUENCE: 42

| | | |
|---|---|---|
| atggataccg acaagattgt attcaaagtc aaaaatcagg ttgtctcctt gaagcctgaa | 60 |
| atcatcgtag atcaatatga atacaagtac ccggctataa agacttaaa gaagccctgt | 120 |
| ataacattgg gaaagccccc tgacctgaac aaggcataca gtcgattttt atccggcatg | 180 |
| aatgcagcta agctagaccc ggatgatgtg tgttcttatt tggcagctgc aatgcaattc | 240 |
| tttgaaggga catgtcctga agactggact agctatgaaa tcttgattgc aaggaaggga | 300 |
| gataagatca ctccaaactc tcttgtagac ataaaacgta ctgacgtaga agggaactgg | 360 |

| | |
|---|---:|
| gctctgacag ggggcctgga attgactagg gatcccacca tttcagaaca tgcatctttg | 420 |
| gtcggtcttc tcctgagtct gtatagactt agcaaaatat ctggacaaaa caccggcaat | 480 |
| tacaagacaa acattgccga tcgtatagaa cagattttg agacggcccc ctttgtgaag | 540 |
| atcgtagaac atcatactct gatgacaact cacaagatgt gcgctaactg gagcaccata | 600 |
| ccgaacttca gattcttagc cggaacttac gacatgtttt tctctcggat tgaacatctg | 660 |
| tactcagcaa taagagtggg tacagttgtc actgcttatg aagattgctc cgggttagtg | 720 |
| tcgtttactg ggtttataaa acagataaat ctcactgcta gggaagcaat cctttatttc | 780 |
| ttccacaaga attttgagga agagataaga agaatgtttg agccaggaca agaaactgca | 840 |
| gttcctcact cctatttcat ccattttcgg tctttgggcc tgagtgggaa atctccatat | 900 |
| tcgtcaaatg cagtgggtca cgtgttcaac ctaattcact tgttggatg ctacatgggt | 960 |
| caagtcagat ctctaaatgc gacggttatt gctgcatgtg cccctcatga gatgtctgtt | 1020 |
| ctagggggct atttgggaga ggaattcttc ggaaaaggga catttgaaag aaggttcttc | 1080 |
| agagacgaga aagaacttca agaatatgag gcggctgaac taacaaagac cgacgtggca | 1140 |
| ctggcagatg acggaaccgt caactctgat gacgaggact atttctccgg tgaaaccaga | 1200 |
| agtccagaag ctgtctatac tcgaatcatg atgaatgag gtcgactgaa gagatatcat | 1260 |
| atacggagat atgtctcagt cagttccaat catcaagccc gtccaaactc attcgccgaa | 1320 |
| tttttaaaca agacgtattc gaatgactca | 1350 |

<210> SEQ ID NO 43
<211> LENGTH: 1350
<212> TYPE: DNA
<213> ORGANISM: Rabies virus

<400> SEQUENCE: 43

| | |
|---|---:|
| atggatgccg ataagattgt attcaaagtc aataatcagg tggtctcctt gaagcccgag | 60 |
| attattgtag atcagtatga gtacaagtac ccggctatca aggacctgaa gaaacccagc | 120 |
| ataacccctag ggaaagctcc tgacctaaac aaagcataca gtctgtctt atcgggcatg | 180 |
| aatgctgcca agcttgatcc tgatgatgtg tgctcctatt tggcagctgc aatgcagctt | 240 |
| ttcgagggat cctgtccgga agactggacc agctacggaa tcctgattgc acgaaaaggg | 300 |
| gacaagatca ctccagattc tcttgtggag ataaaacgta ctgatgtaga ggggaattgg | 360 |
| gctctgacag gaggaatgga gttgacgagg accccactg tttctgagca tgcatcttta | 420 |
| gttggtcttc ttttgagtct gtatcggctg agcaaaatat cggggcagaa caccggcaac | 480 |
| tacaaaacaa acattgcaga taggatagag caaattttcg agacagcccc tttcgtcaag | 540 |
| atcgtggaac accacacttt aatgacaact cacaagatgt gtgctaactg gagtaccata | 600 |
| ccgaacttca gattcttggc tggaacctac gacatgtttt tctcccggat tgagcatcta | 660 |
| tattcagcga ttagagtagg cacagttgtc actgcttatg aagactgctc agggctggta | 720 |
| tcgtttacag ggttcataaa gcaaataaat cttactgcga gagaagcgat actgtatttc | 780 |
| ttccacaaga actttgagga ggagataagg agaatgtttg agccaggtca ggagaccgcc | 840 |
| gttcctcact cttatttcat ccactttcgt tcattgggct gagcgggaa gtccccgtat | 900 |
| tcatcaaatg cagtcggcca cgtgtttaat ctcatccact tgttggatg ttatatgggt | 960 |
| caagtcaggt ctcttaatgc aacggttatt gctgcatgcg ctcctcatga gatgtctgtt | 1020 |
| cttgggggat atttggggga ggagttttt ggaaaaggga cattcgaaag aagattcttc | 1080 |
| agagatgaga aagaactcca agaatacgag gcagctgaat tgactaagac tgacattgct | 1140 |

-continued

| | |
|---|---|
| ttggctgatg acggaaccgt taactctgat gatgaggatt acttctctgg tgaaaccagg | 1200 |
| agtcctgaag ctgtttatac tcggatcatg atgaatggag gccgattaaa aagatcacac | 1260 |
| atcaggagat atgtttcagt cagttccaat catcaagccc gcccaaactc attcgctgag | 1320 |
| tttctaaaca agacatactc taacgactca | 1350 |

<210> SEQ ID NO 44
<211> LENGTH: 1350
<212> TYPE: DNA
<213> ORGANISM: Rabies virus

<400> SEQUENCE: 44

| | |
|---|---|
| atggataccg acaaaattgt attcaaagtc aataatcagg ttgtctctct aaaacctgaa | 60 |
| attattgtag atcaatatga gtacaaatac ccggcgatca aagacttaaa aaagcccagt | 120 |
| atctccctgg gaaaggctcc tgatttgaac aaggcgtata agtcaatttt gtccggcatg | 180 |
| aatgcagcta agctcgaccc tgatgatgtg tgctcttact tggcagctgc aatgcaattc | 240 |
| tttgaaggaa catgtccaga agactggact agctatggaa tcttgattgc aaggaaagga | 300 |
| gacaagataa ctccaaactc tctcgtagac ataaaacgta cagatgtaga agggaactgg | 360 |
| gctctaacag gaggaatgga gttgactagg gatcccacca ttccagaaca tgcatctttg | 420 |
| gttggtcttc tcttgagttt gtatcgattg agcaaaatat ccggacagaa cacaggcaat | 480 |
| tacaagacaa atatctctga tcgtatagaa cagattttg agacggcccc ctttgttaag | 540 |
| atagtggaac atcacacttt aatgacaact cacaaaatgt gcgctaactg gagcaccata | 600 |
| ccgaacttta gattcctggc cggaacttat gacatgtttt ctctcggat gaacatttta | 660 |
| tattcagcaa tcagagtggg tacagttgtc actgcttacg aggactgctc agggctggta | 720 |
| tcgtttacag ggtttatcaa gcagataaac cttacagcaa aggaagcaat actttatttc | 780 |
| ttccacaaga atttgaggg agagataaga agaatgtttg agccgggaca ggaaactgca | 840 |
| gtccctcact cctatttcat ccatttccgg tctttaggcc tgagtgggaa atctccatat | 900 |
| tcgtcaagtg cagttggtca cgtgttcaac ctcattcact tgttggatg ctatatgggt | 960 |
| caagtgaggt ctttgaatgc aacggttatt gccacatgtg ctccacatga atgtctgtt | 1020 |
| ctcgggggtt atttggggga ggagttcttt ggcaaggga cttttgagag aagattcttc | 1080 |
| agggatgaga aggaacttca ggattatgaa gcagcagagt tgacaaagac tgaggtcgct | 1140 |
| ctggcagacg acggaacagt caattctgac gacgaagact acttctctgg tgaaaccagg | 1200 |
| agtccagagg cggtctatac tcggatcatg atcaatgggg gccgactcaa aagatcacat | 1260 |
| ataagaaggt atgtatcagt cagttccaat catcaagctc gccctaattc atttgctgaa | 1320 |
| tttctaaaca agacatattc taacgatcca | 1350 |

<210> SEQ ID NO 45
<211> LENGTH: 1350
<212> TYPE: DNA
<213> ORGANISM: Rabies virus

<400> SEQUENCE: 45

| | |
|---|---|
| atggatgccg acaaaattgt attcaaagtc aataatcagg tggtctcgtt gaagcctgag | 60 |
| attatcgtgg atcaatatga atacaagtac cctgccatca agatttgaa gaagccctgt | 120 |
| ataacactag ggaaagcacc cgacctgaac aaagcgtaca atcggtttt atcaggcatg | 180 |
| aatgccgcca aacttgatcc tgatgatgta tgttcctatt tggcagcagc gatgcagttc | 240 |

-continued

```
tttgagggga cgtgtccgga agattggacc agctatggaa tcctgattgc acgaaaagga    300
gataagatca ccccagattc tctggtggag ataaagcgta ctgatataga agggaactgg    360
gctctgacgg gaggcatgga gctgacaagg gaccccactg tccccgagca tgcatcttta    420
gttggtcttc ttttgagtct gtataggtta agctacgctt cccgacaaaa cactggtaac    480
tataaaacga acattgcaga cagaatacag cagatttttg agacagctcc ttttgttaaa    540
gtcgtggaac accatacact aataccatct cacaatatgt gcgctaattg gagtactata    600
ccgaacttca gatttttggc tggaacctac gacatgtttt tctcccggat tgagcatcta    660
tattcagcaa tcagagtggg cacagttgtt actgcttatg aagactgttc aggtctggta    720
tcgtttacgg ggttcataaa gcaaatcaat ctcaccgcga gagaggcgat actatacttc    780
ttccacaaga attttgaaga ggagataaga agaatgttcg agccggggca agagacagct    840
gttccccact cttatttcat tcacttccgt tcactaggct tgagtgggaa atctccttat    900
tcatcaaatg ccgttggtca tgttttcaac ctcattcact ttgttggatg ttatatgggg    960
caagtcagat ccctcaatgc aacagttatt gccgcatgtg ctcctcatga gatgtctgtt   1020
ttagggggat atctgggaga ggaattcttc gggaaaggaa catttgaaag aagattcttc   1080
agagatgaga aagaacttca agaatatgaa gcggctgaac taacaaaaac tgacatagca   1140
ctggcagatg acggaactgt caactctgat gacgaggact acttctccgg tgaaaccaga   1200
agtcctgaag ctgtttatac tcgaatcatg atgaatggag gtcgactaaa gagatcgcat   1260
atacggagat atgtctcagt cagttccaat catcaagccc gtccaaattc atttgccgag   1320
tttctgaaca agacgtactc gagtgactca                                    1350
```

```
<210> SEQ ID NO 46
<211> LENGTH: 1350
<212> TYPE: DNA
<213> ORGANISM: Rabies virus

<400> SEQUENCE: 46
atggatgccg acaagattgt attcaaagtt aataaccagg tggtctcttt gaagcctgag     60
attatcgtgg atcaatatga atacaagtac cctgctatca aagatttgaa gaagccctgt    120
ataaccctag ggaaagcccc cgacttaaac aaagcataca aatcagtttt gtcaggcatg    180
aatgctgcca aactggatcc cgatgatgta tgttcctacc tggcagcagc aatgcagttc    240
tttgagggga catgcccgga agactggacc agctatggaa tcctgattgc acgaaaagga    300
gacaagatca ccccagattc cctggtggaa ataaagcgta ctgatgtaga agggaattgg    360
gctcttacag gaggcatgga actgacaagg gaccccactg tctctgaaca tgcatcttta    420
gtaggtcttc tcctgagtct gtataggttg agcaagatat caggacagaa caccggtaac    480
tataaaacaa acattgcaga taggatagag ctgattttcg agactgcccc ttttattaag    540
atcgtggagc accatactct aatgacaact cacaaaatgt gcgctaactg gagtactata    600
ccgaatttca gattcttggc cggaacctat gacatgtttt tctcccggat tgagcatcta    660
tattcagcaa tcagagtggg cacagttgtt actgcttatg aagactgttc agggctggta    720
tcgtttactg ggttcataaa gcagatcaat ctcactgcaa gagaagcaat actatacttc    780
ttccataaga actttgagga agagataaga agaatgttcg agccagggca ggagacagct    840
gttcctcact cttatttcat tcatttccgc tcactaggct tgagtgggaa gtctccttat    900
tcatcaaatg ctgtcggtca tgtgttcaat ctcattcact ttgttggatg ctatatgggt    960
caagtcagat ccctgaatgc aacagttatt gcatcatgtg ctcctcatga gatgtctgtt   1020
```

| | |
|---|---|
| ttagggggct atctgggaga ggaattcttc gggaaaggga catttgaaag aagattcttc | 1080 |
| agagatgaga aagaacttca agaatacgag gcggctgaac tgacgaagac tgacgtggca | 1140 |
| ttggcagatg atggaactgt caactctgat gacgaggact acttctccgg tgaaaccaga | 1200 |
| agtccggaag ctgtttatac tcgaatcatg atgaacggag tcgactaaa aagatcgcat | 1260 |
| atacggagat atgtctcagt cagttccaat catcaagccc gtccaaactc attcgccgag | 1320 |
| tttctaaaca agacatattc gagtgactca | 1350 |

<210> SEQ ID NO 47
<211> LENGTH: 1350
<212> TYPE: DNA
<213> ORGANISM: Rabies virus

<400> SEQUENCE: 47

| | |
|---|---|
| atggatgccg ataagattgt attcaaagtc aataatcagg tggtctcttt gaagcctgag | 60 |
| attatcgtgg atcaatatga gtacaagtac cctgctatca aggacttgaa gaagcccagt | 120 |
| attaccctag ggaaagcccc cgatttgaac aaagcataca agtcagtttt atcaggtttg | 180 |
| aatgctgcca agcttgatcc tgatgatgta tgttcctact tagcagctgc gatgcagttc | 240 |
| tttgaaggga catgtcctga agactggacc agctacggga tcttgatcgc aagaaaagga | 300 |
| gataagatta ccccagattc tcttgtggag ataaagcgta ctgatgtaga agggaattgg | 360 |
| gctttgacgg gaggaatgga actgacgagg accccactg ttcccgagca tgcgtcttta | 420 |
| gtcggtcttc tcttgagtct gtacaggctg agcaaaatat ctgggcaaaa cacaggtaac | 480 |
| tataaaacaa atattgcaga taggatagag cagatcttcg agacagcccc ttttattaaa | 540 |
| atcgtggaac accatactct gatgacaact cacaaaatgt gtgccaattg gagtactata | 600 |
| ccaaacttca gattcctggc agggacctac gacatgtttt tctcccggat tgagcacctg | 660 |
| tattcagcga tcagagtagg cacggtagtc actgcttatg aggactgctc ggggctggtg | 720 |
| tcgtttactg ggttcataaa gcagataaat ctcactgcaa gggaagcaat attatatttc | 780 |
| ttccacaaaa acttcgagga ggagataaga agaatgtttg agcccgggca agagacagct | 840 |
| gttcctcact cctatttcat tcactttcgt tccctgggct tgagtgggaa gtcccccttat | 900 |
| tcatcaaatg cagttggtca tgtgttcaat ctcattcact tgttggatg ctacatgggg | 960 |
| caagtaaggt ccctgaatgc aacggtcatt gctggatgtg ctccccgtga atgtctgtt | 1020 |
| ttaggggct atctgggaga ggaattcttc gggaaaggga catttgaaag aagattcttc | 1080 |
| agagatgaga aagaacttcca agagcacgag gcggctgaac tgacaaagat tgacgtggcg | 1140 |
| ctggcagatg atggaactgt caactccgac gacgaagact acttttccgg tgaaaccaga | 1200 |
| agtccagaag ctgtgtatac tcgaatcatg atgaatggag tcgactcaa gagatcgcat | 1260 |
| atacggagat atgtctcagt cagttccaat catcaagctc gtccaaattc attcgccgag | 1320 |
| tttctgaaca agacgtattc gagtgactca | 1350 |

<210> SEQ ID NO 48
<211> LENGTH: 1350
<212> TYPE: DNA
<213> ORGANISM: Rabies virus

<400> SEQUENCE: 48

| | |
|---|---|
| atggatgccg acaagattgt attcaaagtc aataatcaag tggtttcctt gaagcccgag | 60 |
| atcattgtag atcaatatga gtacaagtac ccggctatca aagacctgaa gaaacccagc | 120 |

| | |
|---|---|
| ataacattgg gaaaggctcc tgacctaaac aaagcataca agtctgtatt gtctggcatg | 180 |
| aatgctgcca agcttgatcc agatgatgtg tgctcctatt ggcagctgc aatgcagttt | 240 |
| ttcgagggat cctgtcctga agattggacc agctacggga tcctgattgc acgaaaagga | 300 |
| gataagatca ctccagattc tcttgtagaa ataaaacgta ctgatgtaga ggggaattgg | 360 |
| gctctgacag gaggaatgga gttaacgagg accccactg tttcagagca tgcatcttta | 420 |
| gtcggtcttc tcttgagtct atatcggttg agcaaaatat cggggcaaaa cactggtaac | 480 |
| tacaagacaa acattgcaga taggatagag caaattttcg agacagcccc tttcgtcaag | 540 |
| atcgtggaac atcacacttt aatgacaact cacaagatgt gtgctaattg gagtaccata | 600 |
| ccaaacttca gattcttggc tggaacatac gacatgtttt tctcccggat tgagcatcta | 660 |
| tattcagcga ttagagtagg cacagttgtc actgcttatg aagactgctc agggctggta | 720 |
| tcgtttacag ggttcataaa gcaaataaat ctgactgcga gagaagcgat actgtatttc | 780 |
| ttccacaaga actttgagga ggagataag agaatgtttg agccaggtca ggagaccgcc | 840 |
| gttcctcatt cctatttcat tcactttcgc tcattgggct tgagcgggaa gtccccttat | 900 |
| tcatcaaatg cagtcggcca cgtatttaat ctcatacact ttgttggatg ttatatgggt | 960 |
| caagtcaggt ctcttaatgc aactgttatt gctacgtgcg ctcctcatga gatgtctgtc | 1020 |
| cttggggat atttgggaga ggagtttttt ggaaaaggga catttgaaag aagattcttc | 1080 |
| agggatgaga agaacttca gaatacgag gcggctgagt tgaccaagac tgacattgct | 1140 |
| ttggctgatg acggaaccgt caattctgat gatgaggatt acttctcagg tgaaacccgg | 1200 |
| agtcctgaag ctgtttatac tcggatcatg atgaacggag ccgactaaa agatcacac | 1260 |
| ataaggagat atgtctcagt cagttccaat catcaagctc gcccaaactc attcgccgag | 1320 |
| tttctaaaca agacatactc taatgactca | 1350 |

<210> SEQ ID NO 49
<211> LENGTH: 1350
<212> TYPE: DNA
<213> ORGANISM: Rabies virus

<400> SEQUENCE: 49

| | |
|---|---|
| atggattccg acaagattgt gttccaaggt cataatcagg tggtctcttt gaagcctgag | 60 |
| attatcgtgg atcaatatga ggacaagttc cctgccatca aggatttgaa aaaggcctgt | 120 |
| aatcacctag ggaaagctcc cgacttgaac aaagcataca aatcagtttt atcaggcatg | 180 |
| aatgccgccc aacttgatcg ggatgatgta tgctcctact ggcagcagc aatgcagttc | 240 |
| tttgaggga catgtccgga agactggacc agctatggaa tcctgattgc acgaaaagga | 300 |
| gacaggatca ccccaaactc tctagtggag ataaagcgta ctgatgtaga cgggaattgg | 360 |
| gctctgacag gaggcatgga attgacaagg daccccactg tctctgaaca tgcatcttta | 420 |
| gtcggtcttc tcctgagtct gtacaggttg agcaaaatat caggacagaa cactggtaac | 480 |
| tataagacaa acattgcaga taggatagag cagattttcg acagcacc ttttgttaag | 540 |
| atcgtggaac accataccct aatgacaact cacaagatgt gtgctaattg gagtactata | 600 |
| ccgaacttca gattttggc cggaacctac gacatgtttt tctcacggat tgagcatctg | 660 |
| tattcggcaa tcagagtggg cacagtcgtc accgcttatg aagactgctc aggactggta | 720 |
| tcgtttacag ggttcataaa gcagatcaat ctccccgcaa gggaagcaat actatatttc | 780 |
| ttccacaaga actttgagga agagataaga gaatgttcg agccagggca agagacagct | 840 |
| gttcctcact cttatttcat ccacttccgt tcactaggct tgagtgggaa gtctccttat | 900 |

```
tcatcgaatg ctgtcggtca tgtgttcaat ctcattcact tgttggatg ctacatgggt      960 caagtcagat ctctaaatgc gacggttatt gctgcatgtg cccctcatga gatgtctgtt     1020 ctaggggct atttgggaga ggaattcttc ggaaaaggga catttgaaag aaggttcttc     1080
agagacgaga aagaacttca agaatatgag gcggctgaac taacaaagac cgacgtggca    1140
ctggcagatg acggaaccgt caactctgat gacgaggact atttctccgg tgaaaccaga    1200
agtccagaag ctgtctatac tcgaatcatg atgaatggag tcgactgaa gagatctcat     1260 atacggagat atgtctcagt cagttccaat catcaagccc gtccaaactc attcgccgaa    1320
tttttaaaca agacgtattc gaatgactca                                     1350
```

<210> SEQ ID NO 50
<211> LENGTH: 1350
<212> TYPE: DNA
<213> ORGANISM: Rabies virus

<400> SEQUENCE: 50

```
atggatgccg acaagattgt attcaaagtc aataatcaag tggtttcctt gaagcccgag       60
atcattgtag accagtatga gtacaagtac ccggctatca aagacctgaa gaaacccagt      120
ataaccttag ggaaggctcc tgacctaaac aaagcataca gtctgttttt gtcgggcatg      180
aatgctgcca acttgatccc agatgatgtg tgctccctatt tggcagctgc aatgcagttt      240
ttcgagggat cctgtcctga ggactggacc agctacggga tcctgattgc acgaaaagga     300
gacaagatca ctccagattc tcttgtggat ataaaacgta ctgatgtaga gggaagttgg     360
gccctgacag gaggaatgga gttaacgaga gaccccactg tctccgagca tgcatcttta    420
gttggtcttc tcttgagtct gtatcggttg agcaaaatat cggggcaaaa cactggcaac    480
tacaagacaa acattgcaga taggatagag cagattttcg acacagcccc tttcgtcaag    540
atcgtggaac atcacacttt aatgacaact cacaagatgt gcgcaaactg gagtaccata    600
ccaaacttca gattcttggc tggaacctac gacatgtttt tctcccggat tgagcatcta    660
tattcagcga ttagagtagg cacagtcgtt actgcttatg aagactgctc agggctggta    720
tcgtttacag ggttcataaa gcaaataaat ctcaccgcga gagaagcgat actgtatttc    780
tttcacaaga actttgagga ggagataaga gaatgtttg agcccgggtca ggagaccgcc    840 gttcctcatt cctatttcat tcactttcgc tcattgggct tgagtgggaa gtctccgtat    900
tcatcaaatg cagtcggcca cgtatttaat ctcatccact tgttggatg ttatatgggt     960 caagtcaggt ctcttaatgc aacggttatc gctgcgtgtg cccctcatga gatgtctgtt     1020 cttgggggt atttggggga ggagtttttt ggaaaaggga catttgaaag aagattcttc      1080
agagatgaga aagaacttca agaatacgag gcggctgaat tgaccaagac tgacatcgcg    1140
ttggctgatg acggaacagt caattctgat gacgaggatt acttctcggg tgaaactagg    1200
agtcctgaag ctgtttatac tcggatcatg atgaatggag gccgactaaa aagatcacac    1260
ataaggagat atgtctcagt cagttccaat catcaagctc gccccaactc attcgccgag    1320
tttctaaaca agacatattc taatgactca                                     1350
```

<210> SEQ ID NO 51
<211> LENGTH: 1350
<212> TYPE: DNA
<213> ORGANISM: Rabies virus

<400> SEQUENCE: 51
atggatgccg acaagattgt atttaaagtc aagaatcagg tggtctcctt gaagcctgag 60
atcatcgtgg accaatatga gtacaagtac ccggcaatca aggactcgag gaagcccagt 120
ataaccttag gaaaagcccc tgacttaaac aaagcataca agtcaatttt gtctggcatg 180
aatgcagcca agcttgaccc tgacgatgta tgctcttatc tagcagctgc aatgcagttt 240
tttgagggtg catgtcccga tgactgggtt agctacggga tcttgatagc acggaagggc 300
gacaagatca ccccaggcac tcttgtggat ataagacgta ccaatgtgga agggagttgg 360
gctctaacag gggtatgga gttgacaaga gatcccactg ttccagagca tgcatccttg 420
gtcggtcttc tcttgagttt gtataggtta agcaaaatat caggacagaa cactggcaat 480
tacaagacaa acattgcaga cagaatagag caaattttcg agacagcccc ttttgtcaag 540
attgtagagc atcatacgtt gatgacaacc cacaagatgt gcgccaactg gagtaccata 600
ccgaacttca gattcctagc cggaacctat gacatgtttt tctcccggat tgaacatctg 660
tattcagcaa tcagggtagg cacagtagtt actgcttatg aggactgctc agggttggtg 720
tcttttacag ggttcataaa gcaaataaat ctcactgcaa gagaagcgct gctatacttc 780
ttccacaaga acttcgaaga agagataaga aggatgtttg agccggggca ggaaactgca 840
attcctcact cttatttcat ccattttcgc tcattaggcc tgagcgggaa gtctccatac 900
tcatcgaatg cggttggtca tgttttcaac ctcattcact ttgttggatg ttacatgggc 960
caagtgagat ctctgaatgc aacagttatt gctacatgtg ccccacatga gatgtctgtt 1020
cttgggggtt acttagggga ggagtttttt ggaaaaggga cttttgagag aagattcttc 1080
agggatgaga aagaacttca agaatatgaa gcggctgaac tgaccaagac agaagtggct 1140
ttggcagatg acggaaccgt caactctgat gatgaggact acttctcaag tgaaaccagg 1200
agtcctgagg cggtttacac ccgaatcatg atgaatggaa gtcgattgaa aagatcacac 1260
ataaggaggt atgtctcagt cagctccaat catcaggccc gtcctaactc attcgctgaa 1320
tttttgaaca agacatactc aagtgattct 1350

<210> SEQ ID NO 52
<211> LENGTH: 1350
<212> TYPE: DNA
<213> ORGANISM: Rabies virus

<400> SEQUENCE: 52
atggatgccg acaagattgt attcaaggtc aataatcagg tggtctctct gaagcctgag 60
attatcgtgg accaatatga gtacaagtac ccggctatca aagacctgaa gaagcccagt 120
ataaccttag gaaaagctcc tgatttgaat aaagcataca aatcaatttt atctggcatg 180
aacgcagcca aactcgaccc tgatgatgta tgctcttatc tggctgccgc gatgcagttc 240
tttgagggat catgtcctga cgactggact agctatggaa tcctgatagc tcggaaggga 300
gataagatca cccctgattc tcttgtggac ataaaacgaa ctgatgtaga agggaattgg 360
gctctaacag gggcatgga gttgacaagg gaccctactg tttcagagca tgcatctctg 420
gttggccttc tcttgagttt gtataggttg agcaagatct ctggacagaa caccggcaat 480
tacaagacaa acatcgcgga tagaatagag cagattttcg agacagcccc ctttgcaaag 540
atcgtagaac atcatacttt gatgacgacc cacaaaatgt gtgctaactg gagtaccata 600
ccaaatttca gatttctggc tggaacttat gacatgtttt tctcccggat agaacatcta 660

| | |
|---|---|
| tattcagcga ttagagtagg cacagttgtc actgcttatg aggactgctc aggactggta | 720 |
| tcatttacag ggtttataaa gcaaataaat ctcactgcga gagaagcact attatatttc | 780 |
| ttccacaaga actttgagga agaaataaga agaatgttcg agcctgggca agaaactgct | 840 |
| gttccccatt cctatttcat ccattttcgt tcattgggct tgagtgggaa atctccgtac | 900 |
| tcatccaatg cagttggtca tgtattcaac ctcattcact ttgttggatg ttatatgggt | 960 |
| caggtgagat ctttaaatgc aacggtgatt gcaacatgtg ccccgcatga gatgtctgtt | 1020 |
| cttgggggct atttggggga ggagtttttt ggaaaaggaa cttttgagag gagattcttc | 1080 |
| agggacgaga aggaacttca ggaatatgag gcagctgaat taacaaaagc cgaaaaggcc | 1140 |
| ctggcagatg acggaacagt caattctgat gatgaggatt acttttccag tgaaactagg | 1200 |
| agtccagaag ccgtttacac acgaatcatg atgaatggag gtagactaaa agatcacac | 1260 |
| ataaggaggt atgtctcagt cagctctaac catcaaactc gccctaactc gtttgcagag | 1320 |
| tttttaaaca agacatattc gagtgactcg | 1350 |

<210> SEQ ID NO 53
<211> LENGTH: 1350
<212> TYPE: DNA
<213> ORGANISM: Rabies virus

<400> SEQUENCE: 53

| | |
|---|---|
| atggatgccg acaagattgt attcaaggtc aataatcagg tggtctctct gaagcctgaa | 60 |
| attatcgtgg accaatatga gtacaaatac ccggctatca aagacctgaa gaagcccagt | 120 |
| ataaccttag gaaaagctcc tgatttgagc aaagcataca aatcaatttt atctggcatg | 180 |
| aacgcagcca aactcgaccc tgatgatgta tgctcttatc tggctgccgc aatgcagttc | 240 |
| tttgagggat catgtcctga agattggact agttatggaa tcctgatagc taagaaggga | 300 |
| gataagatca ccccggattc tcttgtggac ataagacgta ctgatgtgga agggaattgg | 360 |
| gctctaacag ggggcatgga gttgacaagg gaccctactg tttcagagca tgcatctctg | 420 |
| gttggccttc tcttgagttt gtataggttg agcaaaatct ctggacagaa caccggcaat | 480 |
| tacaagacaa acatcgcgga tagaatgaac cagattttg agacagcccc cttcgcaaag | 540 |
| atcgtagaac atcacacctt gatgacgacc cacaaaatgt gcgctaactg gagtacagta | 600 |
| ccaaactacc aattttctgc tggaacttat gacatgtttt tctcccggat gaacatctg | 660 |
| tattcagcta ttagagtagg cacagttgtc actgcttatg aggactgctc aggactggtg | 720 |
| tcatttacag ggtttataaa gcaaataaat cttactgcga gagaagcact attatacttc | 780 |
| ttccacaaga actttgagga agaaataaga agaatgttcg agcccgggca agagactgct | 840 |
| gttcctcatt cctatttcat tcattttcgc tcattgggct taagtgggaa atctccgtac | 900 |
| tcgtccaatg cagttggtca tgtgttcaat ctatttcacc acataggggtg ttatatgggt | 960 |
| caggtgagat ctttaaatgc aacagtgatc acaacatgtg ctccgcatga gatgtctgtt | 1020 |
| ctcgggggct atttggggga ggagtttttc gggaaaggaa cttttgaaag gagattcttc | 1080 |
| agggacgaga aggaacttca ggaatatgag gcagctgaat tgacaaaagc tgaaacggcc | 1140 |
| ctggcagatg acggaactgt caattctgat gatgaggact acttctccag tgaaaccagg | 1200 |
| agtccagagg cagtttacac acgaatcatg atgaatggag gtagactaaa agatcacac | 1260 |
| ataaggaggt atgtctcagt cagctctaat caccaaactc gccctaattc gtttgcggag | 1320 |
| tttttaaaca aaacatactc aagtgactcg | 1350 |

<210> SEQ ID NO 54
<211> LENGTH: 1350
<212> TYPE: DNA
<213> ORGANISM: Rabies virus

<400> SEQUENCE: 54

```
atggatgcag acaagattgt atttaaagtc aagaatcagg tggtctcctt gaagcctgag     60
atcatcgtgg accaatatga gtacaagtac ccggcaatca aagactcgag gaagcccagt    120
ataaccttgg gaaaagcccc tgacttgaac aaagcataca agtcaatttt gtctggcatg    180
aatgcagcca agctcgaccc tgatgatgta tgctcttatc tagcagctgc aatgcagttc    240
tttgagggag cgtgtcccga tgactgggtt agctacggaa tcctgatagc gcggaggggc    300
gacaagatca ccccaaattc tcttgtggat ataagacgta ctaatgtgga agggaattgg    360
gctctaacag gggtatgga gttgacaagg gatcccactg ttccagagca tgcatccttg    420
gttggtcttc tcctaagttt gtataggttg agcaaaaatat caggacagaa cactggcaat    480
tacaagacaa acattgcaga tagaatagag caaattttcg agacagcccc ttttgtgaag    540
attgtggagc atcatacttt gatgacaacc cacaaaatgt gcgctaactg gagtaccata    600
ccgaacttca gattcctagc tgggacctat gacatgtttt tctctcggat tgaacatcta    660
tattcagcaa ttagggtagg cacagtagtc actgcttatg aggactgttc agggttggtg    720
tcgtttacag ggtttataaa gcaaataaat ctcactgcaa gggaagcgct gctatacttc    780
ttccacaaga acttcgaaga agaaataaga aggatgtttg agccggggca ggagactgca    840
gttcctcact cttatttcat ccattttcgt tcgttgggcc tgagcgggaa atctccatat    900
tcatcaaacg cagttggtca cgttttcaac ctcattcact ttgttggatg ttacatgggt    960
caagtgagat ctttgaatgc aacggttatt gctacatgtg ccccacatga gatgtctgtc   1020
cttgggggtt acttgggggga ggagtttttt ggaaaaggga cttttgagag aagattcttc   1080
agggacgaga aggaacttca ggaatatgag gcagctgaac tgaccaagac tgaagtggct   1140
ttggcagatg acggaaccgt caactctgat gatgaggatt acttctctag tgaaaccagg   1200
agtcctgagg cggtttacac ccgaatcatg atgaatggag gtagattgaa aagatcacac   1260
ataaggagat atgtctcagt cagctccaat catcaggctc gtcccaattc attcgctgag   1320
tttttgaaca agacatactc aagtgattct                                    1350
```

<210> SEQ ID NO 55
<211> LENGTH: 1350
<212> TYPE: DNA
<213> ORGANISM: Rabies virus

<400> SEQUENCE: 55

```
atggatgccg acaagattgt atttaaggtc aataaccagg tggtttctct gaagcctgaa     60
attattgtag atcagtatga atacaagtac ccggctatca aggactcgaa gaagcccagt    120
ataaccttag gaaaagcccc tgacttgaac aaagcataca agtcaatttt atccggcatg    180
aatgcagcca agcttgaccc tgatgatgta tgttcttatc tagcggctgc aatgcagttc    240
tttgagggag catgtcctga ggactggacc agctatggaa tcctgattgc acggaaggga    300
gacaagatca ccccagattc tcttgtggac ataaaacgta ctcatgtgga ggggaattgg    360
gctctaaccg gggtatgga tttgacgagg gaccccaccg tttcggagca tgcatcttta    420
gttggtcttc tcttgagtct gtataggttg agcaaaatat ctggacagaa caccggcaat    480
tacaagacaa atatcgcaga tagaatagag cagattttcg agacggcccc ctttgtaaag    540
```

-continued

```
atcgtagaac atcatacttt gatgacaacc cacaaaatgt gcgctaactg gagtaccata    600
ccgaacttca gattcctagc cggaacctac gacatgtttt tctccaggat tgaacatctg    660
tattcagcaa ttagagtggg aacagttgtt accgcttatg aggactgctc agggttggtg    720
tcgtttacag ggtttataaa gcaaataaat cttactgcaa gagaagcaat actatatttc    780
ttccacaaga actttgagga agagataaga agaatgtttg agcctggtca ggagaccgca    840
gttcctcatt cctatttcat ccattttcgt tcattgggcc tgagtgggaa atctccgtat    900
tcgtcaaatg cagttggtca cgtgttcaac ctcattcact tcgttggatg ttatatgggt    960
caagtgagat ctttgaatgc aacggttatt gccacatgtg ccccgcatga gatgtctgtt   1020
cttgggggtt atttgggga ggagtttttt ggaaaaggga ccttcgaaag aagattcttc   1080
agggacgaga aagaacttca agaatatgaa gcagccgaat taacgaaaac tgaggtagcc   1140
ttggcagatg acggaacagt caattccgat gatgaggact acttctctag tgaaactagg   1200
agcccagaag cagtttatac tcgaatcatg atgaatggag gcagactaaa aagatcacac   1260
ataaggagat acgtctcagt tagttccaat catcaagctc gccccaattc cttcgctgag   1320
tttctgaaca agacatactc gagtgattcg                                    1350
```

<210> SEQ ID NO 56
<211> LENGTH: 1350
<212> TYPE: DNA
<213> ORGANISM: Rabies virus

<400> SEQUENCE: 56

```
atggatgccg acaagattgt atttaaagtc aagaatcagg tggtctcctt gaagcctgag     60
atcatcgtag accaatatga gtacaagtac ccggcaatca aggactctag gaagcccagt    120
ataaccttag gaaaagcccc tgacttaaac aaagcataca agtcaatttt gtctggcatg    180
aatgcagcca agctcgaccc tgacgatgta tgctcttatc tagcagctgc aatgcagttc    240
tttgagggag catgtcccga tgactggatt agctacggaa tcctgatagc acggaagggc    300
gacaagatca ccccaggctc tcttgtggat ataagacgta ccaatgtgga agggagttgg    360
gctctaacag gggtatgga gttgacaaga gatcctactg ttccagagca agcatccttg    420
gtcggtcttc tcttgagttt gtataggtta agcaaaatat caggacagaa caccggcaat    480
tacaagacaa acattgcaga cagaatagag caaattttcg agacagcccc ttttgtcaag    540
attgtagagc atcatacttt gatgacaacc cacaaaatgt gcgctaattg gagtacgata    600
ccgaacttca gattcctagc cggaacctat gacatgtttt tctcccggat tgaacatctg    660
tattcagcaa ttagggtggg cacagtagtt actgcttatg aagactgctc agggttggtg    720
tcttttacgg ggttcataaa gcaaataaat ctcactgcaa gagaagctct gctatacttc    780
ttccacaaga acttcgaaga agagataaga aggatgtttg agccggggca agaaactgca    840
gttcctcact cttatttcat ccattttcgc tcactaggcc tgagcgggaa gtctccatac    900
tcatcgaacg cggttggtca tgtttttaac ctcattcact ttgttggatg ttacatgggc    960
caagtgagat ctctgaatgc aacggttatt gctacgtgtg ccccacatga gatgtctgtt   1020
cttgggggtt acttagggga ggagtttttc gggaaaggga cttttgagag aagattcttc   1080
agggatgaga aagaacttca agaatatgaa gcagccgaac tgaccaagac agaagtggct   1140
ttggcagatg acggaactgt caactctgat gatgaggact acttctcaag tgagaccagg   1200
agtcctgagg cggtttacac ccgaatcatg atgaatggag gtcgattaaa aagatcacac   1260
```

| | | |
|---|---|---|
| ataaggagat atgtctcagt cagctccaat catcaggccc gtcctaactc attcgccgaa | 1320 | |
| ttttttgaaca agacatactc aagtgattct | 1350 | |

<210> SEQ ID NO 57
<211> LENGTH: 1350
<212> TYPE: DNA
<213> ORGANISM: Rabies virus

<400> SEQUENCE: 57

| | |
|---|---|
| atggatgccg acaagattgt atttaaagtc aagaatcagg tggtctcctt gaagcctgag | 60 |
| atcatcgtgg accaatatga gtacaagtac ccggcaatca aggactcgag gaagcccagt | 120 |
| ataactttag gaaaagcccc tgatttaaac aaagcataca agtcgatttt gtctggcatg | 180 |
| aatgcagcca agctcgaccc tgacgatgta tgctcttatc tagcagctgc aatgcagttc | 240 |
| tttgagggag catgtcctga tgactggatt agctacggaa tcttgatagc acggaagggc | 300 |
| gacaagatca ccccaggttc tcttgtggat ataagacgca ccaatgtgga agggagttgg | 360 |
| gctctaacag ggggtatgga gttgacaagg gatcctactg ttccagagca tgcatccttg | 420 |
| gtcggtcttc tcttgagttt gtataggttg agcaaaatat caggacagaa cactggcaat | 480 |
| tacaagacaa acattgcaga cagaatagag caaatttttg agacagcccc ttttgtcaag | 540 |
| attgtggagc atcatacttt gatgacaacc cacaaaatgt gcgctaactg gagtacagta | 600 |
| ccgaacttca gattcctagc cggaacctat gacatgtttt tctcccggat tgaacaccta | 660 |
| tattcagcaa ttagggtagg cacagtagtc actgcttatg aggactgctc agggttggtg | 720 |
| tcttttacag ggttcataaa gcaaataaac ctcactgcaa gagaagcgct gctatacttc | 780 |
| ttccacaaga acttcgaaga agagataaga aggatgtttg agccggggca agaaactgca | 840 |
| gttcctcact cttatttcat ccattttcgt tcgttaggcc tgagcgggaa gtctccgtat | 900 |
| tcatcgaacg cggttggtca cgtttttcaac ctcattcact tcgttggatg ttacatgggc | 960 |
| caagtgagat ctctgaatgc aacggttatt gccacatgtg ccccacatga gatgtctgtt | 1020 |
| cttgggggtt acttagggga ggagttttt gggaaaggaa cttttgagag aagattcttc | 1080 |
| agagatgaga agaacttca agaatatgaa gcagctgaac tgaccaagac agaagtggct | 1140 |
| ttggcagatg acgggaccgt caactctgat gatgaggact acttctcaag tgagaccagg | 1200 |
| agtcctgaag cggtttacac ccgaatcatg atgaatggag tcgattgaa aagatcacac | 1260 |
| ataaggaggt atgtctcagt cagctctaat catcaggccc gtcctaactc tttcgctgaa | 1320 |
| ttttttaaaca agacatactc aagtgattct | 1350 |

<210> SEQ ID NO 58
<211> LENGTH: 1350
<212> TYPE: DNA
<213> ORGANISM: Rabies virus

<400> SEQUENCE: 58

| | |
|---|---|
| atggatgccg acaagattgt atttaaagtc aagaatcagg tggtctcctt gaagcctgag | 60 |
| atcatcgtgg accaatatga gtacaagtac ccggcaatca aggactcgag gaagcccagt | 120 |
| ataaccttag gaaaagcccc tgatttaaac aaagcataca agtcgatttt gtctggcatg | 180 |
| aatgcagcca agctcgaccc tgacgatgta tgctcttatc tagcagctgc aatgcagttc | 240 |
| tttgagggag catgtcctga tgactggatt agctacggaa tcttgatagc acggaagggc | 300 |
| gacaagatca ccccaggttc tcttgtggat ataagacgca ccaatgtgga agggagttgg | 360 |
| gctctgacag ggggtatgga gttgacaagg gatcctactg ttccagagca tgcatccttg | 420 |

```
gtcggtcttc tcttgagctt gtataggttg agcaaaatat caggacaaaa cactggcaat      480
tacaagacaa acattgcaga cagaatagag caaattttcg agacagcccc ttttgtcaag      540
attgtagagc atcatacttt gatgacaacc cacaaaatgt gtgctaactg gagtaccata      600
ccgaacttca gattcctagc cggaacctat gacatgtttt tctcccggat tgaacacctg      660
tattcagcaa ttagggtagg cacagtagtc actgcttatg aggactgctc agggttggtg      720
tcttttacag ggttcataaa gcaaataaac ctcactgcaa gagaagcgct gctatacttc      780
ttccacaaga acttcgaaga agagataaga aggatgtttg agccggggca ggaaactgca      840
gttcctcact cttatttcat ccattttcgt tcattaggcc tgagcgggaa gtctccatac      900
tcatcgaatg cggttggtca cgttttcaac ctcattcact cgttggatg ttacatgggc       960 caagtgagat ctctgaatgc aacggttatt gccacatgtg ccccacatga gatgtctgtt     1020
cttgggggtt acttagggga ggagttttttt gggaaaggaa cttttgagag aagattcttc    1080
agggatgaga aagaacttca agaatatgaa gcagctgaac tgaccaagac agaagtggct     1140
ttggcagatg acgggaccgt caactctgat gatgaggact acttctcaag tgagaccagg     1200
agtcctgaag cggtttacac ccgaatcatg atgaatggag tcgattgaa aagatcacac      1260 ataaggaggt atgtctcagt cagctccaat catcaggccc gtcctaactc tttcgctgaa     1320
tttttaaaca agacatactc aagtgattct                                      1350

<210> SEQ ID NO 59
<211> LENGTH: 1350
<212> TYPE: DNA
<213> ORGANISM: Rabies virus

<400> SEQUENCE: 59
atggatgccg acaagattgt attcaaagtc aataatcagg tggtctcttt gaagcctgag       60
attatcgtgg atcaatatga gtacaagtac cctgctatca agatttgaa gaagccctgt       120 ataaccctcg ggaaagcacc cgacttgaat aaagcgtaca atcggttct atcaggcatg       180 aatgccgcca acttgatccc tgatgatgta tgttcttatt tggcagcagc aatgcagttc       240
tttgagggga cgtgtccgga agattggacc agttatggaa tcctgattgc acgaaaagga      300
gataggatca ccccagattc tctggtggag ataaggcgta ctgatataga agggaactgg      360
gctctgacag ggggcatgga actgacaagg gaccccactg tccccgagca tgcgtcttta     420
gtcggtcttc tcttgagtct gtataggtta agcaaaatat caggacaaaa cactggtaac      480
tataagacga acattgcaga caggatagag caaattttg agacagcccc ttttgttaaa       540
gttgtggaac accatactct aatgacaact cacaaaatgt gtgccaattg gagtactata      600
ccgaacttca gatttctggc tggaacctac gacatgtttt tctcccggat tgagcatcta      660
tattcagcaa tcagagtggg cacagttgtc actgcttatg aagactgttc aggtctggta      720
tcgtttacgg ggttcataaa gcagatcaat ctcactgcaa agaagcgat actatatttc      780 ttccacaaga attttgagga ggagataaga agaatgttcg agccggggca agagacagct      840 gttcccccact cttatttcat tcacttccgt tcactaggct tgagtgggaa atctccttat     900
tcatcaaatg ccgttggtca tgtgttcaat ctcattcact tgttggatg ttatatgggt       960 caagtcagat ccctaaatgc aacagttatt gccgcatgtg ctcctcatga gatgtctgtt     1020
ctagggggat atctgggaga ggaattcttc gggaaaggaa catttgaaag aagattcttc     1080
agagatgaga aagaacttca agaatatgaa gcggctgaac taacaaagac tgacttagca     1140
ctggcagatg atggaacggt caactctgat gacgaggact acttctccgg tgaaaccaga    1200
```

| | |
|---|---|
| agtcctgaag ctgtttatac tcgaatcatg atgaatggag gtcggctaaa aagatcgcat | 1260 |
| atacggagat atgtctcagt tagctccaat catcaagctc gcccaaactc atttgccgag | 1320 |
| tttctgaaca agacgtactc gagtgactca | 1350 |

<210> SEQ ID NO 60
<211> LENGTH: 1350
<212> TYPE: DNA
<213> ORGANISM: Rabies virus

<400> SEQUENCE: 60

| | |
|---|---|
| atggatgccg acaagattgt attcaaagtc aataatcagg tggtctcttt gaagcctgag | 60 |
| attatcgtgg atcaatatga gtacaagtat cctgctatca agatttgaa aaagccctgt | 120 |
| ataaccctag ggaaagcccc cgacttaagt aaggcataca aatcagtttt gtcgggcatg | 180 |
| aatgccgcca aactcgaccc tgatgatgta tgttcctatt tggcagcagc aatgcagttc | 240 |
| tttgagggga catgtccgga agactggacc agctatggaa tcctgattgc acgaaaaggg | 300 |
| gataagatca ccccagattc tctggtggag ataaagcgta ctgatataga agggaattgg | 360 |
| gctctgacag gaggcatgga actgacaagg accccacaa tctctgagca tgcgtcttta | 420 |
| gtcggtcttc tgttgagtct gtataggttg agcaaaatat caggacaaaa cactggtaac | 480 |
| tacaagacaa acattgcaga caggatagag cagattttcg agacagcccc ttttgttaaa | 540 |
| atcgtggaac accatactct aatgacaact cacaaaatgt gtgccaattg gagtactata | 600 |
| ccgaacttca gattttttggc gggaacctat gacatgttttt ctcccggat tgagcatcta | 660 |
| tattcagcaa tcagagtggg cacagttgtc actgcttatg aagactgttc agggctggta | 720 |
| tcgtttaccg ggttcataaa gcaaatcaat ctcacagctg gagaagcgat actatatttc | 780 |
| ttccacaaga actttgagga agagataaga agaatgttcg agccagggca ggagacagct | 840 |
| gttcctcact cttattcat tcacttccgt tcactgggct tgagtgggaa atctccttat | 900 |
| tcatcaaaatg ctgtcggtca tgtgttcaat ctaattcact ttgttggatg ctatatgggt | 960 |
| caagtcagat ccctaaatgc aacggttata gccacatgtg ctcctcatga gatgtctgtt | 1020 |
| ctagggggct atctgggaga ggaatttttc gggaaaggaa catttgaaag aagattcttc | 1080 |
| agagatgaga aagaacttca agaatacgag gcggctgaac taacaaagac tgacgtggca | 1140 |
| ctggcagatg atggaactgt caactccgac gacgaggact acttctccgg tgaaactaga | 1200 |
| agtccggaag ctgtctatac tcgaatcata atgaatggag gtcgactaaa gagatcgcat | 1260 |
| atacggagat atgtctcagt cagttctaat catcaagccc gtccaaactc attcgccgag | 1320 |
| tttctaaaca agacgtactc gagtgactcg | 1350 |

<210> SEQ ID NO 61
<211> LENGTH: 1350
<212> TYPE: DNA
<213> ORGANISM: Rabies virus

<400> SEQUENCE: 61

| | |
|---|---|
| atggataccg acaaaattgt attcaaagtc aaaaatcagg ttgtctcctt gaagcctgag | 60 |
| atcatcgtag atcaatatga gtacaagtac ccggctataa aagacttgaa gaagccctgt | 120 |
| ataacattgg gaaagcccc tgacctgaac aaggcataca gtcgattttt gtccggcatg | 180 |
| aatgcagcta agctagaccc ggatgatgtg tgttcctatt tggcagctgc aatgcaattc | 240 |
| tttgaaggga catgtcctga agactggact agctatggaa tcttgattgc aaggaaggga | 300 |

```
gacaagatca ctccaaactc tcttgtggac ataaaacgta ctgacgtaga agggaactgg      360
gctctgacag ggggcctgga attgactagg gatcccacca tttcagaaca tgcatctttg      420
gtcggtcttc tcctgagtct gtatagactt agcaaaatat ctggacaaaa caccggcaat      480
tacaagacaa acattgccga tcgtatagaa cagattttg agacggcccc ctttgtgaag       540
atcgtagaac atcatactct gatgacaact cacaagatgt gcgctaactg gagcaccata      600
ccgaacttca gattcttatc tggaacttac gacatgtttt tctcccggat tgaacatcta      660
tactcagcaa taagagtggg tacagtggtc actgcttatg aggattgctc cgggttagtg      720
tcgtttactg ggtttataaa acagataaat ctcactgcta gagaagcaat cctttatttc      780
ttccacaaga attttgaaga agagataaga agaatgtttg agccaggaca ggaaactgca      840
gttcctcact cctatttcat ccattttcgg tctttgggcc tgagtgggaa atccccatac      900
tcgtcaaatg cagttggtca cgtgttcaac ctaattcact ttgttggatg ctatatgggt      960
caggtgaggt ctttgaatgc aactgtcatt gccacatgtg ccccgcatga gatgtctgtt     1020
ctcggaggtt atctggggga ggagttcttt ggcaagggaa cctttgagag aagattcttc     1080
agagacgaga aggaacttca ggaatatgaa acagcagagc tgacaaagac agaagtggcc     1140
ctagctgatg acgggacagt caactctgat gatgaagact acttctccgg tgaaacccgg     1200
agcccggagg cagtctatac tcgcatcatg atgaatgggg gtcgactcaa aggtcacac      1260
ataaggagat atgtctcagt tagttccaat catcaagctc gccccaattc attcgctgag     1320
tttctaaata agacatattc aaacgattca                                      1350

<210> SEQ ID NO 62
<211> LENGTH: 1350
<212> TYPE: DNA
<213> ORGANISM: Rabies virus

<400> SEQUENCE: 62
atggatgccg acaagattgt attcaaagtc aataatcagg tggtctcttt gaagcctgag       60
attatcgtgg atcaatatga gtacaagtac cctgctatta aggacttgaa gaagcccagt      120
atcaccctag gaaggccccc cgatttgaac aaggcataca agtcagtttt atcaggcttg      180
aatgctgcca agcttgatcc tgatgacgta tgttcctact tagcagctgc aatgcagttc      240
ttcgagggga cgtgtcccga agactggacc agctatggga tcctgattgc acggaaagga      300
gataagatca ccccagattc tctggtggag ataaagcgta ccggtgtaga agggaattgg      360
gctttaacgg gagggatgga actgacgagg accccactg ttccagagca tgcgtcttta       420
gtcggtcttc tcttgagcct gtatagacta agcaaaatat ctgggcaaaa caccggtaac      480
tataagacaa acattgcaga taggatagag cagatcttcg agacagcccc ctttatcaag      540
atcgtggagc atcatactct gatgacaact cacaagatgt gtgccaactg gagtactata      600
ccaaacttca gattcctggc agggacctac gacatgtttt tctcccggat tgagcatctg      660
tattcagcaa tcagagtagg tacggtagtc actgcttatg aggactgctc ggggctggta      720
tcatttaccg ggttcataaa acagataaat ctcactgcaa gggaagcaat actatatttc      780
ttccacaaaa acttcgagga agagataaga agaatgtttg agccaggaca gagacagct       840
gttcctcact cctatttcat tcactttcgt tcactgggcc tgagtgggaa gtcccctttat     900
tcatcaaatg cagttggtca tgtgttcaat ctcatccact ttgtcggatg ctatatggga      960
caagtgagat ctctgaatgc aacggtcatt gctgcatgtg ctcctcatga aatgtctgtt     1020
ttaggaggct attttggggga ggagttttc gggaagggga cgtttgagag agagattcttc    1080
```

| | |
|---|---|
| agagatgaga aagaacttca agaatatgag acggctgaat tgacaaagac tgacactgca | 1140 |
| ctggcagatg atggaactgt caattcggat gacgaggact acttctccgg ggaaaccaga | 1200 |
| agccctgagg ctgtttatgc ccgaatcatg atgaacgggg gcagactaaa gagatcgcac | 1260 |
| atacggagat atgtctcagt cagctcaaat caccaagctc gtcccaactc atttgctgag | 1320 |
| tttctaaaca agacgtattc tagtgactcg | 1350 |

<210> SEQ ID NO 63
<211> LENGTH: 1350
<212> TYPE: DNA
<213> ORGANISM: Rabies virus

<400> SEQUENCE: 63

| | |
|---|---|
| atggatgccg acaagattga gtttaaagtc aataatcaag tggtctcttt gaagcctgag | 60 |
| attatcgtgg atcaatatga atacaagtac cctgcaatca agatttgaa aaagccttgt | 120 |
| ataaccctag ggaaagcccc cgacttaaac aaagcataca aatcagttct atcaggcatg | 180 |
| aatgccgcca acttgatccc tgatgatgta tgctcctact tggcagcagc aatgcagttc | 240 |
| tttgagggta catgtccgga agactggacc agctatggga tcctgattgc acgaaaagga | 300 |
| gacaagatca ccccagactc tctagtggag ataaagcgta ctgatgtaga agggaattgg | 360 |
| gctctgacag gaggcatgga actgacaagg gaccccactg tctctgaaca tgcatcttta | 420 |
| gtcggtcttc tcctaagtct gtacaggttg agcaaaatat caggacaaaa cactggtaac | 480 |
| tataagacaa acattgcgga taggatagag cagatttcg agacagcccc ttttgttaag | 540 |
| atcgtggaac accataccct aatgacaact cacagatgt gtgctaattg gagtactata | 600 |
| ccgaaattca gatttttggc cggaacctac gacatgtttt tctcccggat tgagcatctg | 660 |
| tattcggcaa tcagagtggg cacagttgtc accgcttatg aagactgctc aggactggtg | 720 |
| tcgtttacag ggttcataaa gcagatcaat ctcactgcaa gagaagcaat actatatttc | 780 |
| ttccacaaga actttgagga agagataaga agaatgttcg agccagggca agagacagct | 840 |
| gttcctcact cttatttcat tcacttccgt tcactaggct tgagtgggaa atctccttat | 900 |
| tcatcaaatg ccgtcggtca tgtgttcaat ctcattcact ttgttggatg ctatatgggg | 960 |
| caagtcagat ctctaaatgc aacggttatt gctgcatgtg cccctcatga gatgtctgtt | 1020 |
| ctagggggct atttgggaga ggaattcttt gggaaaggga catttgaaag aaggttcttc | 1080 |
| agagacgaga agaacttca agaatatgag gcggctgaac tgacaaagac cgacgtggca | 1140 |
| ctggcagatg acggaaccgt caattccgat gacgaggact acttctccgg tgaaaccaga | 1200 |
| agtccagaag ctgtctatac tcgaatcatg atgaatggag gtcgactgaa gagatcgcat | 1260 |
| atacggagat atgtctcagt cagttccaat catcaagccc gtccaaactc atttgccgaa | 1320 |
| tttttaaaca agacgtattc aagtgactca | 1350 |

<210> SEQ ID NO 64
<211> LENGTH: 1350
<212> TYPE: DNA
<213> ORGANISM: Rabies virus

<400> SEQUENCE: 64

| | |
|---|---|
| atggatgccg acaagattgt attcaaagtc aataatcagg tggtctcctt gaagccggag | 60 |
| attatcgtgg atcagtatga gtacaaatac ccagccatca aggacttgaa gaaacctagt | 120 |
| ataactctag ggaaggctcc tgacctgaat aaagcataca agtcagtcct gtctggcatg | 180 |

```
aacgctgcca agcttgatcc tgatgatgtg tgttcctact tggcagccgc aatgcaattc      240
tttgagggat catgccctga ggactggacc agctatggaa tcttgattgc acgaaaagga      300
gacaagatca ctcctgattc tcttgtagag ataaaacgta ctgacataga aggtaattgg      360
gcactgacgg gaggtatgga agtgacgaga accccaccg ttgctgagca tgcatcttta       420
gtgggtcttc tcttgagtct gtataggttg agcaaaatat cggggcaaaa cactggcaac      480
tataagacaa acattgcaga caggatagag cagattttg agactgcccc ttttgtaaag       540
atcgtagaac accatactct gatgacaact cacaagatgt gcgccaattg gagtaccata      600
ccgaacttta gattcttagc tggaacctac gacatgtttt tctctcggat tgagcatttg      660
tattcagcta taagagtggg tacagttgtc actgcttatg aagactgctc agggttggtt     720
tcgttcacag ggttcataaa gcagataaat ctcaccgcga gagaggcaat cttatatttc      780
ttccacaaga actttgagga agaaataaga agaatgtttg agccagggca agaaacagcc      840
gtccctcact cctatttcat ccacttccgc tcattgggcc tgagcggaaa gtctccctat      900
tcatcgaatg cagttgggca tgtgttcaat ctcattcact tgttggatg ttatatgggt       960 caggtcaggt ctcttaatgc cacggttatt gccgcttgtg ccccccatga aatgtcagtt      1020
ctcggaggct atttgggaga gagtttttt ggaaagggga catttgaaag acgattcttt       1080
agggatgaga aggaactcca ggagtatgag gcggctgagc tgatgaagac tgacgtagca      1140
ctggcagaca acggaaccgt caattctgat gacgaggatt acttctccgg tgagacaagg      1200
agccccgagg ctgtctatac tcgaatcatg atgaacggag gtcgactgaa gagattacac      1260
ataaggagat atgttgccgt cagttctaac catcaagccc gcccaaactc gtttgccgag      1320
tttctaaaca agacatattc aagtgactcg                                       1350
```

<210> SEQ ID NO 65
<211> LENGTH: 1350
<212> TYPE: DNA
<213> ORGANISM: Rabies virus

<400> SEQUENCE: 65

```
atggatgccg acaagattgt attcaaagtc aataatcagg tggtctcttt gaagcctgag       60
attatcgtgg atcaatatga gtacaagtat cctgctatca aagatttgaa aaagccctgt      120
ataaccctag gaaaagcccc cgacttaaac aaagcataca atcagttttt atcgggcatg      180
aatgccgcca aacttgaccc tgatgatgta tgttcctatt tggcagcagc gatgcagttc      240
tttgagggga cgtgtccgga agattggacc agctatggaa tcctgattgc ccgaaaagga      300
gataagatca ccccagattc tctggtggag ataaagcgta ctgatgttga agggaattgg      360
gctctgacag gaggcgtgga actgacaagg gaccctactg tctctgagca tgcgtcttta      420
gtcggtcttc tattgagttt gtataggttg agcaaaatat caggacagaa cactggtaac      480
tataagacaa acattgcaga caggatagag cagattttcg agacagcccc ttttgttaaa      540
atcgtggaac atcatactct gatgacaact cataaaatgt gtgccaattg gagtactata      600
ccgaacttca gattttttggc cggaacctat gacatgtttt tctcccggat tgagcatcta      660
tattcagcaa tcagagttgg cacagttgtc actgcttatg aagactgttc agggctggta      720
tcgtttacgg ggttcataaa gcaaatcaat ctcaccgcag agaagcgat actatatttc       780 ttccacaaga actttgagga agagataaga agaatgtttcg agccagggca ggagacagct     840
gttcctcact cttatttcat tcacttccgt tcactaggct tgagtgggaa atctccttat      900
tcatcaaatg ctgtcggtca tgtgttcaat ctcattcact tgttggatg ttatatgggt       960
```

```
caagtcagat ccctaaatgc aacggttatc gccacatgtg ctcctcatga gatgtctgtt   1020
ctggggggct atctgggaga ggaattcttt gggaaaggaa catttgaaag aagattcttt   1080
agagatgaga aagaacttca agaatacgag gcagctgagc taacaaagac tgacgtagca   1140
ctggcagatg atggaactgt caactccgac gacgaggact acttctccgg tgagaccaga   1200
agtccggaag ctgtctatac tcgaatcatg atgaatggag gtcgactaaa gagatcgcat   1260
atacggagat atgtctcagt cagttctaat catcaaaccc gtccaagctc gtttgctgaa   1320
tttctaaaca agacgtattc gagtgactca                                   1350
```

<210> SEQ ID NO 66
<211> LENGTH: 1350
<212> TYPE: DNA
<213> ORGANISM: Rabies virus

<400> SEQUENCE: 66

```
atggatgccg acaagattgt attcaaagtc aataatcagg tggtctcttt gaagcctgag     60
attatcgtgg atcaatatga gtacaagtac cctgccatca aagatttgaa aaagccctgt    120
ataaccctag gaaaggctcc cgatttaaat aaagcataca agtcagtttt gtcaggcatg    180
agcgccgcca aacttgatcc tgacgatgta tgttcctatt tagcagcggc aatgcagttt    240
tttgagggga catgtccgga agactggacc agctatggaa tcgtgattgc acgaaaagga    300
gataagatca ccccaggttc tctggtggag ataaaacgta ctgatgtaga agggaattgg    360
gctctgacag gaggcatgga actgacaaga gaccccactg tccctgagca tgcgtcctta    420
gtcggtcttc tcttgagtct gtataggttg agcaaaatat ccgggcaaaa cactggtaac    480
tataagacaa acattgcaga caggatagag cagatttttg agacagcccc ttttgttaga    540
atcgtggaac accatactct aatgacaact cacaaaatgt gtgctaattg gagtactata    600
ccaaacttca gatttttggc cggaacctat gacatgtttt tctcccggat tgagcatcta    660
tattcagcaa tcagagtggg cacagttgtc actgcttatg aagactgttc aggactggta    720
tcatttactg ggttcataaa acagatcaat ctcaccgcta gagaggcaat actatatttc    780
ttccacaaga actttgagga agagataaga agaatgtttg agccagggca ggagacagct    840
gttcctcact cttatttcat ccacttccgt tcactaggct tgagtgggaa atctccttat    900
tcatcaaatg ctgttggtca cgtgttcaat ctcattcact ttgtaggatg ctatatgggt    960
caagtcagat ccctaaatgc aacggttatt gctgcatgtg ctcctcatga aatgtctgtt   1020
ctagggggct atctgggaga ggaattcttc gggaaaggga catttgaaag aagattcttc   1080
agagatgaga aagaacttca agaatacgag acggctgaac tgacaaagac tgacgtagca   1140
ctggcagatg atggaactgt caactctgac gacgaggact acttctcagg tgaaaccaga   1200
agtccggagg ctgtttatac tcgaatcatg atgaatggag gtcgactaaa gagatctcac   1260
atacggagat atgtctcagt cagttccaat catcaagccc gtccaagctc attcgccgag   1320
tttctaaaca agacatattc gagtgactca                                   1350
```

<210> SEQ ID NO 67
<211> LENGTH: 1350
<212> TYPE: DNA
<213> ORGANISM: Rabies virus

<400> SEQUENCE: 67

```
atggatgccg acaagattgt attcaaagtc aataatcagg tggtctcttt gaagcctgag      60
attatcgtgg atcaatatga gtacaagtac cctgctatca agatctgaa aaaaccctgt     120
ataaccctag ggaaagcccc cgacttaaac aaagcataca aatcggtttt atcaggcatg    180
aatgccgcca aacttgatcc tgatgatgta tgttcctacc tggcagcagc aatgcagttc    240
tttgagggga cgtgtccgga agattggacc agctatggaa tcttgattgc acgaaaaggg    300
gacaagatca ccccagattc tctggtggaa ataaaacgta ctgatgtaga agggaattgg    360
gctctgacag gaggcatgga actgacaagg acccccactg tctctgagca cgcatctttg    420
gtcggtcttc tcctgagtct gtataggttg agcaaaatat caggacaaaa cactggtaac    480
tataaaacaa acatagcaga tagaatagag cagattttcg agacagcccc ttttattaaa    540
atcgtggagc accatactct gatgacaact cacaaaatgt gtgctaattg gagcaccata    600
ccgaatttca gattttttggc tggaacctac gacatgttct tctcccggat tgagcatcta    660
tattcagcta tcatagtagg cacagttgtt actgcttatg aagactgttc agggctggta    720
tcgtttactg ggttcataaa gcagatcaat ctcaccgcaa gagaagcaat actatatttc    780
ttccataaaa acttgagga agagataaga agaatgttcg agccagggca ggaaacagct    840
gttcctcact cttatttcat tcacttccgt tcactaggct tgagtgggaa gtccccttac    900
tcttcgaatg ccgttggtca tgtgttcaac ctcattcact ttgttggatg ctatatgggt    960
caagtcagat ccctaaaatgc aacggttatt gctgcatgtg ctcctcatga gatgtctgtt   1020
ctagggggct atctaggaga ggaattcttc gggaaaggca cattcgaaag aagattcttc   1080
agggatgaga agaacttca agaatatgag gcggctgaac tgactaagac tgacgtggca   1140
tggcagatg atggaactgt caactctgat gacgaggact acttctccgg ggaaaccaga   1200
agtccagaag ctgttttatac tcgaatcatg atgaatggag gtcgactaaa gagatcgcat   1260
atacggagat atgtctcagt cagttccaat catcaagccc gtccaaactc attcgccgag   1320
tttctaaaaca agacatattc gagtgactca                                    1350
```

<210> SEQ ID NO 68
<211> LENGTH: 1350
<212> TYPE: DNA
<213> ORGANISM: Rabies virus

<400> SEQUENCE: 68

```
atggatgccg acaagattgt attcaaagtc aataatcagg tggtctcttt gaagcctgag      60
attatcgtgg accaatatga gtacaagtac cctgctatca agatctgaa aaagccctgt     120
ataaccctag ggaaagctcc cgacttgaac aaagcataca agtcagtttt atcaggcatg    180
aatgctgcca aactggatcc cgatgatgta tgctcctact tggcagcagc aatgcagttt    240
tttgagggga catgtccgga agactggacc agctatggaa tcctgattgc aagaaaagga    300
gacaagatca ctccagactc tctagtggag ataaagcgta ctgatgtaga agggaactgg    360
gccctgacag gaggcatgga actgacaagg acccccacta tctccgagca tgcatctttca   420
gttggtcttc tcttgagtct gtacaggctg agcaaaatat caggacaaaa cactggtaac    480
tataagacaa acattgcaga taggatagag cagattttcg agacagcccc ttttgttaag    540
atcgtggagc atcatacccct aatgacaact cacaagatgt gcgctaactg gagtactata   600
ccaaacttca gattttttggc cggaacctac gacatgttct tctcacggat tgagcatttg    660
```

```
tattcagcaa tcagagtggg cacagttgtc actgcttatg aagactgctc agggttggta      720
tcgtttactg ggttcataaa acagatcaat ctcaccgcaa gagaagcaat actatatttc      780
ttccacaaga attttgagga agagataagg aggatgttcg agccagggca ggagacagct      840
gttcctcact cttatttcat tcatttccgt tcactaggct tgagtgggaa gtctccttat      900
tcatcaaatg ctgttggtca tgtgttcaat ctcattcact ttgtcggatg ctacatgggt      960
caagtcagat ctctaaatgc aacggttatt gctgcatgtg cccctcatga gatgtctgtt     1020
ctagggggtt atttgggaga ggagttcttt ggaaaaggaa catttgaaag aagattcttc     1080
agagatgaga aagaacttca agaatatgag gcggctgaac tgacgaagac tgatgtggca     1140
ctggcagatg atggaactgt caactccgac gacgaggact acttctccgg tgaaaccagg     1200
agtccagaag ctgtctatac tagaatcatg atgaatggag gtcgattgaa gagatcacat     1260
atacggagat atgtcacagt cagttctaat catcaagccc gtccaaactc attcgcagag     1320
tttctaaaca agacatactc gagtgactca                                      1350

<210> SEQ ID NO 69
<211> LENGTH: 1350
<212> TYPE: DNA
<213> ORGANISM: Rabies virus

<400> SEQUENCE: 69
atggataccg acaagattgt attcaaagtc aataatcatg tggtctcttt gaagcctgag

```
<210> SEQ ID NO 70
<211> LENGTH: 1350
<212> TYPE: DNA
<213> ORGANISM: Rabies virus

<400> SEQUENCE: 70 atggat

```
atcgtagaac atcatacttt gatgacaacc cacaaaatgt gcgctaactg gagtaccata

```
ataaggagat atgtctcagt aagttccaat catcaagctc gccctaattc attcgctgag   1320
tttctaaaca agacatactc taatgattca                                   1350
```

<210> SEQ ID NO 73
<211> LENGTH: 1350
<212> TYPE: DNA
<213> ORGANISM: Rabies virus

<400> SEQUENCE: 73

```
atggatgccg acaagattgt attcaaagtc aataatcagg tggtttcttt gaagcctgag     60
attatcgtgg accaatatga gtacaaatac cctgctatca aagatttgaa aaagccctgt    120
ataaccctag ggaaagcccc cgacttaaac aaggcataca agtcagtttt atcaggcatg    180
aatgctgcca aacttgatcc cgatgatgta tgctcatacc tggcagcagc aatgcagttc    240
tttgaggggg catgtccaga agactggacc agctacggaa tcctgatcgc acgaaaagga    300
gacaagatca ctccagactc tctagtggaa ataaagcgta ctgatgtaga agggaactgg    360
gctctgacag gaggcatgga actgacaagg gaccccactg tctccgagca tgcatcttta    420
gttggtctcc tcttgagtct gtacaggctg agcaaaatat caggacaaaa cactggtaac    480
tacaagacca acattgcaga taggatagag cagattttcg agacagcccc ttttgttaag    540
atcgtagagc atcataccct aatgacaact cacaagatgt gcgctaattg gagtactata    600
ccaaacttca gatttttggc tggaacctac gacatgtttt tctcacggat tgagcatctg    660
tattcagcaa tcagagtggg cacagttgtc actgcttatg aagactgctc gggattggta    720
tcgtttacag ggttcataaa acagatcaat ctcaccgcaa gagaagcaat actatatttc    780
ttccacaaga actttgagga agaaataaga aggatgttcg agccagggca ggagacagct    840
gtccctcact cttatttcat tcatttccgt tcactaggct tgagtgggaa gtctccttat    900
tcctcaaatg ccgttggtca tgtgttcaat ctcattcact ttgtcggatg ttatatgggt    960
caagtcagat ctctaaacgc aacggttatt gctgcatgtg ccccccacga gatgtccgtt   1020
ctaggaggtt atttaggaga ggaattcttc gggaaaggaa catttgagag aagattcttc   1080
agggatgaga aagaacttca agaatatgag gcggctgaac tgacgaagac tgatgtggca   1140
ctggcagatg atggaactgt caactccgac gacgaagact atttctccgg tgaaaccaga   1200
agtccagaag ctgtctatac tcgaataatg atgaatggag gtcgattgaa gagatcgcat   1260
atacgtagat atgtctcagt cagttccaat catcaagccc gtccgaactc attcgcagag   1320
tttctaaaca agacatattc gagtgactca                                   1350
```

<210> SEQ ID NO 74
<211> LENGTH: 1350
<212> TYPE: DNA
<213> ORGANISM: Rabies virus

<400> SEQUENCE: 74

```
atggatgcag acaagattgt atttaaagtc aagaatcagg tggtctcctt gaagcctgag     60
atcatcgtgg accaatatga gtacaagtac ccggcaatca aagactcgag gaagcccagt    120
ataaccttgg gaaaagcccc tgacttgaac aaagcataca agtcaatttt gtctggcatg    180
aatgcagcca agctcgaccc tgatgatgta tgctcttatc tagcagctgc aatgcagttc    240
tttgagggag cgtgtcccga tgactgggtt agctacggaa tcctgatagc gcggaggggc    300
gacaagatca ccccaaattc tcttgtggat ataagacgta ctaatgtgga agggaattgg    360
```

```
gctctaacag ggggtatgga gttgacaagg gatcccactg ttccagagca tgcatccttg    420
gttggtcttc tcctaagttt gtataggttg agcaaaatat caggacagaa cactggcaat    480
tacaagacaa acattgcaga tagaatagag caaattttcg agacagcccc ttttgtgaag    540
attgtggagc atcatacttt gatgacaacc cacaaaatgt gcgctaactg gagtaccata    600
ccgaacttca gattcctagc tgggacctat gacatgtttt tctctcggat tgaacatcta    660
tattcagcaa ttagggtagg cacagtagtc actgcttatg aggactgttc agggttggtg    720
tcgtttacag ggtttataaa gcaaataaat ctcactgcaa gggaagcgct gctatacttc    780
ttccacaaga acttcgaaga agaaataaga aggatgtttg agccggggca ggagactgca    840
gttcctcact cttatttcat ccattttcgt tcgttgggcc tgagcgggaa atctccatat    900
tcatcaaacg cagttggtca cgttttcaac ctcattcact ttgttggatg ttacatgggt    960
caagtgagat ctttgaatgc aacggttatt gctacatgtg ccccacatga gatgtctgtc   1020
cttggggggtt acttggggga ggagtttttt ggaaaaggga cttttgagag aagattcttc  1080
agggacgaga aggaacttca ggaatatgag gcagctgaac tgaccaagac tgaagtggct   1140
ttggcagatg acggaaccgt caactctgat gatgaggatt acttctctag tgaaaccagg   1200
agtcctgagg cggtttacac ccgaatcatg atgaatggag gtagattgaa aagatcacac   1260
ataaggagat atgtctcagt cagctccaat catcaggctc gtcccaattc attcgctgag   1320
tttttgaaca agacatactc aagtgattct                                    1350
```

<210> SEQ ID NO 75
<211> LENGTH: 1350
<212> TYPE: DNA
<213> ORGANISM: Rabies virus

<400> SEQUENCE: 75

```
atggatgctg acaagattgt atttaaagtc aagaatcagg tggtctcctt gaagcctgag     60
atcatcgtgg accaatatga gtacaagtac ccggcaatca aagactcgag gaagcccagt    120
ataaccttag gaaaagcccc tgacttaaac aaagcataca agtcaatttt gtctggcatg    180
aatgcagcca agctcgaccc tgacgatgta tgctcttatc tagcggctgc aatgcagttc    240
tttgagggag catgtcccga tgattggatt agctacggaa tcctgatagc acggaagggc    300
gacaaaatca ccccaggctc tcttgtggat atcagacgta ctaatgtgga agggagttgg    360
gctctaacag ggggtatgga gttgacaaga gatcccactg ttccagagca tgcatccttg    420
gtcggtcttc tcttgagttt gtataggttg agcaaaatat caggacagaa cactggcaat    480
tacaagacaa acattgcaga cagaatagag caaattttcg agacagcccc ttttgtcaag    540
attgtggagc atcatacttt gatgacaacc cacaaaatgt gtgccaactg gagtactata    600
ccgaacttca gattcctagc cggaacctat gacatgtttt tctcccggat tgaacatctg    660
tattcagcta ttagggtagg cacagtagtt actgcttatg aggactgctc agggctggtg    720
tcttttacag ggttcataaa gcaaataaat ctcactgcaa gagaagcgct gctgtacttc    780
ttccacaaga acttcgaaga agagataaga aggatgtttg agcctgggca ggaaactgca    840
gttcctcact cttatttcat ccattttcgc tcattaggcc tgagcgggaa gtctccatac    900
tcatcgaacg cggttggtca tgttttcaac ctcattcact ttgttggatg ttacatgggc    960
caagtgagat ctctgaatgc aacggttatt gctacatgtg ccccacatga gatgtctgtt   1020
cttggggggtt acttagggga ggagtttttt ggaaaaggga cttttgagag aagattcttc  1080
agggatgaga aagaacttca agaatatgaa gcagctgaac tgaccaagac agaagtggct   1140
```

```
ttggcagatg acggaaccgt caactctgat gatgaggact acttctcaag tgagaccagg     1200
agtcctgagg cggtttacac ccgaatcatg atgaatggag gtcgattgaa aagatcacac     1260
ataaggaggt atgtctcggt cagctccaat catcaggccc gtcctaactc attcgctgaa     1320
tttttgaaca agacatactc aagtgattct                                       1350

<210> SEQ ID NO 76
<211> LENGTH: 1350
<212> TYPE: DNA
<213> ORGANISM: Rabies virus

<400> SEQUENCE: 76
atggatgccg acaagattgt atttaaagtc aagaatcagg tggtctctct gaagcctgaa       60
attattgtgg accaatatga gtacaagtac ccggctatca agactctag gaagcccagt      120 ataaccttgg gaaaagcccc tgacttgaac aaggcataca atcaatttt atccggcatg      180 aatgcagcca aactagaccc tgatgatgta tgctcttatc tggcagccgc aatgcagttc      240
tttgagggag catgtcctga tgactggatc agctatggaa tcctgatagc acgaagggga      300
gacaagatca ccccagaatc tctcgtagac atcaggcgta ccaatgtgga agggaattgg      360
gctctaacag ggggtatgga gttgactagg accccactg tttctgaaca tgcatctttg      420
gttggtcttc tcttgagttt gtataggttg agtaaaatat ctggacagaa caccggcaat      480
tacaagacaa acatcgcaga taggatagag cagattttcg agacggcccc ctttgtaaag      540
attgtggaac atcatacttt aatgacaacc cataaaatgt gcgccaactg gagtaccata      600
cctaacttca gatttctggc tgggacctat gacatgtttt ctcccggat gaacatctg       660 tattccgcga ttagagtagg cacagttgtt actgcttatg aggactgctc agggttggtg      720
tcattcacgg ggtttataaa gcaaataaat cttactgcga gagaagctct gctatatttc      780
ttccataaga acttttgagga agagataaga agaatgtttg aaccggggca ggagactgca      840
gttcctcact cctatttcat ccatttccgt tccttgggct tgagtgggaa atcgccatac      900
tcatcaaatg cagttggcca tgtgttcaat ctcattcact ttgtcgggtg ctacatgggt      960
caggtgagat ctttgaatgc cacggttatt gccacatgtg ccccgcatga gatgtctgtt     1020
cttgggggat acttggggga ggagtttttt ggaaaaggga ctttttgagag aagattcttc    1080 agagacgaga gagaacttca ggaatatgaa gcggctgagt tgatgaggac tgatacggca    1140
ttggcagatg acgggaccgt caactctgat gacgaggact acttctctgg tgagacccgg     1200
agtccggagg cggtttatac ccgaatcatg atgaatggag gtagactgaa aagatcacat     1260
ataaggaggt atgtatcagt cagctccaat catcaagctc gacccaattc atttgctgag     1320
ttcttaaaca agacatattc gaatgactca                                       1350

<210> SEQ ID NO 77
<211> LENGTH: 1350
<212> TYPE: DNA
<213> ORGANISM: Rabies virus

<400> SEQUENCE: 77
atggatgccg acaagattgt attcaaagtc aataatcagg tggtctcttt gaagcctgag       60
attatcgtgg atcaatatga gtacaagtac ccagctatca agatttgaa aaagccctgt      120 ataaccctag ggaaagcccc cgacttaaac aaagcataca agtcaatctt gtcaggcatg      180
aatgcagcca aacttgatcc tgatgatgta tgttcctact tagcagcagc aatgcagttc      240
```

```
tttgagggga cgtgtccaga agactggacc agctatggaa tcttgatcgc acgaaaagga    300
aacaagatca ccccggattc tctggtggaa ataaagcgta ctgatgtaga aggaaattgg    360
gctctgacag gaggcatgga actgacaagg gaccccactg tccccgaaca tgcgtcttta    420
gttggtcttc tcttgagtct gtataggttg agcaaaatat caggacaaaa cactggtaac    480
tataaaacaa acatcgcaga taggatagag cagattttcg agacagctcc ttttgttaaa    540
atcgtggaac accatactct aatgacaact cacaaaatgt gcgctaattg gagtactata    600
ccgaatttca gatttttggc cgggacctac gacatgtttt tctctcggat tgagcatcta    660
tattcagcaa tcagagtggg cacggttgtt actgcttatg aagactgttc aggtttggta    720
tcgtttactg ggttcataaa gcagatcaat ctcactgcaa gagaagcaat actatacttc    780
ttccacaaga attttgagga agagataaga agaatgttcg agccaggtca ggagacagct    840
gttcctcact cctatttcat tcacttccgt tcactaggct tgagtgggaa gtctccttat    900
tcatcgaatg ccgttggtca tgtgttcaat ctcattcact ttgtcggatg ctatatgggt    960
caagtcagat ccctaaatgc aacagtcatt gctgcatgtg ctcctcatga gatgtctgtt   1020
ctagggggct atctgggaga ggaattcttc gggaaaggaa cattcgagag aagattcttc   1080
agagatgaga aggaactcca agaatacgaa gcgactgaac tgacaaagac tgacgtggca   1140
ttggcagacg atggaactgt caactctgac gatgaggact acttctccgg tgaaaccaga   1200
agtcctgaag ctgtttatac tcgaatcatg atgaatggag gtcgactaaa gagatcgcat   1260
ataaggagat atgtctcagt cagttcaaat catcaagctc gtccaaactc atttgctgag   1320
tttctaaaca agacatattc gaacgactca                                    1350
```

<210> SEQ ID NO 78
<211> LENGTH: 1350
<212> TYPE: DNA
<213> ORGANISM: Rabies virus

<400> SEQUENCE: 78

```
atggatgccg acaagattgt attcaaagtc aataatcagg tggtctcttt gaaaccagag     60
attatcgtgg atcaatatga gtacaagtac cctgctatca aagatttgaa aaagccctgt    120
ataaccctag ggaaagcccc cgacttaaac aaagcataca agtcagtctt atcgggcatg    180
aatgcagcca aacttgatcc tgatgatgta tgttcctact tggcagcagc aatgcagttc    240
tttgagggga cgtgtccaga agactggacc agctatggaa tcttgatcgc acgaaaagga    300
gccaagatca ccccggattc tctggtggaa ataaagcgta ctgatgtaga aggaaattgg    360
gctctgacag gaggcatgga actgacaagg gaccccactg tctctgaaca tgcgtcttta    420
gttggtcttc tcttgagtct gtataggttg agcaaaatat caggacaaaa cactggtaac    480
tataaaacaa acatcgcaga taggatagag cagattttcg agacagcccc tttcgttaaa    540
atcgtggaac accatacttt aatgacaact cacacaatgt gcgctaactg caggactata    600
ccgaatttca gatttctggc cgggacctac gacatgtttt tctcccggat tgagcatcta    660
tattcagcaa tcagagtggg cacagttgtt accgcttatg aagactgttc aggtctggta    720
tcgtttactg gattcataaa gcagatcaat ctcactgcaa gagaagcaat actatacttc    780
ttccacaaga actttgagga agagataaga agaatgttcg agccagggca ggagacagct    840
gtccctcact cctatttcat tcacttccgt tcactaggtt tgagtgggaa gtctccttat    900
tcatcgaatg ccgttggtca tgtgttcaat ctcattcact ttgtcggatg ctatatgggt    960
caagtcagat ccctaaatgc gacagttatt gccgcatgtg ctcctcatga gatgtctgtt   1020
```

```
ctagggggct atctaggaga ggaattcttt gggaaaggaa cattcgagag aaggttcttc   1080
agagatgaga aagaacttca agaatacgag gcggctgaac tgacaaagac tgacgtggca   1140
ttggcagacg atggaactgt caactctgac gatgaggact acttctccgg tgaaaccaga   1200
agtccagagg ctgtttatac tcgaatcatg atgaatggag gtcgactaaa gagatcgcat   1260
atacggagat atgtctcagt cagctcaaat catcaagctc gtccaaactc atttgctgat   1320
tttctaaaca agacatattc gaacgactca                                    1350
```

<210> SEQ ID NO 79
<211> LENGTH: 1350
<212> TYPE: DNA
<213> ORGANISM: Rabies virus

<400> SEQUENCE: 79

```
atggatgccg acaagattgt attcaaagtc aataatcagg tggtctcttt gaaaccagag     60
attatcgtgg atcaatatga gtacaagtac cctgctatca aagatttgaa aaagccctgt    120
ataaccctag ggaaagcccc cgacttaaac aaagcataca agtcagtctt atcgggcatg    180
aatgcagcca aacttgatcc tgatgatgta tgttcctact tggcagcagc aatgcagttc    240
tttgagggga cgtgtccaga agactggacc agctatggaa tcttgatcgc acgaaaagga    300
gccaagatca ccccggattc tctggtggaa ataaagcgta ctgatgtaga aggaaattgg    360
gctctgacag gaggcatgga actgacaagg gaccccactg tctctgaaca tgcgtcttta    420
gttggtcttc tcttgagtct gtataggttg agcaaaatat caggacaaaa cactggtaac    480
tataaaacaa acatcgcaga taggatagag cagattttcg agacagcccc tttcgttaaa    540
atcgtggaac accatactta tgtgccacgc cagattatgt gcactaattg gagtactata    600
ccgaatttca gatttctggc cgggacctac gacatgtttt tctcccggat tgagcatcta    660
tattcagcaa tcagagtggg cacagttgtt accgcttatg aagactgttc aggtctggta    720
tcgtttactg gattcataaa gcagatcaat ctcactgcaa gagaagcaat actatacttc    780
ttccacaaga actttgagga agagataaga agaatgttcg agccagggca ggagacagct    840
gtccctcact cctatttcat tcacttccgt tcactaggtt tgagtgggaa gtctccttat    900
tcatcgaatg ccgttggtca tgtgttcaat ctcattcact ttgtcggatg ctatatgggt    960
caagtcagat ccctaaatgc gacagttatt gccgcatgtg ctcctcatga gatgtctgtt   1020
ctagggggct atctaggaga ggaattcttt gggaaaggaa cattcgagag aaggttcttc   1080
agagatgaga aagaacttca agaatacgag gcggctgaac tgacaaagac tgacgtggca   1140
ttggcagacg atggaactgt caactctgac gatgaggact acttctccgg tgaaaccaga   1200
agtccagagg ctgtttatac tcgaatcatg atgaatggag gtcgactaaa gagatcgcat   1260
atacggagat atgtctcagt cagctcaaat catcaagctc gtccaaactc atttgctgat   1320
tttctaaaca agacatattc gaacgactca                                    1350
```

<210> SEQ ID NO 80
<211> LENGTH: 1350
<212> TYPE: DNA
<213> ORGANISM: Rabies virus

<400> SEQUENCE: 80

```
atggatgccg acaagattgt gttcaaagtc aataatcagg tggtctcttt gaagcctgag     60
attatcgtgg atcaatatga gtacaagtac cctgccatca aggatttgaa aaagccttgt    120
```

-continued

```
atcaccctag ggaaagcccc cgacttgaac aaagcataca aatcagtttt atcaggcatg      180
aatgccgcca aacttgatcc ggatgatgta tgctcctact tggcagcagc aatgcagttc      240 tttgaggga catgtccgga agactggacc agctatggaa tcctgattgc acgaaaagga       300
gataggatca ccccaaactc tctagtggag ataaagcgta ctgatgtaga agggaattgg      360
gctctgacag gaggcatgga attgacaagg accccactg tctctgaaca tgcatcttta      420
gtcggtcttc tcctgagtct gtacaggttg agcaaaatat caggacagaa cactggtaac      480
tataagacaa acattgcaga taggatagag cagattttcg agacagcacc ttttgttaag      540
atcgtggaac accataccct aatgacaact cacaagatgt gcgctagctg gagtactaca      600
ccgaacttca gattttggc cggaacctac gacatgtttt tctcacggat tgagcatctg       660
tattcggcaa tcagagtggg cacagtcgtc accgcttatg aagactgctc aggactggta      720
tcgtttacag ggttcataaa gcagatcaat ctcaccgcaa gggaagcaat actatatttc      780
ttccacaaga actttgagga agagataaga agaatgttcg agccagggca agagacagct      840
gttcctcact cttatttcat ccacttccgt tcactaggct tgagtgggaa gtctccttat      900
tcatcgaatg ctgtcggtca tgtgttcaat ctcattcact tgttggatg ctacatgggt       960 caagtcagat ctctaaatgc gacggttatt gctgcatgtg cccctcatga gatgtctgtt     1020 ctaggggct atttgggaga ggaattcttc ggaaaaggga catttgaaag aaggttcttc      1080
agagacgaga aagaacttca agaatatgag gcggctgaac taacaaagtc cgacgtggca     1140
ctggcagatg acggaaccgt caactctgat gacgaggact atttctctgg tgaaaccaga     1200
agtccagaag ctgtctatac tcgaatcatg atgaatggag gtcgactgaa gagatctcat     1260
atacggagat atgtctcagt cagttccaat catcaagccc gtccaaactc attcgccgaa     1320
tttttaaaca agacgtattc gaatgactca                                      1350
```

<210> SEQ ID NO 81
<211> LENGTH: 1350
<212> TYPE: DNA
<213> ORGANISM: Rabies virus

<400> SEQUENCE: 81

```
atggatgccg acaagattgt attcaaagtc aataatcagg tggtctcctt gaagccggag       60
attatcgtgg atcagtatga gtacaaatac ccagccatca aggacttgaa gaaacctagt      120
ataactctag ggaaggctcc tgacctgaat aaagcataca agtcagtcct gtctggcatg      180
aacgctgcca agcttgatcc tgatgatgtg tgttcctact tggcagccgc aatgcaattc      240
tttgagggat catgccctga ggactggacc agctatggaa tcttgattgc acgaaaagga      300
gacaagatca ctcctgattc tcttgtagag ataaaacgta ctgacataga aggtaattgg      360
gcactgacgg gaggtatgga agtgacgaga acccccaccg ttgctgagca tgcatcttta      420
gtgggtcttc tcttgagtct gtataggttg agcaaaatat cggggcaaaa cactggcaac      480
tataagacaa acattgcaga caggatagag cagattttg agactgcccc ttttgtaaag      540
atcgtagaac accatactct gatgacaact cacaagatgt gcgccaattg gagtaccata      600
ccgaacttta gattcttagc tggaacctac gacatgtttt tctctcggat tgagcatttg      660
tattcagcta taagagtggg tacagttgtc actgcttatg aagactgctc agggttggtt      720
tcgttcacag ggttcataaa gcagataaat ctcaccgcga gagaggcaat cttatatttc      780
ttccacaaga actttgagga agaaataaga agaatgtttg agccagggca agaaacagcc      840
gtccctcact cctatttcat ccacttccgc tcattgggcc tgagcggaaa gtctccctat      900
```

```
tcatcgaatg cagttgggca tgtgttcaat ctcattcact ttgttggatg ttatatgggt    960
caggtcaggt ctcttaatgc cacggttatt gccgcttgtg ccccccatga aatgtcagtt   1020
ctcggaggct atttgggaga agagtttttt ggaaagggga catttgaaag acgattcttt   1080
agggatgaga aggaactcca ggagtatgag gcggctgagc tgatgaagac tgacgtagca   1140
ctggcagacg acggaaccgt caattctgat gacgaggatt acttctccgg tgagacaagg   1200
agccccgagg ctgtctatac tcgaatcatg atgaacggag gtcgactgaa gagattacac   1260
ataaggagat atgttgccgt cagttctaac catcaagccc gcccaaactc gtttgccgag   1320
tttctaaaca agacatattc aagtgactcg                                     1350
```

<210> SEQ ID NO 82
<211> LENGTH: 1350
<212> TYPE: DNA
<213> ORGANISM: Rabies virus

<400> SEQUENCE: 82

```
atggatgccg acaagattgt atttaaagtc aataatcagg tggtttctct gaagcctgaa     60
attatcgtgg atcaatatga gtacaagtac cctgccatca aggacctgaa gaagcccagt    120
ataaccttag gaaaggcccc tgatttaaac aaagcataca agtcaatctt atccggcatg    180
aatgcagcca aacttgaccc tgatgatgta tgctcttatc tggcagctgc aatgcagttc    240
tttgaaggag catgtcctga agactggact agctatggaa tcctgattgc acggaaggga    300
gacaagataa ccccaaattc tcttgtggac ataaaacgta ctcatgtgga agggaattgg    360
gctctgacag ggggtatgga gttgacaagg gaccccactg ttgcagaaca tgcatctctg    420
gtcggtcttc tcttgagtct gtataggttg agcaaaatat ccggccaaaa caccggcaat    480
tacaagacga acattgcaga tagaatagag cagattttcg agacggctcc ttttgtaaag    540
attgtagaac atcatactct gatgacaacc cacaaaatgt gcgctaactg gagtaccata    600
ccaaacttta gatttctagc cggaacctac gacatgtttt tctcccggat tgaacatctg    660
tattcagcaa ttagagtggg aacagttgtc actgcttatg aggactgctc agggttggta    720
tcgtttacgg ggtttattaa acaaataaat ctcactgcaa gagaagcaat actatatttc    780
ttccacaaga atttcgaaga ggagataaga aggatgtttg agccggggca agagactgct    840
gttcctcact cttatttcat ccattttcgc tcattgggct tgagtgggaa atctccatat    900
tcatcaaatg cagttggtca tgtgttcaac ctcattcact ttgtcggatg ttatatgggt    960
caggttagat ccttaaatgc aacggttatt gccacatgtg ccccgcatga aatgtctgtt   1020
cttggggggtt atttaggaga ggagtttttt gggaagggga cttttgagag aagattcttc   1080
agggacgaga aagaacttca ggaatatgaa gcagctgaat tgacgaagac tgaggtagcc   1140
ttggcagatg atggaacagt caattctgat gacgaggact acttctccag tgaaaccagg   1200
agtccagaag cggtttatac tcgaatcatg atgaatggag gcagactcaa aaggtcacac   1260
ataaggagat ttgtctcagt tagctccaat catcaagctc gccctaattc attcgctgag   1320
tttttaaaca agacatactc gagtgattct                                     1350
```

<210> SEQ ID NO 83
<211> LENGTH: 1350
<212> TYPE: DNA
<213> ORGANISM: Rabies virus

<400> SEQUENCE: 83

```
atggatgccg acaagattgt gttcaaagtc aataatcagg tggtctctt gaagcctgaa      60
attatcgtgg atcaatatga atacaagtac cctgcaatca agatttgaa aaagccttgt     120
ataaccctgg ggaaggcccc cgacttaaac aaagcataca aatcagtttt atcaggcatg    180
aatgccgcca aacttgatcc tgatgatgta tgctcctact tggcagcagc aatgcagttc    240
tttgagggta catgtccgga agactggacc agctatggaa tcctgattgc acgaaaagga    300
gacaagatca ctccagactc tctagtggag ataaagcgta cggatgtaga aggaaattgg    360
gctctgacag gaggtatgga attgacaagg accccactg tctctgaaca tgcatcttta    420
gtcggccttc tcctaagtct gtacagattg agcaaaatat caggacagaa cactggtaac    480
tataagacga acattgcgga taggatagag cagattttcg acacagcccc ttttgttaag    540
atcgtggaac accacaccct aatgacaact cacaagatgt gcgctaactg gagtactata    600
ccgaatttca gattttggc cggaacctac gacatgttct tctcacggat tgagcatctg    660
tattcggcaa tcagagtggg cacagttgtc accgcttatg aagactgctc aggactggta    720
tcgtttacag ggttcataag gcagatcaat ctcactgcaa gagaggcaat actatatttc    780
ttccacaaaa actttgaaga agagataaga agaatgttcg agccagggca agagacagcc    840
gttcctcact cttatttcat tcacttccgt tcgctaggct tgagtgggaa gtctccctat    900
tcatcaaatg ccgtcggtca tgtgttcaat ctcattcact ttgttggatg ctatatgggt    960
caagtcagat ccctaaatgc aacggttatt gctgcatgtg ctcctcatga gatgtctgtt   1020
ttagggggct atttgggaga ggaattcttt ggaaaaggga catttgaaag aaggttcttc   1080
agagatgaga agaacttca agaatatgag gcggctgaac tgacaaagac tgacgtggca   1140
ctggcagatg acggaaccgt caattccgat gacgaggact acttctccgg tgaaaccaga   1200
agtccagaag ctgtctatac tcgaatcatg atgaatggag gtcgactgaa gagatcgcat   1260
atacggagat atgtctcagt cagttccaat catcaagccc gtccaaactc atttgccgaa   1320
ttttttaaaca agacgtattc aagtgactca                                   1350
```

<210> SEQ ID NO 84
<211> LENGTH: 1350
<212> TYPE: DNA
<213> ORGANISM: Rabies virus

<400> SEQUENCE: 84

```
atggatgccg acaagattgt atttaaagtc aataatcagg tggtttctct gaagcctgag      60
attatcgttg atcaatatga gtacaagtac ccggctatca aggacttgaa gaagcccagt     120
ataaccttag gaaaagcccc tgatttgaac aaagcataca agtcaatttt atccggcatg    180
aatgcagcca agcttgaccc agatgatgta tgttcttatc tggcagctgc aatgcagttc    240
tttgagggag catgccctga tgactggacc agctatggaa tcctgattgc acggagggga    300
gacaagatca ctccagattc tcttgtagac ataaaacgta ctcatgtgga agggaattgg    360
gctctaacag ggggtatgga gttgacgaga gatcctaccg tttcggagca tgcatcttta    420
gttggtcttc tcttgagtct gtataggttg agcaagatat ctggacaaaa caccggcaac    480
tacaaaacaa acatcgcgga tagaatagag cagattttcg agacggcccc ctttgtaaag    540
atcgtggaac atcatacttt gatgacaacc cataagatgt gcgctaactg gagcaccata    600
ccgaacttca gattcctagc tgggacttac gatatgtttt tctcccggat tgaacatctg    660
```

| | |
|---|---:|
| tattcagcaa ttagagtggg cacagttgtc actgcttacg aggactgctc agggttggtg | 720 |
| tcgtttacag ggtttataaa gcaaataaat ctcactgcaa gagaggcaat actgtatttc | 780 |
| ttccacaaga acttcgagga agagataaga agaatgtttg agccggggca agaaaccgca | 840 |
| gttcctcact cctatttcat ccattttcgt tcgttgggcc tgagtgggaa atctccgtat | 900 |
| tcatcaaacg cagtcggtca cgtgttcaac ctcattcact ttgttggatg ttatatgggt | 960 |
| caagtgagat ctttgaatgc aacagtcatt gccacatgtg ccccgcacga gatgtctgtt | 1020 |
| cttgggggtt atctggggga ggagtttttt ggaaaaggga cttttgaaag aagattcttc | 1080 |
| agggatgaga aagaacttca ggaacatgag gcagctgaat taacgaagat tgaagtggcc | 1140 |
| ttggcagatg acggaacagt caattctgat gacgaggact acttctctag tgagaccagg | 1200 |
| agtccgagg cagtttatac ccgaatcatg atgaatggag gtagactaaa agatcacac | 1260 |
| ataaggagat atgtctcagt tagttccaat catcaagctc gccctaattc attcgctgag | 1320 |
| tttctaaaca agacatactc gagtgattct | 1350 |

<210> SEQ ID NO 85
<211> LENGTH: 1350
<212> TYPE: DNA
<213> ORGANISM: Rabies virus

<400> SEQUENCE: 85

| | |
|---|---:|
| atggatgccg acaagattgt attcaaagtc aataatcagg tggtctcttt aaagcctgag | 60 |
| attatcgtgg atcaatatga gtacaagtac cctgctatca agattcgaa aaagccctgt | 120 |
| ataaccctag ggaaggcccc cgacttaaac aaagcataca aatcggttct gtcaggcatg | 180 |
| aatgccgcca aactagatcc cgatgatgta tgttcctacc tggcagcagc aatgcagttc | 240 |
| tttgagggga catgtccgga agactggacc agctatggaa tcctgatcgc aaggaaagga | 300 |
| gacaagatca ccccggactc tctagtggaa ataaagcgta ctgatgtaga agggaactgg | 360 |
| gctctggcag gaggcatgga actcacaagg gaccccactg tctctgagca tgcatctta | 420 |
| gtcggtcttc tcttgagtct gtataggttg agcaaaatat caggacaaaa caccggtaac | 480 |
| tataaaacaa acattgcaga taggatagag cagattttcg agacagcccc ttttattaaa | 540 |
| atcgtggagc accatacccet aatgacaact cacaaaatgt gtgctaattg gagtactata | 600 |
| ccgaatttca gattttttggc tggaacctac gacatgtttt tctcccggat tgagcatcta | 660 |
| tattcagcaa tcagagtggg cacagttgtt actgcttatg aagactgttc agggctggta | 720 |
| tcgtttactg ggttcataaa acagatcaat ctcactgcaa aggaagcaat actatatttc | 780 |
| ttccataaga actttgagga agagataaga agaatgttcg agccagggca ggagacagca | 840 |
| gtccctcact cttatttcat tcacttccgt tcactaggct tgagtgggaa gtcaccttat | 900 |
| tcatcgaatg ccgttggtca tgtgttcaat ctcattcact ttgttggatg ttatatgggt | 960 |
| caagtcagat ccctaaatgc aacagttatt gccgcatgtg ctcctcatga gatgtctgtt | 1020 |
| ctaggggct acctgggaga ggaattcttc gggaaaggaa cattcgaaag aagattcttc | 1080 |
| agagatgaga aagaacttca agaatacgag gcggctgaac tgacaaagac tgacgtggca | 1140 |
| ttggcagatg atggaactgt caactctgac gatgaggact acttctccgg tgaaaccaga | 1200 |
| agtccagaag ctgtctatac cagaataatg atgaatggag gtcgactaaa gagatcgcat | 1260 |
| atacggagat atgtctcagt cagttctaat catcaagccc gtccaaactc attcgctgag | 1320 |
| tttttaaaca agacatattc gagtgactca | 1350 |

<210> SEQ ID NO 86
<211> LENGTH: 1350
<212> TYPE: DNA
<213> ORGANISM: Rabies virus

<400> SEQUENCE: 86
atggatgccg acaagattgt attcaaagtc aataatcagg tggtctcttt gaagcctgag 60
attatcgtgg atcaatatga gtacaagtac cctgctatca aagacttgaa aaagccctgt 120
ataaccttgg ggaaagcccc cgacttaaac aaagcataca agtcagtttt atcaggcatg 180
aacgccgcca aactagatcc tgatgatgtg tgttcctact tggcagcagc aatgcagttc 240
tttgagggga catgtccgga agactggacc agctatggaa tcctgattgc acgaaaaggc 300
gataagatca ccccagattc tcttgtggag ataaaacgta ctgatgtaga gggaaattgg 360
gccctgacag gaggcataga gctgacaagg gaccctactg tctccgagca tgcgtcttta 420
gttggtcttc ttttaagcct atataggctg agcaaaatat caggacaaaa caccggcaac 480
tataagacaa acattgcaga taggatagag cagattttcg agacagcccc ctttgttaaa 540
atcgtggagc accacactct aatgacaact cacaaaatgt gtgccaattg gagcactata 600
ccgaacttca gatttttggc tgggacctac gacatgtttt tctcccggat tgagcatcta 660
tattcagcaa tcagggtagg cacagttgtc actgcttatg aagactgctc agggctggta 720
tcgtttacag ggttcataaa acagattaat ctcaccgcaa gagaagcaat actatatttc 780
ttccacaaga actttgagga agagataaga agaatgttcg agccagggca ggagacagct 840
gttcctcact cttatttcat ccacttccgt tcactaggct tgagtggaaa gtctccttat 900
tcatcaaatg ccgttggtca tgtgttcaat ctcattcatt ttgtcggatg ctacatgggt 960
caagtccgat cccttaatgc aacagttatt gccgcctgtg cccctcatga gatgtctgtt 1020
ctagggggct atcttggaga ggaattcttc gggaaaggga cgtttgaaag aagattcttt 1080
agagatgaaa aagagcttcg agaatatgag gcggctgaac taataaagac tgacgtggca 1140
ctggcagacg acggaactgt caactccgac gacgaggact acttctccgg tgagaccaga 1200
agtccagaag ctgtttatac tcgaatcatg atgaatggag gtcgactgaa gagatcgcat 1260
attcggagat atgtctcagt cagttcaaat catcaaaccc gtccaggctc attcgctgag 1320
ttcctaaaca agacgtattc gagtgactca 1350

<210> SEQ ID NO 87
<211> LENGTH: 1350
<212> TYPE: DNA
<213> ORGANISM: Rabies virus

<400> SEQUENCE: 87
atggatgccg acaagattgt attcaaagtc aataatcagg tggtctcttt gaagcctgag 60
attatcgtgg atcaatatga gtacaagtac ccagctatca aagatttgaa aaagccctgt 120
ataaccctag ggaaagcccc cgacttaaac aaagcataca agtcaatctt gtcaggcatg 180
aatgcagcca aacttgatcc tgatgatgta tgttcctact tagcagcagc aatgcagttc 240
tttgagggga cgtgtccaga agactggacc agctatggaa tcttgatcgc acgaaaagga 300
aacaagatca ccccggattc tctggtggaa ataaagcgta ctgatgtaga aggaaattgg 360
gctctgacag gaggcatgga actgacaagg gaccccactg tccccgaaca tgcgtcttta 420
gttggtcttc tcttgagtct gtataggttg agcaaaatat caggacaaaa cactggtaac 480
tataaaacaa acatcgcaga taggatagag cagattttcg agacagctcc ttttgttaag 540

| | | |
|---|---|---|
| atcgtggaac accatactct aatgacaact cacaaaatgt gtgccaattg gagcactata | 600 |
| ccgaatttca gattttttggc cgggacctac gacatgtttt tctctcgtat tgagcatcta | 660 |
| tattcagcaa tcagagtggg cacggttgtt actgcttatg aagactgttc aggtttggta | 720 |
| tcgtttactg ggttcataaa gcagatcaat ctcactgcaa gagaagcaat actatacttc | 780 |
| ttccacaaga attttgagga agagataaga agaatgttcg agccaggtca ggagacagct | 840 |
| gttcctcact cctatttcat tcacttccgt tcactaggct tgagtgggaa gtctccttat | 900 |
| tcatcgaatg ccgttggtca tgtgttcaat ctcattcact ttgtcggatg ctatatgggt | 960 |
| caagtcagat ccctaaatgc aacagtcatt gctgcatgtg ctcctcatga gatgtctgtt | 1020 |
| ctaggggct atctgggaga ggaattcttc gggaaaggaa cattcgagag aaggttcttc | 1080 |
| cgagatgaga aggaactcca agaatacgag gcgactgaac tgacaaagac tgacgtggca | 1140 |
| ttggcagacg atggaactgt caactctgac gatgaggact acttctccgg tgaaaccaga | 1200 |
| agtcctgaag ctgtttatac tcgaatcatg atgaatggag gtcgactaaa gagatcgcat | 1260 |
| ataaggagat atgtctcagt cagttcaaat catcaagctc gtccaaactc atttgctgag | 1320 |
| tttctaaaca agacatattc gaacgactca | 1350 |

<210> SEQ ID NO 88
<211> LENGTH: 1350
<212> TYPE: DNA
<213> ORGANISM: Rabies virus

<400> SEQUENCE: 88

| | | |
|---|---|---|
| atggatgccg acaagattgt attcaaagtc aataatcagg tggtctcttt gaaaccagag | 60 |
| attatcgtgg atcaatatga gtacaagtac cctgctatca aagatttgaa aaagccctgt | 120 |
| ataccctag ggaaagcccc cgacttaaac aaagcataca agtcagtctt atcgggcatg | 180 |
| aatgcagcca aacttgatcc tgatgatgta tgttcctact ggcagcagc aatgcagttc | 240 |
| tttgaggga cgtgtccaga agactggacc agctatggaa tcttgatcgc acgaaaagga | 300 |
| gccaagatca ccccggattc tctggtggaa ataaagcgta ctgatgtaga aggaaattgg | 360 |
| gctctgacag gaggcatgga actgacaagg accccactg tctctgaaca tgcgtctta | 420 |
| gttggtcttc tcttgagtct gtataggttg agcaaaatat caggacaaaa cactggtaac | 480 |
| tataaaacaa acatcgcaga taggatagag cagattttcg agacagcccc tttcgttaaa | 540 |
| atcgtggaac accatacttt aatgacaact cacaaaatgt gtgctaattg gagtactata | 600 |
| ccgaatttca gatttctggc cgggacctac gacatgtttt tctcccggat tgagcatcta | 660 |
| tattcagcaa tcagagtggg cacagttgtt accgcttatg aagactgttc aggtctggta | 720 |
| tcgtttactg gattcataaa gcagatcaat ctcactgcaa gagaagcaat actatacttc | 780 |
| ttccacaaga actttgagga agagataaga agaatgttcg agccagggca ggagacagct | 840 |
| gtccctcact cctatttcat tcacttccgt tcactaggtt tgagtgggaa gtctccttat | 900 |
| tcatcgaatg gcgttggtca tgtgttcaat ctcattcact ttgtcggatg ctatatgggt | 960 |
| caagtcagat ccctaaatgc gacagttatt gccgcatgtg ctcctcatga gatgtctgtt | 1020 |
| ctaggggct atctaggaga ggaattcttt gggaaaggaa cattcgagag aaggttcttc | 1080 |
| agagatgaga aagaacttca gaatacgag gcggctgaac tgacaaagac tgacgtggca | 1140 |
| ttggcagacg atggaactgt caactctgac gatgaggact acttctccgg tgaaaccaga | 1200 |
| agtccagagg ctgtttatac tcgaatcatg atgaatggag gtcgactaaa gagatcgcat | 1260 |

| | |
|---|---|
| atacggagat atgtctcagt cagctcaaat catcaagctc gtccaaactc atttgctgat | 1320 |
| tttctaaaca agacatattc gaacgactca | 1350 |

<210> SEQ ID NO 89
<211> LENGTH: 1350
<212> TYPE: DNA
<213> ORGANISM: Rabies virus

<400> SEQUENCE: 89

| | |
|---|---|
| atggatgccg acaagattgt gttcaaagtc aataatcagg tggtctcttt gaagcctgag | 60 |
| attatcgtgg atcaatatga gtacaagtac cctgccatca aggatttgaa aaagccttgt | 120 |
| atcaccctag ggaaagcccc cgacttgaac aaagcataca atcagttttt atcaggcatg | 180 |
| aatgccgcca acttgatccc ggatgatgta tgctccctact ggcagcagc aatgcagttc | 240 |
| tttgaggga catgtccgga agactggacc agctatggaa tcctgattgc acgaaaagga | 300 |
| gataggatca ccccaaactc tctagtggag ataaagcgta ctgatgtaga agggaattgg | 360 |
| gctctgacag gaggcatgga attgacaagg acccccactg tctctgaaca tgcatcttta | 420 |
| gtcggtcttc tcctgagtct gtacaggttg agcaaaatat caggacagaa cactggtaac | 480 |
| tataagacaa acattgcaga taggatagag cagattttcg agacagcacc ttttgttaag | 540 |
| atcgtggaac accataccct aatgacaact cacaagatgt gtgctaattg gagtactata | 600 |
| ccgaacttca gattttggc cggaacctac gacatgtttt tctcacggat tgagcatctg | 660 |
| tattcggcaa tcagagtggg cacagtcgtc accgcttatg aagactgctc aggactggta | 720 |
| tcgtttacag ggttcataaa gcagatcaat ctcaccgcaa gggaagcaat actatatttc | 780 |
| ttccacaaga actttgagga agagataaga agaatgttcg agccagggca agagacagct | 840 |
| gttcctcact cttatttcat ccacttccgt tcactaggct tgagtgggaa gtctccttat | 900 |
| tcatcgaatg ctgtcggtca tgtgttcaat ctcattcact tgttggatg ctacatgggt | 960 |
| caagtcagat ctctaaatgc gacggttatt gctgcatgtg cccctcatga gatgtctgtt | 1020 |
| ctagggggct atttgggaga ggaattcttc ggaaaaggga catttgaaag aaggttcttc | 1080 |
| agagacgaga aagaacttca agaatatgag gcggctgaac taacaaagtc cgacgtggca | 1140 |
| ctggcagatg acggaaccgt caactctgat gacgaggact atttctctgg tgaaaccaga | 1200 |
| agtccagaag ctgtctatac tcgaatcatg atgaatgag gtcgactgaa gagatctcat | 1260 |
| atacggagat atgtctcagt cagttccaat catcaagccc gtccaaactc attcgccgaa | 1320 |
| ttttaaaca agacgtattc gaatgactca | 1350 |

<210> SEQ ID NO 90
<211> LENGTH: 1350
<212> TYPE: DNA
<213> ORGANISM: Aravan virus

<400> SEQUENCE: 90

| | |
|---|---|
| atggattctg acaagattgt cttcaaggtc cataaccagt tggtttcagt gaagcctgag | 60 |
| gtgattactg atcagtatga gtataagtat cctgccattg ggaatcagaa aaaacccagc | 120 |
| ataactctcg gcaaggctcc agacttaaac aaggcttaca agtctattct gtctggaatg | 180 |
| aatgccgcaa agctggaccc tgatgacgtc tgttcttatc ttgctgctgc catggagctg | 240 |
| tttgaaggag tgtgccctga tgattgggca agttatggaa ttcttattgc taagaaggga | 300 |
| gacaaaatca ctccgaccac cttggtggac attatccgaa cggatgtgga agggaattgg | 360 |

```
gcacaaactg gaggtcaaga tttgactagg gatccgacaa ctgccgagca tgcatcattg      420
gtaggacttc ttctttgtct ttaccgattg agcaagattg ttggacaaaa cacgggaaat      480
tacaagacaa acgttgctga tcggatggag caaatctttg agacagctcc cttcgtcaag      540
gtggttgaac atcacacatt gatgaccact cacaagatgt gtgcaaattg agcacgata       600 ccaaatttca ggttcctggc aggaacatat gacatgttct tctcgaggat agaacacttg      660
tactcagcta tcagagtagg gactgttgta actgcatatg aggattgctc tggattggtt     720
tcattcactg gattcatcaa acagatcaat ttgacagcca gagaggccat attgtatttc     780
tttcacaaaa actttgagga ggagatcaaa cggatgtttg aacccgggaca ggaaactgca     840 gttcctcatt cctacttcat acatttcaga tccttgggtc tgagcggcaa atctccgtac     900
tcatccaatg cagttggtca tgtattcaat ctcattcact tgtaggttg ctacatgggt      960 caaatcaggt cactaaatgc tactgttatt tctagttgtg cacctcatga gatgtctgtc     1020
ttagggggct attggggga ggagttcttt ggaaaaggga cgtttgagag gaggttcttt      1080
agagatgaga aggagctgca ggattatgaa ttagcagagg ccacaaagac agatttagcg     1140
ttagctgacg acgggactgt caattccgat gatgaagact tcttttctgg ggagaccagg    1200
agtcctgagg ctgtatacac tagaattatg atgaacggag ggaggctgaa gaagtctcac     1260
ataaggagat atgtctcggt cagctccaac catcaggcca gacccaactc gtttgccgaa     1320
ttccttaata agacctactc gggtgatcag                                      1350

<210> SEQ ID NO 91
<211> LENGTH: 1350
<212> TYPE: DNA
<213> ORGANISM: Khujand virus

<400> SEQUENCE: 91
atggatgccg acagaattgt ctttaaagtt aagaatcagt tggtgtctgt taagccggag      60
gtgattgttg atcagtacga gtacaaatac ccggctattg tggataggca gaagcccagc     120
atcactctgg ggaaagctcc agacctgaac aaggcttaca agtccattct ttccggattg     180
actgctgcca aactcgatcc ggatgatgtc tgttcttatt tggccgcagc aatggagctg     240
tttgatggaa cttgccccga tgattggacg agttatggga tccttattgc caagaaagga     300
gataaaatca ctccagccac tttagttaac attcaaagaa cagatgtcga gggcaactgg     360
gcattgaccg gaggtctaga cctgacaaga gatccgactg tagccgaaca tgcatcctta     420
gtggggctcc ttctcagcct ttatcgactg agtaaagtct ctgggcagaa cacagggaat     480
tacaaaacca atgttgctga ccgaatggag caaatcttcg acagcctcc atttgccaaa     540 attgtggaac atcacaccct tgatgaccac tcacaaaatgt gtgctaactg gagcacaatt     600 cccaattta ggttttagc agggacatat gacatgtttt tctcgagaat tgagcatttg      660
tattcagcca taagagtagg aactgttgtg accgcatatg aggattgttc tgggttggtt    720
tcattcacag ggttcatcaa acagataaat ttgacagcga aggaagcgat attgtatttc    780
ttccacaaaa attttgaaga agagatcaag aggatgtttg agccaggtca ggagacggct     840
gtcccgcatt cttatttcat ccacttcagg tcattgggac taagtggaaa atctccatac     900
tcttcgaatg cagttggtca tgtgtttaac ctcatccact tgtcggctg ttacatgggc     960 cagattagat ctttaaacgc aactgtcatc tctagttgtg cacctcatga gatgtcggtt    1020
cttggtggtt acttagggga ggagtttttc ggtaagggaa cattcgaaag gagatttttc     1080
agggatgaga aagagctcaa ggagtatgag gctgctgagt cagtaaagac ggacacagcc     1140
```

```
ttggcagatg atggaactgt caattccgat gacgaagact ttttctctgg agagacaaga   1200
agtccggaag cagtgtacac caggattatg atgaacggag gacgattgaa aaagtcccac   1260
atcaggagat atgtttccgt cagctcaaac catcaagcaa gaccaaactc atttgctgag   1320
tttttgaata aaacctactc aagtgatcca                                    1350
```

<210> SEQ ID NO 92
<211> LENGTH: 1350
<212> TYPE: DNA
<213> ORGANISM: Duvenhage virus

<400> SEQUENCE: 92

```
atggatgctg aaagaattgt ctttaaggtc cgtaatcagc tagtctctgt aaaaccagag     60
gtcatctctg atcagtatga gtacaaatat cctgctatta ctgataagaa gaagcctagt    120
atcacacttg gaagggctcc ggacttgaag acagcgtaca agtccatctt atcggggatg    180
aatgccgcca agctggatcc agatgacgta tgttcatact tagcaggtgc tatgattttg    240
tttgagggtg tgtgtcccga agattgggtt agttatggaa tccacattgc ccggaaaggc    300
gataaaataa cccctgctac gttagttgac atagttagaa caaatacaga aggtaactgg    360
gctcagacgg ggggtcagga attaactaga gatccaacaa tctcagaaca tgcatcattg    420
gtaggacttt tactttgcct atataggtta agcaaaattg taggacagaa cacagggaat    480
tataagacga atgtggctga ccggatggaa cagatttttg aaactgctcc attcgtcaag    540
atagtcgagc accacacatt aatgaccact cacaaaatgt gtgcgaattg gagcacaata    600
cccaatttta gatttcttgc aggaacatat gacatgttct tctccagggt ggatcatttg    660
tactcggcta ttagggttgg gacggtagtt actgcatatg aagattgttc aggtttagtc    720
tcctttactg ggtttatcaa gcagattaac ttgaccgcta gagaagccat attatacttc    780
tttcacaaga actttgagga ggagatcaaa agaatgtttg agcccggaca ggagactgct    840
gtgcctcact cctacttcat ccactttaga tccttaggtc ttagcggcaa gtctccttac    900
tcctccaatg ctgtcggaca tgtgttcaac ttgatccatt tcgtaggttg ttacatgggt    960
caaatcagat cattaaacgc tacagttatc caaagttgtg ccccgcatga gatgtccgta   1020
ttgggaggtt atttgggaga ggaattcttc ggaaagggga cctttgagag acgattcttt   1080
cgggacgaga aagagctgca agactatgaa gaagcagagg ccactaagat tgaggctgca   1140
ttggctgatg atggaactgt gaactccgac gatgaagact tttctccgg agatacaaga    1200 agtccagaag ctgtttacac aaggatcatg atgaacggag ggcgattaaa gggagcacac   1260
ataagaaggt acgtctctgt aagttctagt caccaagcaa gaccaaactc ctttgcagag   1320
ttcctcaaca agacctactc cagtgactcc                                    1350
```

<210> SEQ ID NO 93
<211> LENGTH: 1350
<212> TYPE: DNA
<213> ORGANISM: Duvenhage virus

<400> SEQUENCE: 93

```
atggatgctg aaagaattgt ctttaaggtc cgtaatcagc tagtctctgt aaaaccagag     60
gtcatctctg atcagtatga gtacaaatat cctgctatta ctgataagaa gaagcctagt    120
atcacacttg gaagggctcc ggacctgaag acagcataca agtccatctt gtcggggatg    180
aatgccgcca agctggatcc agatgacgta tgttcatact tagcaggtgc tatgattttg    240
```

```
tttgagggtg tgtgtcccga agattgggtt agttatggaa tccccattgc ccggaaaggc        300
gataaaataa cccctgctac gttagttgac atagttagaa cgaatacaga gggtaactgg        360
gctcagacgg gaggtcagga tttaactaga gatccaacaa tctcagaaca tgcatcattg        420
gtaggacttt tactctgcct atataggtta agcaaaattg taggacagaa cacaggaaat        480
tacaagacga atgtggctga ccggatggaa cagattttg aaactgctcc atttgtcaag         540
atagtcgagc accacacatt aatgaccact cacaaaatgt gtgcgaattg gagcacaata        600 cccaattta gatttcttgc aggaacatat gacatgttct tctccagggt ggatcatttg         660
tactcggcta ttagggttgg gacggtagtc actgcatatg aagattgttc aggtttagtc        720
tcctttactg ggtttatcaa gcagattaac ttgaccgcta gagaagccat attatacttc        780
tttcacaaga actttgagga ggagatcaaa agaatgtttg agcccggaca ggagactgct        840
gtgcctcact cctactttat ccactttaga tccttaggtc ttagcggcaa gtctccttac        900
tcctccaatg ctgtcggaca tgtgttcaac ttgatccatt ttgtaggttg ttacatgggt        960
caaatcagat cattaaacgc cacagttatc caaagttgtg ccccgcatga gatgtccgta       1020
ttgggaggtt atttgggaga ggaattcttt ggaaagggga cctttgagag acgattcttt       1080
cgggacgaga aagagctgca agactatgaa gaagcagagg ccactaagat tgaggctgca       1140
ttggctgatg atggaactgt gaactccgac gatgaagact ttttctccgg agatacaaga       1200
agtccagaag ctgtttacac aaggatcatg atgaacggag ggcggttaaa gggggcacac       1260
ataagaaggt acgtctctgt aagttctagt caccaagcaa gaccaaactc ctttgcagag       1320
ttcctcaaca agacctactc cagtgactcc                                        1350

<210> SEQ ID NO 94
<211> LENGTH: 1350
<212> TYPE: DNA
<213> ORGANISM: Duvenhage virus

<400> SEQUENCE: 94
atggatgctg aaagaattgt ctttaaggtc cgtaatcagc tagtctctgt aaaaccagag         60
gtcatctctg atcagtatga gtacaaatat cctgctatta ctgataagaa gaagcctagt        120
atcacacttg gaagggctcc ggacttgaag acagcataca agtccatctt gtcggggatg        180
aatgccgcca agctggatcc agatgacgta tgttcatact tagcaggtgc tatgattttg        240
tttgagggtg tgtgtcccga agattgggtt agttatggaa tccacattgc ccggaaaggc        300
gataaaataa cccctgctac gttagttgac atagttagaa caaatacaga gggtaactgg        360
gctcagacgg gaggtcagga tttaactaga gatccaacaa tctcagaaca tgcatcattg        420
gtaggacttt tactttgcct atataggtta agcaaaattg taggacagaa cacagggaat        480
tacaagacga atgtggctga ccggatggaa cagattttg aaactgctcc atttgtcaag         540
atagtcgagc accacacatt aatgaccact cacaaaatgt gtgcgaattg gagcacaata        600 cccaattta gatttcttgc aggaacatat gacatgttct tctccagggt ggatcatttg         660
tactcggcta ttagggttgg gacggtagtc actgcatatg aagattgttc aggtttagtc        720
tcctttactg ggtttatcaa gcagattaac ttgaccgcta gagaagccat attatacttc        780
tttcacaaga actttgagga ggagatcaaa agaatgtttg agcccggaca ggagactgct        840
gtgcctcact cctactttat ccactttaga tccttaggtc ttagcggcaa gtctccttac        900
tcctccaatg ctgtcggaca tgtgttcaac ttgatccatt ttgtaggttg ttacatgggt        960
caaatcagat cattaaacgc tacagttatc caaagttgtg ccccgcatga gatgtccgta       1020
```

| | |
|---|---|
| ttgggaggtt atttgggaga ggaattcttc ggaaagggga cctttgagag acgattcttt | 1080 |
| cgggacgaga aagagctgca agactatgaa gaagcagagg ccactaagat tgaggctgca | 1140 |
| ttggctgatg atggaactgt gaactccgac gatgaagact ttttctccgg agatacaaga | 1200 |
| agtccagaag ctgtttacac aaggatcatg atgaacggag gcggttaaa ggggggcacac | 1260 |
| ataagaaggt acgtctctgt aagttctagt caccaagcaa gaccaaactc ctttgcagag | 1320 |
| ttcctcaaca agacctactc cagtgactcc | 1350 |

<210> SEQ ID NO 95
<211> LENGTH: 1350
<212> TYPE: DNA
<213> ORGANISM: Duvenhage virus

<400> SEQUENCE: 95

| | |
|---|---|
| atggatgctg aaagaattgt cttaaggtc cgtaatcagc tagtctctgt aaaaccagag | 60 |
| gtcatctctg atcagtatga gtacaaatat cctgctatta ctgataagaa gaagcctagt | 120 |
| atcacacttg aagggctcc ggacttgaag acagcgtaca agtccatctt atcggggatg | 180 |
| aatgccgcca agctggatcc agatgacgta tgttcatact tagcaggtgc tatgattttg | 240 |
| tttgagggtg tgtgtcccga agattgggtt agttatggaa tccacattgc ccggaaaggc | 300 |
| gataaaataa cccctgctac gttagttgac atagttagaa caaatacaga aggtaactgg | 360 |
| gctcagacgg ggggtcagga tttaactaga gatccaacaa tctcagaaca tgcatcattg | 420 |
| gtaggacttt tactttgcct atataggtta agcaaaattg taggacagaa cacagggaat | 480 |
| tataagacga atgtggctga ccggatggaa cagatttttg aaactgctcc atttgtcaag | 540 |
| atagtcgagc accacacatt aatgaccact cacaaaatgt gtgcgaattg agcacaata | 600 |
| cccaattta gatttcttgc aggaacatat gacatgttct ctccagggt ggatcatttg | 660 |
| tactcggcta ttagggttgg gacggtagtt actgcatatg aagattgttc aggtttagtc | 720 |
| tcctttactg ggtttatcaa gcagattaac ttgaccgcta gagaagccat attatacttc | 780 |
| tttcacaaga actttgagga ggagatcaaa agaatgtttg agccggaca ggagactgct | 840 |
| gtgcctcact cctacttcat ccactttaga tccttaggtc ttagcggcaa gtctccttac | 900 |
| tcctccaatg ctgtcggaca tgtgttcaac ttgatccatt tcgtaggttg ttacatgggt | 960 |
| caaatcagat cattaaacgc tacagttatc caaagttgtg ccccgcatga gatgtccgta | 1020 |
| ttgggaggtt atttgggaga ggaattcttc ggaaagggga cctttgagag acgattcttt | 1080 |
| cgggacgaga aagagctgca agactatgaa gaagcagagg ccactaagat tgaggctgca | 1140 |
| ttggctgatg atggaactgt gaactccgac gatgaagact ttttctccgg agatacaaga | 1200 |
| agtccagaag ctgtttacac aaggatcatg atgaacggag gcgattaaa ggagcacac | 1260 |
| ataagaaggt acgtctctgt aagttctagt caccaagcaa gaccaaactc ctttgcagag | 1320 |
| ttcctcaaca agacctactc cagtgactcc | 1350 |

<210> SEQ ID NO 96
<211> LENGTH: 1350
<212> TYPE: DNA
<213> ORGANISM: Australian bat lyssavirus

<400> SEQUENCE: 96

| | |
|---|---|
| atggattctg ataagattgt cttaaggtc aacaatcagt tggtgtctgt taagccggag | 60 |
| gtgatagtag atcaatatga gtacaaatat cccgctatta aagaccaaaa gaagcctagt | 120 |

```
ataactcttg ggaaggctcc agatttaaat aaggcatata agtccatatt gtcgggaatg      180
aatgctgcaa agctggaccc cgatgatgta tgttcttact tagctgcagc tatggagtta      240
tttgaggggg tctgcccaga agattggacg agttatggga ttttgattgc cagaaaagga      300
gataaaatta caccagccac ccttgttgac ataaagagaa cagatattga gggcaactgg      360
gcattgacgg gaggacaaga cttgaccagg gatcccacag tagcagaaca cgcttcttta      420
gtaggtcttc ttctaagcct ttataggtta agcaagatat caggccagaa cacaggaaat      480
tataagacca acattgcaga caggatagaa cagattttg aaactgcccc ttttgcaaag       540
attgtggaac atcacacgtt aatgactact cataagatgt gtgcaaactg gagtacgatc      600
ccaaatttta gattttggc tggaacttat gacatgttct tttctcgagt tgagcacttg       660
tactctgcaa ttcgagtagg gacggtagta accgcttatg aagattgttc tggacttgtc      720
tcgtttacag ggtttatcaa acaaatcaac ctcactgcta gggaagcaat actgtatttc      780
ttccataaga acttcgaaga agaaattaga agaatgtttg aacccggaca agagactgca      840
gttcctcact cttatttcat ccatttcaga tctctaggac ttagcggaaa gtcccccttac     900
tcctccaatg cagttggcca tgtgttcaat ctcatccatt tcgtgggatg ttacatgggc      960
cagataagat ctttaaatgc gactgtcata tccacctgtg ctcctcatga gatgtctgtt     1020
ttgggaggct atcttgggga ggagtttttc gggaagggga cgtttgaacg gagattcttc     1080
agagatgaga aagaactgca agattatgag gcagcagagt ctatgaaaac agacattgct     1140
ttggcagatg atgcaaccgt caactcagat gatgaggatt acttttcagg agaaacaaga     1200
agtccagagg cagtttatac aagaataatg atgaatgggg gtcgacttaa aaggtcacac     1260
attaggagat acatctcagt cagctccaac catcagtccc gaccaaactc atttgcggag     1320
tttctcaaca agacatattc aagtgactcg                                      1350

<210> SEQ ID NO 97
<211> LENGTH: 1350
<212> TYPE: DNA
<213> ORGANISM: Australian bat lyssavirus

<400> SEQUENCE: 97
atggattctg ataagattgt ctttaaggtc aacaatcagt tggtgtctgt taagccggag       60
gtgatagtag atcaatatga gtacaaatat cccgctatta aagaccaaaa gaagcctagt      120
ataactcttg ggaaggctcc agatttaaat aaggcatata agtccatatt gtcgggaatg      180
aatgctgcaa agctggaccc cgatgatgta tgttcttact tagctgcagc tatggagtta      240
tttgaggggg tctgcccaga agattggacg agttatggga ttttgattgc cagaaaagga      300
gataaaatca caccagccac ccttgttgac ataaagagaa cagatattga gggtaactgg      360
gcattgacgg gaggacaaga cttgaccagg gatcccacag tagcagaaca cgcttcttta      420
gtaggtcttc ttctaagcct ttataggtta agcaagatat caggccagaa cacaggaaat      480
tataagacca acattgcaga taggatagaa cagattttg aaactgcccc ttttgcaaag       540
attgtggaac atcacacgtt aatgactact cataagatgt gtgcaaactg gagtacgatc      600
ccaaatttta gattttggc tggaacttat gacatgttct tttctcgggt tgagcacttg       660
tactctgcaa ttcgagtagg gacggtagta accgcttatg aagattgttc tggacttgtc      720
tcgtttacag ggtttatcaa acagatcaac ctcactgcta gggaagcaat actatatttc      780
ttccataaga acttcgaaga agaaattaga agaatgtttg aacccggaca agagactgca      840
gttcctcact cttatttcat ccatttcaga tctctaggac ttagcggaaa gtctccttac      900
```

```
tcctccaatg cagttggcca tgtgttcaat ctcatccatt tcgtgggatg ttacatgggc    960
cagataagat ctttaaatgc gactgtcata tccacctgtg ctcctcatga gatgtctgtt   1020
ttgggaggct atcttgggga ggagttttc gggaaggggga cgtttgaacg gagattcttc   1080
agagatgaga aagaactgca agattatgag gcagcgagt ctatgaaaac agacattgct   1140
ttggcagatg atgcaaccgt caactcagat gatgaggatt acttttcagg ggaaacaaga   1200
agtccagagg cagtttatac aagaataatg atgaatgggg gtcgacttaa aaggtcacac   1260
attaggagat acatctcagt cagctccaac catcagtccc gaccgaactc atttgcggag   1320
tttctcaaca agacatattc aagtgactcg                                    1350

<210> SEQ ID NO 98
<211> LENGTH: 1350
<212> TYPE: DNA
<213> ORGANISM: European bat lyssavirus-1

<400> SEQUENCE: 98
atggatgtta acaaggttgt ttttaaggtc cataatcagc tggtctcggt aagacctgag     60
gtgatttctg atcagtatga gtataagtac cctgctatta agacaagaa gaaaccaagc    120 atcactctcg gaaagatcc cgatttgaaa acagcctaca agtctatctt gtcagggatg    180
aatgctgcta aattagaccc agatgacgtc tgctcttatt tagctggagc catgatcttg    240
tttgagggca tctgcccgga agattggact agttacggaa tcaacattgc taagaaaggt    300
gacaagataa cacctgctac gttagtggac attcacagga cgaacactga ggcaactgg    360 gctcaaacag gaggtcaaga tctcactcgg gaccctacga cacctgaaca tgcatctctg    420
gttggacttc ttctctgtct ttataggctc agtaagatag taggacagaa tacggggaac    480
tataagacca atgtgcaga tagaatggaa cagatctttg agactgcccc attcgtcaag    540
attgtggaac accacacatt gatgaccacc cacaagatgt gtgccaactg gagcactata    600 cctaattta gattcttggc aggggcttat gacatgtttt ttgccagaat tgagcacctg    660
tattctgcaa ttcggggttgg gacagtggtt actgcttatg aggattgttc ggggttggtg    720 tcttcacag ggttcatcaa gcaaatcaat ttgacagcca gggaggccat attatacttc    780
ttccacaaga acttcgagga agagatcaag agaatgtttg agccagggca agaaacagct    840
gttccgcact cgtatttcat ccacttcaga tcacttggac tcagtgggaa gtctccttat    900
tcatccaatg cggttgggca tgtgtttaac ctgattcact ttgtgggttg ttacatgggc    960 caaatcgat ctttaaatgc cactgtcatt cagagttgtg cacccatgga aatgtcagtt   1020 ttgggggtt atctagggga ggagttttc gggaagggta catttgagag gcggttcttc   1080
agagatgaga aagagctaca ggattacgag gcagcagaaa gcactaaggt cgatgtagca   1140
ttggcagatg atgggacagt gaattcggat gatgaagact tcttttcggg agacacgaga   1200
agcccagagg cagtatacac caggattatg atgaacggag ggagattaaa aaggtctcac   1260
ataaagagat atgtctcagt gagtgcaaac catcaggcca ggcctaattc ctttgcagag   1320
tttctcaaca agacgtattc tagtgatccc                                    1350

<210> SEQ ID NO 99
<211> LENGTH: 1350
<212> TYPE: DNA
<213> ORGANISM: European bat lyssavirus-1
```

<400> SEQUENCE: 99

```
atggatgtta caaggttgt ttttaaggtc cataatcagc tggtctcggt aagacctgag      60
gtgatttctg atcagtatga gtataagtac cctgctatta agacaagaa gaaaccaagc     120
atcactctcg gaaagatcc cgatttgaaa acagcctaca agtctatctt gtcagggatg     180
aatgctgcta aattagaccc agatgacgtc tgctcttatt tagctggagc catggtcttg     240
tttgagggca tctgcccgga agattggact agttacggaa tcaacattgc taagaaaggt     300
gacaagataa cacctgctac gttagtggac attcacagga cgaacactga gggcaactgg     360
gctcaaacag gaggtcaaga tctcactcgg gaccctacga cacctgaaca tgcatctctg     420
gttggacttc ttctctgtct ttataggctc agtaagatag taggacagaa tacggggaac     480
tataagacca atgtggcaga tagaatggaa cagatgtttg agactgcctc accccccaag     540
attgtggaac accacacatt gatgaccacc cacaagatgt gtgccaactg gagcactata     600
cctaatttta gattcttggc aggggcttat gacatgtttt ttgccagaat tgagcacctg     660
tattctgcaa ttcgggttgg gacagtggtt actgcttatg aggattgttc ggggttggtg     720
tctttcacag ggttcatcaa gcaaatcaat ttgacagcca gggaggccat attatacttc     780
ttccacaaga acttcgagga gagatcaag agaatgtttg agccagggca agaaacagct     840
gttccgcact cgtatttcat ccacttcaga tcacttggac tcagtggaaa gtctccctat     900
tcatccaatg cggttgggca tgtgtttaac ctgattcact ttgtgggttg ttacatgggc     960
caaatcagat ctttaaatgc cactgtcatt cagagttgtg cacccatga aatgtcagtt    1020
ttgggggggtt atctagggga ggagttttc gggaagggaa catttgagag gcggttcttc    1080
agagatgaga aagagctaca ggattacgag gcagcagaaa gcactaaggt tgatgtagca    1140
ttggcagatg atgggacagt gaattcggat gatgaagact tcttttcggg agacacgaga    1200
agcccagagg cagtatacac caggattatg atgaacggag ggagattaaa aaggtctcac    1260
ataaagagat atgtctcagt gagtgcaaac catcaggcca ggcctaattc ctttgcagag    1320
tttctcaaca agacgtattc tagtgatccc                                    1350
```

<210> SEQ ID NO 100
<211> LENGTH: 1350
<212> TYPE: DNA
<213> ORGANISM: European bat lyssavirus-1

<400> SEQUENCE: 100

```
atggatgtta caaggttgt gtttaaggtc cataatcagc tggtctcagt aagacctgag      60
gtgatttctg atcagtatga gtataagtac cctgctatta agataagaa gaaaccaagc     120
atcactctcg gaaagatcc cgatttgaaa acagcctaca agtctatctt gtcagggatg     180
aatgctgcta aattagaccc agatgacgtc tgctcttatt tagctggagc catggtcttg     240
tttgagggca tctgcccgga agattggact agttacggaa tcaacattgc gaagaaaggt     300
gacaagataa cacctgctac gttagtggac attcacagga caaacactga gggcaactgg     360
gctcaaacag gaggtcaaga tctcactcgg gaccctacga cacctgaaca tgcatctctg     420
gttggacttc ttctttgtct ttataggctc agtaagatag taggacagaa tacggggaac     480
tataagacca atgtggcaga tagaatggaa cagatctttg agactgcccc atttgtcaag     540
attgtggaac accacacatt gatgaccacc cacaagatgt gtgccaactg gagcactata     600
cctaatttta gattcttggc aggggcttat gacatgtttt ttgccagaat tgagcacctg     660
```

```
tattctgcaa ttcgggttgg acagtggtt actgcttatg aggattgttc ggggttggtg      720
tctttcacag gattcatcaa gcaaataaat ttgacagcca gagaggccat attatacttc      780
ttccacaaga acttcgagga agagatcaag agaatgtttg agccagggca agaaacagct      840
gttccgcact cgtatttcat ccacttcaga tcacttggac tcagtgggaa gtctccttac      900
tcatccaatg cggttgggca tgtgtttaac ctgattcact ttgtgggttg ttacatgggt      960
caaatcagat ctttaaatgc cactgtcatt cagagttgtg cacccatga aatgtcagtt     1020
ttgggggggtt atctagggga ggagtttttc gggaagggga catttgaaag gcggttcttc     1080
agagatgaga aagagctaca ggattatgag gcagcagaaa gcactaaggt tgatgtagca     1140
ttggcagatg atgggacagt gaattcggat gatgaagatt tcttttcagg agacacgaga     1200
agcccagagg ctgtatacac caggattatg atgaacggag ggaggttaaa aaggtctcac     1260
ataaagagat atgtctcagt gagtgcaaat catcaggcca ggcctaattc ctttgcagag     1320
tttctcaaca agacgtattc tagtgacccc                                       1350

<210> SEQ ID NO 101
<211> LENGTH: 1350
<212> TYPE: DNA
<213> ORGANISM: European bat lyssavirus-2

<400> SEQUENCE: 101
atggatgctg acagaattgt cttcaaggtc cataatcagt tagtgtctgt aaagccagaa       60
gtaattgtag atcagtatga gtacaaatac cctgccatta agatcggaa aaaacccagc      120
ataacccttg gaaaagctcc agacttgaac agagcttata gtccattct gtccggaata      180
aatgctgcta ggttggatcc tgatgatgtg tgttcttacc tggctgcagc tatggctctg      240
tttgagggga tttgtcctga cgattgggag agctacggga ttctcattgc tagaaaaggg      300
gacaaaataa ccccgccaa tttagtcaat attcagagaa cagatgtaga aggcaattgg      360
gcactggcag ggggccaaga cgtaataaaa gatccgacca cagccgagca tgcatctttg      420
gtgggacttc tcctttgtct ttacagacta agcaaagtgt caggacagaa cacaggtaat      480
tacaagacta acgtggctga cagaatggaa caaatcttcg agacagcccc gtttgttaaa      540
attgtagagc atcatacttt tgatgactac cacaagatgt gcgccaactg gagtacaatt      600
cccaactta gattcttggc tgggacatat gacatgttct tctctagaat agagcatcta      660
tactctgcca ttcgagtcgg gacagtagtg actgcatatg aagattgttc agggctagtc      720
tctttcacgg ggttcatcag acagatcaac ttgacggcga aggaggccat actgtatttc      780
tttcataaga acttttgaaga agagatcaag agaatgttcg agccggggca agagacagct      840
atcccacact cttacttcat acacttcagg tcattgggac tgagtggaaa atctccttac      900
tcgtcgaatg cagtgggaca tgtattcaat ctcatccatt ttgtcgggag ttacatgggt      960
caagtcaggt cattgaatgc gacggtcatt gccacctgtg cacctcacga gatgtctgtg     1020
ttaggaggtt atctcgggga ggaattcttt ggcaaaggaa catttgagag aagattcttc     1080
agggacgaga gggaacttgc agagcatgag gcaatcgaat caactaagac cgatgtggcc     1140
ctggcagatg atgggacagt aaattcagac gatgaggagc tttactccgg agggacaaga     1200
accccgaag cggtgtacac caggatcatg gtcaatgggg gaaagctgaa aaaatcccac     1260
atcaaaagat atgtgtcagt cagctcgaat catcaggcca gacctaactc ctttgcagaa     1320
ttcttgaaca agacttattc gagtgatcca                                       1350
```

<210> SEQ ID NO 102
<211> LENGTH: 1350
<212> TYPE: DNA
<213> ORGANISM: European bat lyssavirus-2

<400> SEQUENCE: 102

```
atggatgctg acagaattgt cttcaaagtc cataatcagt tggtgtctgt aaagccagaa    60
gtaattgtag atcagtatga gtacaaatac cctgccatta agatcggaa aaaacccagc    120
ataacccttg aaaagctcc ggacctgaac agagcttata agtccattct gtccggaata    180
aatgctgcta ggttggatcc cgatgatgtg tgttcttatc tggctgcagc tatggctctg    240
tttgagggga tttgtcctga cgattgggag agctacggga ttctcattgc taggaaaggg    300
gacaaaataa ccccagccaa tttagtcaat attcagagaa cagatgtgga aggcaattgg    360
gcactggcag ggggccaaga cgtgataaaa gatccgacca cagccgagca tgcatctttg    420
gtgggacttc tcctttgtct ttacagacta agcaaagtgt caggacagaa cacagggaat    480
tacaagacca acgtagctga cagaatgaa caaatcttcg aaacagcccc gtttgtcaaa    540
attgtagagc atcacacttt tgatgactact cacaagatgt ggtctaattg gagtacaatt    600
cccaacttta gattcttggc tgggacatat gacatgtttt tctctagaat agagcatcta    660
tactctgcca ttcgagtcgg gacagtagtg actgcatacg aagattgttc agggctagtc    720
tctttcacag ggttcatcag acagatcaac ttgacggcga aggaggccat actgtatttc    780
tttcataaga actttgagga agagatcaag agaatgttcg agccgggggca ggagacagct    840
gtcccacatt cttacttcat acacttcagg tcattaggac tgagtggaaa atctccttac    900
tcgtcgaatg cagtaggaca tgtattcaac ctcattcatt ttgtcgggag ttacatgggt    960
caagtcaggt cattgaatgc gacagtcatt gccacctgtg cacctcacga gatgtccgtg    1020
ttgggaggtt atctcgggga ggaattcttt ggcaaggaa catttgaaag aaggttcttc    1080
agggacgaga gggaacttgc agagcatgag gcaatcgaat caaccaagac tgatgtggcc    1140
ctggcagatg atgggacctt aaattcagac gatgaggagt acttttccgg agggacaaga    1200
accccctgaag ctgtgtacac caggatcatg gtcaatgggg gaaaactaaa aaaatcccac    1260
atcaaaagat atgtgtcagt cagttcgaat catcaggcca gacctaactc ctttgcagaa    1320
ttcttgaaca agacttattc gagtgatcca                                    1350
```

<210> SEQ ID NO 103
<211> LENGTH: 1350
<212> TYPE: DNA
<213> ORGANISM: European bat lyssavirus-2

<400> SEQUENCE: 103

```
atggatgctg acagaattgt cttcaaagtc cataatcagt tggtgtctgt aaagccagaa    60
gtaattgtag atcaatatga gtacaaatac cctgccatta agatcggaa aaaacccagc    120
ataacccttg aaaaagctcc ggacttgaac agagcttata agtccattct gtccggaata    180
aatgccgcta ggttggatcc tgatgatgtg tgttcctatc tggctgcagc tatggctcta    240
tttgagggga tttgtcctga cgattgggag agctacggga ttctcattgc taggaaaggg    300
gacaaaataa ccccagccaa tttagtcaat attcagagaa cagatgtgga aggcaattgg    360
gcactggcag ggggccaaga cgtaataaaa gatccgacca cagccgagca tgcatctttg    420
gtgggacttc tcctttgtct ttacagacta agcaaggtgt caggacagaa cacagggaat    480
tacaagacca acgtagctga cagaatggaa caaatctttg agactgcccc gtttgtcaaa    540
```

```
attgtggagc atcacactttt gatgactact cacaagatgt gcgccaactg gagtacaatt      600
cccaacttta gatccttggc tgggacatat gacatgtttt tctctagaat agagcatcta      660
tactctgcca ttcgagtcgg gacagtagtg actgcatatg aagattgttc agggctagtc      720
tctttcacag ggttcatcag acagatcaac ttgacggcga aggaggccat actgtatttc      780
tttcataaga actttgagga agagatcaag agaatgttcg agccggggca ggagacagct      840
gtcccacatt cttacttcat acacttcagg tcattaggac tgagtggaaa atctccttac      900
tcgtcgaacg cagtaggaca tgtattcaac ctcattcatt ttgtcgggag ttacatgggt      960
caagtcaggt cattgaatgc gacggtcatt gccacctgtg cacctcacga gatgtccgtg     1020
ttgggaggtt atctcgggga ggaattcttt ggcaagggaa catttgaaag aagattcttc     1080
agggacgaga gggaacttgc agagcatgag gcaatcgaat caaccaagac tgatgtggcc     1140
ctggcagatg atgggaccgt aaattcagac gatgaggagc tttactccgg aggaacaaga     1200 accccctgaag ctgtgtacac caggatcatg gtcaatgggg gaaagctaca aaaatcccac     1260
atcaaaagat atgtgtcagt cagctcgaat catcaggcca gacctaactc ctttgcagaa     1320
ttcttgaaca agacttattc gagtgatcca                                     1350
```

<210> SEQ ID NO 104
<211> LENGTH: 1350
<212> TYPE: DNA
<213> ORGANISM: European bat lyssavirus-2

<400> SEQUENCE: 104

```
atggatgctg acagaattgt cttcaaagtc cataatcagt tggtgtctgt aaagccagaa       60
gtaattgtag atcagtatga gtacaaatac cctgccatta aagatcggaa aaaacccagc      120
ataacccttg aaaagctcc ggacctgaac agagcttata agtccattct gtccggaata      180
aatgctgcta ggttggatcc cgatgatgtg tgttcttatc tggctgcagc tatggctctg      240 tttgaggga tttgtcctga cgattgggag agctacggga ttctcattgc taggaaaggg      300
gacaaaataa ccccagccaa tttagtcaat attcagagaa cagatgtgga aggcaattgg      360
gcactggcag ggggccaaga cgtgataaaa gatccgacca cagccgagca tgcatctttg      420
gtgggacttc tcctttgtct ttacagacta agcaaagtgt caggacagaa cacagggaat      480
tacaagacca acgtagctga cagaatggaa caaatcttcg aaacagcccc gtttgtcaaa      540
attgtagagc atcacactttt gatgactact cacaagatgt gcgccaactg gagtacaatt      600
cccaacttta gattcttggc tgggacatat gacatgtttt tctctagaat agagcatcta      660
tactctgcca ttcgagtcgg gacagtagtg actgcatacg aagattgttc agggctagtc      720
tctttcacag ggttcatcag acagatcaac ttgacggcga aggaggccat actgtatttc      780
tttcataaga actttgagga agagatcaag agaatgttcg agccggggca ggagacagct      840
gtcccacatt cttacttcat acacttcagg tcattaggac tgagtggaaa atctccttac      900
tcgtcgaatg cagtaggaca tgtattcaac ctcattcatt ttgtcgggag ttacatgggt      960
caagtcaggt cattgaatgc gacagtcatt gccacctgtg cacctcacga gatgtccgtg     1020
ttgggaggtt atctcgggga ggaattcttt ggcaagggaa catttgaaag aaggttcttc     1080
agggacgaga gggaacttgc agagcatgag gcaatcgaat caaccaagac tgatgtggcc     1140
ctggcagatg atgggaccttt aaattcagac gatgaggagc tttactccgg agggacaaga     1200 accccctgaag ctgtgtacac caggatcatg gtcaatgggg gaaaactaaa aaaatcccac     1260
```

```
atcaaaagat atgtgtcagt cagttcgaat catcaggcca gacctaactc ctttgcagaa   1320
ttcttgaaca agacttattc gagtgatcca                                    1350

<210> SEQ ID NO 105
<211> LENGTH: 1350
<212> TYPE: DNA
<213> ORGANISM: Irkut virus-1

<400> SEQUENCE: 105
atggattctg acagaattgt cttcaaagtt cataaccagc tggtttctct taagccagag     60
gttatctctg atcagtatga atacaaatac cctgcgattg atgataaaaa gaaacccagt    120
attacactgg gaaaagcccc tgatttgaaa acagcatata agtcaatcct atcagggatg    180
aatgctgcca agcttgatcc tgatgatgtg tgctcttact tggctgcggc aatggtattt    240
tttgaaggaa tatgtcctga agattggact agctatggga taaacattgc caaaaaagga    300
gacaagataa cccctgcagt cctagttgat atacaaagga caaacacaga aggtaattgg    360
gctcaggcag gaggacaaga ccttactaga gatccaacaa caccggaaca tgcgtcttta    420
gtcgggctcc tcttgtgtct atacaggctg agcaagattg tgggacaaaa caccgggaat    480
tacaaaacca atgtggcgga gaggatggag cagatatttg agactgcacc gtttgtcaaa    540
attgtggaac atcacacctt gatgaccacc cataaaatgt gtgcaaattg gagcacaata    600
ccaaacttta gatttctggc aggggtttat gacatgttct tttcaagaat tgagcacctg    660
tattcagcaa ttcgtgtggg aacagttgtg actgcatatg aggactgctc tgggctggtg    720
tcatttacca catttatcag acagattaac ttgactgcta gggatgctgt tttgtacttc    780
tttcacaaga acttcgagga agagatcaag agaatgttcg agcctggtca agagactgct    840
gtcccccatt catatttcat tcattttagg tccttaggtc tgagtggcaa gtccccttac    900
tcgtctaatg cagtgggtca tacatttaat ctgatccact ttgtcgggtg ttatatgggt    960
caggtcagat cactcaatgc caccgtcata caaagctgtg ccccacacga gatgtctgtg   1020
ttaggaggat atctgggaga agagttcttt ggaaggggaa cctttgaaag acgattcttc   1080
agggatgaga aagaactgca ggactatgaa gccgccgagg caactaagat agatttggca   1140
ttggaggacg atggaaccgt gaactcagat gatgaagact tcttctcagg agagaccaga   1200
agccctgagg cagtttactc aaggatcatg atgagtgggg ggaggctcaa aaagtctcac   1260
atcaagaggt acatctcagt cagttcaaac catcaggcca gacctaattc atttgcggaa   1320
tttctcaata agacttatgc cagtgataca                                    1350

<210> SEQ ID NO 106
<211> LENGTH: 1350
<212> TYPE: DNA
<213> ORGANISM: Bokeloh bat lyssavirus

<400> SEQUENCE: 106
atggactctg acaagattgt cttcaaagtt cataatcagt tggtgtctgt aaagccagag     60
gtaattgttg atcaatatga gtacaaatat cctgctatca gagatcagaa gaaacctagc    120
ataactctgg ggaaagctcc tgatttaaac aaggcttaca aatctatatt gtcaggaata    180
aatgcggcta gattggatcc cgatgatgta tgttcctacc tagcggcagc tatggaactg    240
tttgaaggaa tttgccctga agattggcta agttatggga ttctcatagc aagaaagggg    300
gagaagatta cccctgccac cttggtgaac attcagagaa cgaacattga aggcaactgg    360
```

```
gccttgaccg gaggatacga ccttacaagg gatccaactg tggccgaaca tgcatctcta     420
gtgggccttc tgctctgctt gtatagactg agcaaggtct ccgggcagaa cacagggaat     480
tataagacta acatagccga tcgaatggag caaatctttg agaccgctcc ttttgtcaaa     540
atcgtggagc atcatacctt aatgaccact cacaaaatgt gtgccaattg gagtacaatc     600
ccaaatttta ggtttcttgc aggcacatat gatatgttct tttctaggat agagcattta     660
ttttctgcaa tccgagtcgg aactgtagtg acggcatatg aagattgttc tggactggtc     720
tctttcacag gattcatcaa acaaataaat ttgacggcta gggaagctat attgtatttc     780
ttccacaaga attttgaaga ggaaatcaag aggatgtttg aaccagggca agagactgca     840
gttccacact cttatttat acatttcagg tccttaggat tgagtgggaa gtctccttat      900
tcctcaaatg cagtaggtca tgtgtttaat ctgatccatt cgttggctg ttacatgggt      960 caaatcagat ctctaaatgc tactgttatc tctagttgtg caccacatga aatgtctgtg    1020
ttagggggtt atctggggga ggaattcttt ggcaagggaa cattcgagag gaggttcttc    1080
agagacgaaa aggagctccg ggattatgaa gccgtgagt ctgtcaaaaa cgacgttgca    1140
ctggcagatg acggaaccgt caactcagat gatgaggact tttttctgg ggaaacgaga    1200 agtccggagg ccgtgtatgc gaagatcatg atgaacgggg gaaaattgaa aaagtctcac    1260
atccggcgat atgtatcagt cagctcaaac caccaggcca gaccgaactc cttttgcagaa   1320 ttttttgaaca aaacttacct aggtgatcag                                    1350

<210> SEQ ID NO 107
<211> LENGTH: 1350
<212> TYPE: DNA
<213> ORGANISM: Mokola virus

<400> SEQUENCE: 107
atggagtctg acaagattgt gttcaaggtg aataaccaag ttgtttcttt gaagcctgag      60
gtcatatcag atcaatatga gtataaatat cccgccattc tagatgggaa gaaaccaggg     120
atcaccttgg ggaaggcacc tgatctaaac actgcataca aatccatcct atcaggtatg     180
aaggctgcaa agcttgaccc agacgatgtt tgctcttact tagcagctgc tatgcatcta     240
ttcgaggggg tctgtcccga ggactgggtt agttatggga ttgtcattgc gaagaaggga     300
gagaaaatca cccccagcgt gatcgtcgat atagttcgca ctaacgttga ggggaattgg     360
gctcaagcgg gaggaactga tgtgattaga gatcctacaa tggcagagca tgcttcattg     420
gtcggactgt tattatgtct gtatcgattg agcaagatag tcggtcagaa cacagcaaac     480
tataaaacca atgtagcaga cagaatggaa caaatatttg agactgctcc ttttgcgaag     540
gtggtggaac atcacacatt gatgactact cataagatgt gcgctaactg gagcactata     600
cctaacttca gattcctggt gggcacatat gatatgttct ttgcaagagt cgagcatata     660
tattcggctc tcagagtcgg aacagtcgtg acagcctacg aggattgctc aggcttggtc     720 tccttttaccg ggttttatcaa acaaatcaat ctatctccta gagatgcact gctatatttc     780
ttccataaaa actttgaagg ggagattaag agaatgtttg agccggggca agaaacagca     840
gttccccact catacttcat tcattttaga gcacttggcc tgagtggcaa gtccccgtac     900
tcgtccaatg ctgtaggtca tactttcaat ttaatccact tgtaggatg ctatatgggt     960 cagatcaggt ctctaaatgc aactgtgatc caaacatgtg cacctcacga gatgtcagta    1020 ctgggggat atcttggaga agagttcttt gggaaaggca ctttgagag gaggttcttt    1080 agggatgaaa aagagatgca agattataca gagcttgagg aggccagagt agaggcttcg    1140
```

| | |
|---|---|
| ctcgctgatg acgggactgt agactcagat gaggaggact tcttctctgg agaaaccaga | 1200 |
| agtcctgaag cagtttacag taggataatg atgaacaacg gtaaattgaa gaaagttcac | 1260 |
| atacgtaggt atattgcggt gagttctaat catcaagcga ggccgaactc ttttgcagaa | 1320 |
| ttcttaaaca aggtgtatgc agatggatca | 1350 |

<210> SEQ ID NO 108
<211> LENGTH: 1350
<212> TYPE: DNA
<213> ORGANISM: Mokola virus

<400> SEQUENCE: 108

| | |
|---|---|
| atggagtctg acaagattgt gttcaaggtg acaaccaag tcgtttcttt gaagcccgag | 60 |
| gtcatatcgg atcaatatga gtataaatat cctgccatcc tagatggaaa gaaaccaggg | 120 |
| ataactttag gaaaagcacc tgatctaagc accgcctaca agtccatctt atcaggtatg | 180 |
| aagtctgcaa agctcgaccc agacgatgtt tgttcttact ggcagctgc tatgcatctc | 240 |
| ttcgagggg tctgtcccga ggactgggtc agttatggga ttgtcattgc aaagaagggg | 300 |
| gagaagatta accctagtgt gatcgttgat ataacccgca caaatgttga gggaaattgg | 360 |
| gctcaagcgg aggaactga agtgatcaga gaccctacca cggcagagca tgcgtcattg | 420 |
| gttgggctgt tactgtgtct gtataggtta agcaagatag ttggccaaaa cactgcaaac | 480 |
| tataagacca atgtggctga cagaatggag caaatattcg aaacggctcc ttttgcgaag | 540 |
| gtggtagaac atcacacatt gatgactacc cacaagatgt gtgccaattg gagcactata | 600 |
| ccgaacttca gattcttggt aggtacatat gatatgttct ttgcaagagt tgagcacata | 660 |
| tattctgctc tcagagtcgg aacagtggtg actgcatatg aggattgctc tgggttggtc | 720 |
| tctttcaccg ggttcatcaa acagatcaat ctatctccta gggatgcgct gctatatttc | 780 |
| tttcataaaa actttgaggg agagatcaag agaatgtttg aaccaggca agagacagca | 840 |
| gtcccccatt catacttcat tcatttcagg gcactcggat tgagtggcaa gtccccatat | 900 |
| tcttccaatg ctgtgggtca tactttcaat ctaattcact tgttggatg ctatatgggt | 960 |
| cagatcaggt ctctcaatgc tacagtgatc caaacatgtg caccccacga aatgtcagtc | 1020 |
| ctaggaggat atctcggaga agagttcttt ggtaaaggca cattcgagag gaggtttttc | 1080 |
| agggatgaga agaaatgca agattataca gagttggagg gggccagagt ggaagcttca | 1140 |
| ctggctgatg atgggactgt ggactcagat gaggaagatt tcttctctgg agaaactaga | 1200 |
| agtcctgaag cagtctacag tcggataatg atgaataacg gcaagctaaa gaaagtccat | 1260 |
| atacgcaggt atatagcagt gagctctaat catcaagcca gaccgaactc ttttgccgaa | 1320 |
| ttcttgaaca aggtatatgc agatggttct | 1350 |

<210> SEQ ID NO 109
<211> LENGTH: 1350
<212> TYPE: DNA
<213> ORGANISM: Mokola virus

<400> SEQUENCE: 109

| | |
|---|---|
| atggagtctg acaagattgt gttcaaggtg aataaccaag ttgtttcttt gaagcctgag | 60 |
| gtcatatcag atcaatatga gtataaatat cccgccattc tagatgggaa gaaaccaggg | 120 |
| atcaccttgg ggaaggcacc tgatctaaac actgcataca aatccatcct atcaggtatg | 180 |
| aaggctgcaa agcttgaccc agacgatgtt tgctcttact tagcagctgc tatgcatcta | 240 |

| | |
|---|---:|
| ttcgaggggg tctgtcccga ggactgggtt agttatggga ttgtcattgc gaagaaggga | 300 |
| gagaaaatca accccagcgt gatcgtcgat atagttcgca ctaacgttga ggggaattgg | 360 |
| gctcaagcgg gaggaactga tgtgattaga gatcctacaa tggcagagca tgcttcattg | 420 |
| gtcggactgt tattatgtct gtatcgattg agcaagatag tcggtcagaa cacagcaaac | 480 |
| tataaaacca atgtagcaga cagaatggaa caaatatttg agactgctcc ttttgcgaag | 540 |
| gtggtggaac atcacacatt gatgactact cataagatgt gcgctaactg gagcactata | 600 |
| cctaacttca gattcctggt gggcacatat gatatgttct ttgcaagagt cgagcatata | 660 |
| tattcggctc tcagagtcgg aacagtcgtg acagcctacg aggattgctc aggcttggtc | 720 |
| tcctttaccg ggtttatcaa acaaatcaat ctatctccta gagatgcact gctatatttc | 780 |
| ttccataaaa actttgaagg agagattaag agaatgtttg agccggggca agaaacagca | 840 |
| gttccccact catacttcat tcattttaga gcacttggcc tgagtggcaa gtccccgtac | 900 |
| tcgtccaatg ctgtaggtca tactttcaat ttaatccact ttgtaggatg ctatatgggt | 960 |
| cagatcaggt ctctaaatgc aactgtgatc caaacatgtg cacctcacga gatgtcagta | 1020 |
| ctgggggat atcttggaga agagttcttt gggaaggca cctttgagag gaggttcttt | 1080 |
| agggatgaaa aagagatgca agattataca gagcttgagg aggccagagt agaggcttcg | 1140 |
| ctcgctgatg acgggactgt agactcagat gaggaggact tcttctctgg agaaaccaga | 1200 |
| agtcctgaag cagtctacag taggataatg atgaacaacg gtaaattgaa gaaagttcac | 1260 |
| atacgtaggt atattgcggt gagttctaat catcaagcga ggccgaactc ttttgcagaa | 1320 |
| ttcttaaaca aggtgtatgc agatggatca | 1350 |

<210> SEQ ID NO 110
<211> LENGTH: 1350
<212> TYPE: DNA
<213> ORGANISM: Mokola virus

<400> SEQUENCE: 110

| | |
|---|---:|
| atggagtctg ataagattgt attcaaggtg aacaaccaag ttgtttcttt gaagcctgag | 60 |
| gtcatatcag atcaatatga gtataaatat cctgccatct tagatgggaa gaaaccaggg | 120 |
| ataactttag ggaaggcacc agatctgaat actgcctata agtccatctt atcaggtatg | 180 |
| aaagccgcca agctcgaccc agaagatgtt tgctcttact tggcagctgc catgcatcta | 240 |
| ttcgaggggg tttgtcctga agactgggtc agttatggga ttgtcattgc aaagaaaggg | 300 |
| gagaaaatca accctagcgt gatcgttgac atagctcgaa ccaacgtgga ggggaattgg | 360 |
| gctcaagctg gaggaactga ggtaatcaga gaccctacaa ttgcagagca tgcatcattg | 420 |
| gttggactgt tgctgtgtct gtatcggttg agtaagatcg ttggccagaa cacagcaaac | 480 |
| tacaaaacta atgtagctga taggatggag caaatatttg agactgcccc ttttgcaaaa | 540 |
| gtggtggaac atcacacttt gatgactgcc cacaaaatgt gtgctaactg gagcactatc | 600 |
| cccaacttca gatttttggt tggtacatac gacatgtttt ttgcaagagt tgagcatata | 660 |
| tactcggctc tcagagtagg aacagtggta acagcatatg aggattgctc tgggttggtc | 720 |
| tccttcacag ggtttatcaa acagatcaat ctatccccta gagacgcact gctatatttc | 780 |
| tttcacaaaa actttgaggg agagatcaag agaatgtttg agccagggca agaaacagca | 840 |
| gtccccact catacttcat tcattttagg gcacttggat tgagtggcaa atctccttac | 900 |
| tcgtccaatg ctgtaggtca cactttcaat ctgattcatt ttgtgggatg ctatatgggt | 960 |
| cagatcaggt ctctaaatgc gacagttatc cagacctgtg cacctcatga gatgtcagtc | 1020 |

| | |
|---|---|
| ttaggggat atcttgggga agaattcttt gggaagggca ccttcgaaag gaggttcttc | 1080 |
| agagatgaaa aagaaatgca ggattataca gagctggagg gggcaagagt ggatgcctca | 1140 |
| cttgctgatg acgggactgt agactcagat gaggatgatt tcttttctgg agaaactaga | 1200 |
| agtcctgaag cagtctacag taggataatg atgaacggtg gtaagttgaa gaaagttcat | 1260 |
| atacgtagat atatagcggt gagctcaaac caccaagcga gaccaaactc ttttgcagaa | 1320 |
| ttcttgaata aagtatatgc agacggatca | 1350 |

<210> SEQ ID NO 111
<211> LENGTH: 1350
<212> TYPE: DNA
<213> ORGANISM: Mokola virus

<400> SEQUENCE: 111

| | |
|---|---|
| atggagtctg acaagattgt gttcagagtg aataatcaag ttgtttcttt gaaacccgaa | 60 |
| gtcatctcgg atcaatatga gtataaatat cctgccatct tagatggaaa gaaaccaggg | 120 |
| ataactttag ggaaggcccc tgacctgaac actgcataca agtccgtctt atcaggtatg | 180 |
| aaagctgcaa agctcgaccc agacgatgtt tgctcttact tggcagctgc tatgcatctc | 240 |
| ttcgagggag tctgccctga ggactgggtc agttatggga tcgtcattgc aaagaagggg | 300 |
| gagagaatca accctagcgt aattgttgat atagctcgca cgaatgttga agggaattgg | 360 |
| gctcaggccg aggaaccga tgtgatcaaa gaccccacaa ctgcagagca tgcatctttg | 420 |
| gtgggactgt tattgtgcct ttatcggttg agcaagatag ttggccagaa cacggcaaac | 480 |
| tataaaacta atgtggctga cagaatggag caaatattcg aaactgcccc ctttgctaaa | 540 |
| gttgtggaac atcacacatt gatgaccact cacaaaatgt gcgccaactg gagcactata | 600 |
| cccaacttca gattcctggt aggtacatat gatatgtttt ttgcaagagt tgagcacata | 660 |
| tattcggccc tcagagtcgg aacggtggtg acagcatatg aggactgctc tgggttggtc | 720 |
| tccttcaccg gattcctcaa acagattaat ttatctccta gagatgcact gttatatttc | 780 |
| tttcataaaa actttgaggg agagatcaag agaatgtttg agccaggca gaaacagcc | 840 |
| gttcctcatt catacttcat tcatttcaga gctctcggcc tgagtggtaa gtcccccttat | 900 |
| tcgtccaatg ctgtaggtca tacttttaat ctgattcact ttgtagggtg ttatatgggt | 960 |
| cagatcaggt ctttaaatgc aacggtgatt caaacatgtg cacctcatga gatgtcagtc | 1020 |
| ctaggaggat atcttgggga agaattcttt gggaagggca ccttcgagag gcggttcttc | 1080 |
| agggatgaaa aagaaatgca agattataca gagcttgagg gggctagagt ggaagcttca | 1140 |
| ctagccgatg acggtacggt agactcagat gaggaagact tcttctctgg ggaaaccaga | 1200 |
| agtcctgaag cggtttacag tcggataatg atgaatggtg gcaagttgaa gaaggttcat | 1260 |
| atacgccggt acatagcagt gagctctaat catcaggcta gacctaactc ttttgctgaa | 1320 |
| ttcttaaaca agtatatgc agatggatca | 1350 |

<210> SEQ ID NO 112
<211> LENGTH: 1350
<212> TYPE: DNA
<213> ORGANISM: Lagos bat virus

<400> SEQUENCE: 112

| | |
|---|---|
| atggattcgg aaaagattgt tttcaaggtg cataatcaag tagtgtcagt taaaccggaa | 60 |
| atcatctcag atcaatatga gtataaatat cctgcaatta cagatgggaa gaaacctggt | 120 |

| | |
|---|---|
| attacattgg aagggctcc agatttgagc actgcatata agtctatatt atctggaatg | 180 |
| aacgctgcta agctggaccc agatgatgta tgctcttatt tggctgccgc tatgcaactc | 240 |
| ttcgagggag tctgcccaga agattggatg agttatggga tccttatagc gaaaaaggga | 300 |
| gaaactatta ctcctgatgt cttgatagac ataactagaa cgaatgtgga aggaaactgg | 360 |
| gctcagacag aggggcaga tatgacgcga gatcctacag ttgctgaaca tgcctcttta | 420 |
| ataggacttc tcttgtgttt ataccgactg agtaaaatag tgggtcaaaa cacagctaat | 480 |
| tataagacca atgttgcaga caggatggag cagattttg aaactgctcc gtttgcaaaa | 540 |
| gtggttgaac atcacacatt gatgacaacc cacaaaatgt gcgcaaactg gagtacaatt | 600 |
| cctaatttca ggttttagc aggaacatat gatatgttct ttgctcgcat cgaacatctc | 660 |
| tattcggcta tcaggttgg tacagttgtg acagcttatg aagattgctc agggcttgta | 720 |
| tcttttacag ggtttattaa acaaattaac ttatctgcca gggatgcact attatacttc | 780 |
| ttccataaga gttttgaaga agagattaag aggatgtttg aacccggtca agaaacagca | 840 |
| gtcccccatt catacttcat ccactttcgg gcactagggt taagcgggaa atctccctac | 900 |
| tcctcaaatg cagtgggtca cacattcaac ctgatccatt ttattggatg ttatatgggt | 960 |
| caaataaggt ctctcaatgc tactgtaatt cagacttgtg ctcctcatga gatgtcggtt | 1020 |
| ttgggaggat atcttggtga agaattcttt ggaaggggga cctttgagag gaggttcttt | 1080 |
| agagatgaga aagagatgca agattatgcg gacttagagg gagcaagaat agaagcatct | 1140 |
| cttgcagatg atggcactgt tgactcagat gatgaagact ttttctctgg agagacaaga | 1200 |
| agtccagaag ctgtctacag caggattatg atgaacaatg gcaggttgaa gaaatctcac | 1260 |
| atccgcagat atgtctctgt aagttctaac catcaggcta ggccgaactc atttgcagaa | 1320 |
| tttctcaaca aggtgtattc ggagagctca | 1350 |

<210> SEQ ID NO 113
<211> LENGTH: 1350
<212> TYPE: DNA
<213> ORGANISM: Lagos bat virus

<400> SEQUENCE: 113

| | |
|---|---|
| atggattcag aaaagattgt tttcaaggtg cataatcaag tagtgtcagt taagccggaa | 60 |
| atcatctcag atcaatatga gtataaatat cctgcaatta cagatgggaa gaaacctggt | 120 |
| attacattgg aagggctcc agatttgagc actgcatata agtcaatatt gtctggaatg | 180 |
| aacgctgcta agctggaccc agatgatgta tgctccattt tggctgccgc tatgcatctc | 240 |
| ttcgaaggag tctgcccaga agattgggtg agttatggga tccttatagc gaaaaaggga | 300 |
| gaaactatta ctcctgatgt cttgatagac ataactagaa cgaatgtgga aggaaactgg | 360 |
| gctcagacgg aggggcaga catgacgcga gatcccacag ttgctgaaca tgcctcttta | 420 |
| gtaggacttc tcttgtgttt ataccgactg agtaaaatag tgggtcaaaa cacagctaat | 480 |
| tataagacca atgttgcaga caggatggag cagattttg aaactgctcc gtttgtaaaa | 540 |
| gtggttgaac atcacacatt gatgacaacc cacaaaatgt gtgcaaactg gagtacaatt | 600 |
| cctaatttca ggttttagc aggaacatat gatatgttct ttgctcgcat cgaacatctc | 660 |
| tattcggcca tcaggttgg tacagttgtg acagcttatg aagattgctc agggcttgta | 720 |
| tcttttacag ggtttattaa acaaattaac ttatctgcta gagatgcact attatacttc | 780 |
| ttccataaga gttttgaaga agagattaag aggatgtttg aacccggtca agaaacagca | 840 |
| gtcccccatt catacttcat acactttcgg gcactagggt taagcgggaa atctccctac | 900 |

```
tcctcaaatg cggtgggtca cacattcaac ctgatccatt ttattggatg ttatatgggt      960
caaataaggt ctctcaatgc tactgtaatt cagacttgtg ctcctcatga gatgtcggtt     1020
ttgggaggat atcttggtga agaattcttt ggaaggggga cctttgagag gaggttcttt     1080
agagatgaga aagagatgca agattatgcg gacttagagg gagcaagaat agaagcatct     1140
cttgcagatg atggcactgt tgactcagat gatgaagact ttttctctgg agagacaaga     1200
agtccagagg ctgtctacag caggattatg atgaacaatg caggttgaa gaaatctcac      1260 atccgcagat atgtctctgt aagttccaac catcaggcta ggccgaactc atttgcagaa     1320
ttcctcaaca aggtgtattc ggagagctca                                       1350
```

<210> SEQ ID NO 114
<211> LENGTH: 1350
<212> TYPE: DNA
<213> ORGANISM: Lagos bat virus

<400> SEQUENCE: 114

```
atggattcag aaaagattgt tttcaaggtg cataatcaag tagtgtcagt taaaccggaa       60
atcatctcag atcaatatga gtataaatat cctgcaatca cagatgggaa gaaacctggt      120
attacattgg aagggctcc agatttgagc actgcatata agtcaatatt gtctggaatg       180
aacgctgcta agctggaccc agatgatgta tgctcttatt tggctgcagc tatgcaactc     240
ttcgaaggtg tttgcccgga agattgggta agttacggga tccttatagc aaaaaaggga    300
gaaactatta cacctgatgt cttgatagac ataactagaa cgaatgtgga aggaaactgg    360
gcgcagacag gaggggcaga tatgacgcga gaccctacag tcgctgaaca tgcctctta     420 gtaggacttc tcctgtgttt gtatcgactg agtaaaatag tgggccaaaa cacagctaat     480
tataagacca atgttgcaga cagaatggag cagattttg agactgctcc gtttgtaaaa     540
gtggttgaac atcacacatt gatgacaacc cacaaaatgt gcgctaactg gagtacaatt     600
cctaatttca ggttttagc aggaacatat gatatgttct tgctcgcat cgaacatctc       660 tattcggcta tcaggttgg tacagttgta actgcttatg aagattgctc agggcttgta     720
tcttttacag ggtttattaa acaaattaac ttatctgcta gggatgcact gctatacttt     780
ttccataaga gttttgagga agagattaag agaatgtttg aacctggtca agaaacagct     840
gttccgcatt catacttcat acactttcgg gcactagggt taagcgggaa atctccctac     900
tcctcaaatg cagtgggtca tacattcaac ttgattcatt ttattggatg ttatatgggt     960
caaataaggt ctctcaatgc cacggtaatt cagacttgcg ctcctcatga gatgtcagtt     1020
ttaggaggat atcttggtga agaattcttc gggaagggaa cctttgagag gaggttcttt     1080
agagatgaga aagagatgca agattatgcg gatctagagg gagcaaggat agaagcatcc    1140
cttgcagatg acggtactgt tgattcagat gatgaagact ttttctctgg agagacaaga     1200
agtccagaag ctgtatacag caggattatg atgaacaatg cagattgaa gaaatctcac      1260 atccgcagat atgtctctgt aagttctaac catcaggcta gaccgaactc atttgcagaa    1320
tttcttaaca aggtgtattc ggagagctca                                       1350
```

<210> SEQ ID NO 115
<211> LENGTH: 1350
<212> TYPE: DNA
<213> ORGANISM: Lagos bat virus

<400> SEQUENCE: 115

```
atggattcgg aaaagattgt tttcaaggtg cataatcaag tagtgtcagt taaaccggaa     60
atcatcttag atcaatatga gtataaatat cctgcaatta cagatgggaa gaaacctggt    120
attacattgg gaagggctcc agatttgagc actgcatata agtctatatt atctggaatg    180
aacgctgcta agctggaccc agatgatgta tgctcttact tggctgccgc tatgcaactc    240
ttcgagggag tctgcccaga agattggatg agttatggga tccttatagc gaaaaaggga    300
gaaactatta ctcctgatgt cttaatagac ataactagaa cgaatgtgga aggaaactgg    360
gctcagacag gaggggcaga tatgacgcga gatcctacag ttgctgaaca tgcctcttta    420
ataggacttc tcttgtgttt ataccgactg agtaaaatag tgggtcaaaa cacagctaat    480
tataagacca atgttgcaga caggatggag cagattttg aaactgctcc gtttgcaaaa    540
gtggttgaac atcacacatt gatgacaacc cacaaaatgt gcgcaaactg gagtacaatt    600
cctaattca ggttttagc aggaacatat gatatgttct tgctcgcat cgaacatctc      660
tattcggcta tcagggttgg tacagttgtg acagcttatg aagattgctc agggcttgta    720
tcttttacag ggtttattaa acaaattaac ttatctgcca gggatgcact attatacttc    780
ttccataaga gttttgaaga agagattaag aggatgtttg aacccggtca agaaacagca    840
gtcccccatt catacttcat ccactttcgg gcactagggt taagcgggaa atctccctac    900
tcctcaaatg cagtgggtca cattcaac ctgatccatt ttattggatg ttatatgggt      960
caaataaggt ctctcaatgc tactgtaatt cagacttgtg ctcctcatga gatgtcggtt   1020
ttgggaggat atcttggtga agaattcttt ggaaagggga cctttgagag gaggttcttt   1080
agagatgaga aagagatgca agattatgcg gacttagagg gagcaagaat agaagcatct   1140
cttgcagatg atggtactgt tgactcagat gatgaagact ttttctctgg agagacaaga   1200
agtccagaag ctgtctacag caggattatg atgaacaatg gcaggttgaa gaaatctcac   1260
atccgcagat atgtctctgt aagttctaac catcaggcta ggccgaactc atttgcagaa   1320
tttctcaaca aggtgtattc ggagagctca                                    1350
```

<210> SEQ ID NO 116
<211> LENGTH: 1350
<212> TYPE: DNA
<213> ORGANISM: Shimoni bat virus

<400> SEQUENCE: 116

```
atggactctg aaaagattgt tttcaaagtt cgtaaccagg tggtgtcttt gaagccagaa     60
ataatctctg atcagtatga gtacaaatat cctgcaattc tggatggaag aaaaccgggg    120
atcactctag ggagagctcc agacttaaac acggcttaca aatcaatttt gtctggtatg    180
aatgctgcca aattggatcc agatgatgtg tgctcctatt ggctgctgc gatgcagctg     240
tttgaaggtg tttgcccaga ggattggact agttatggta ttgtgattgc aaagaagggt    300
gataagatca ctccggaaga tttgatagat gttactagga caaatgtaga gggaaattgg    360
gctcaaacag ggggaacaga catgacaaga gatccaacaa gtgcagaaca tgcatcttta    420
gtggggttgc tgttgtgctt atatcgtcta agcaagatag tcggccagaa tactgcaaat    480
tacaagacca atgttggccga taaatggaa caaattttg aaactgcacc ttttgtgaaa     540
attgttgaac atcatactct aatgactact cataaaatgt gtgctaattg gagtacaatt    600
ccaaactta gatttcttgc tggagcttat gatatgtatt ttgcaagaat agagcatctt    660
```

```
tactctgcta taagggttgg aactgtagtg actgcttacg aagattgttc aggattggtc      720
tccttcactg gatttataaa acaaattaat ttatctgcta gagatgcttt gctttatttc      780
tttcacaaaa attttgaaga agaaataaga agaatgttcg aacctggtca agaaactgca      840
attcctcatt cttacttcat acattttaga gctttgggat taagcggcaa atcaccctat      900
tcatcaaatg cagtaggtca taccttcaac ttgattcact ttataggttg ttatatgggt      960
cagataagat ctctaaatgc cacagttatt caagcttgtg cacctcatga gatgtctgtc     1020
ttgggaggtt atctaggaga ggaattcttt ggaaaaggta cttttgaaag aaggttcttc     1080
agggatgaaa aggagatgca agactatgca gaattggagg gaattaaaat agaggcagca     1140
ttggcagatg atggaacagt tgactctgat gatgaggatt tcttttcagg agagacaaga     1200
agtccagaag cagtgtatag tcgaatcatg atgaacaacg gcagattgaa aaggtcacac     1260
ataaggcggt acatatcagt cagctcaaat catcaggcaa ggcctaactc atttgcagag     1320 ttttttaaaca aggtgtactc agatgggtcc                                     1350

<210> SEQ ID NO 117
<211> LENGTH: 1350
<212> TYPE: DNA
<213> ORGANISM: West Caucasian bat virus

<400> SEQUENCE: 117
atggattctg aacacattgt gtttagggtc agaaatgaaa tagtgactct caaacccgaa       60
gtgatatccg accagtatga atataaatat cctgccatta cagataagaa aaaaccctcc      120
ataacactcg ggagggctcc cgatctgagc attgcctaca ggtcgattct gtcagggttc      180
aatgctgcta agttggatcc agatgatgtg tgctcctatc tagcagctgc tatgccattg      240
ttcgaagggg tttgcccaga ggattggatc agttacggga tcattatagc aaggaaggga      300
gacaagatta accctagtca cctggtagat ataatgagga cagaagtgga aggtaactgg      360
tctcaatctg gaggcgctga cgtgactaga aatcccaccg ttgctgagca tgcctcccctg      420 gtaggtctcc tcctctgcct gtatagattg agcaaaatag tgggccaaaa tacagccaac      480
tacaagacaa atgttgcaga caggatggaa caaatattcg aaacagcccc ttttgtcaaa      540
atcatagagc accacacact gatgacaact cacaagatgt gtgccaattg gagtaccatt      600
ccaaacttta gatttcttgt tggaacctat gacatgtttt tctcaagaat tgaccattta      660
tattctgctt tgagggtcgg cacagttgtc actgcatatg aagactgtac cgggcttgta      720
tcgttcactg cttttctcaa acagataaac ttgtcagcaa gagatgcaat cctatacttt      780
ttccataaga attttgaaga agaaatcagg agaatgttcc gtcccaatca ggagactgct      840 gttcccccact cttatttcat ccactttaga tctttgggtc ttagcgggaa gtctccatac      900
tcctccaatg cagtgggtca tgtgttcaac ttgattcact ttgtgggatg ctacatgggg      960
caagtaaggt ctctaaatgc gacagtcatt cagacatgtg ccccccacga aatgtctgtt     1020
ttgggaggtt atttggggga ggaattcttt ggaaaaggta cgtttgagag aagattcttt     1080
agagatgaaa gagagttgca ggatcatctt gaggcagaag aggccaagat agacattgct     1140
ctggcagatg acgccacagt agactccgga gatgaggatt tctacggcgg agagtcgagg     1200
agcccagagg cagtctataa tagaatcatc atgaacaagg ggagactcaa gaagttacac     1260
ataaagaggt atagatctgt gagctctaat catcaagccc gacccaatac ttttgcagag     1320
tttctaaata aggtttattc ggatgacaat                                      1350
```

```
<210> SEQ ID NO 118
<211> LENGTH: 1350
<212> TYPE: DNA
<213> ORGANISM: Ikoma virus

<400> SEQUENCE: 118
atggatcctg aacaagtagt tttcaagtct cggaaggaaa ttgtcgtgtt gagaccagag      60
gtgatatcgg atcagtatga atacaaatac cctgcgatag agaacaaaga gaagcctaca     120
ataactctac aaaaagcccc tgatctgaac atagcataca aatctgtttt gtcagcattc     180
aatactgccc gtctggacca ggaagatgtt tgttcatatt tagccgctgc aatgaggatt     240
tttgagggca actgtccaga ggattggata agctacggaa tcataatagc caagaaagga     300
gaaactatta accccggaca cctagtaaat ataaaacgga ctgagcaaga aggaaactgg     360
gcacaagttg caggagctgg tgtaattaaa gatcctactg atgctgagca tgcatcattg     420
gttggccttc tgttgtgctt gtataggtta agtaaaatag tgggtcaaaa cacagcaaat     480
tacaaaacta atgttgcaga ccggatgaaa caaattttg aaactgcacc atttgtgaag      540
attatagagc atcacacctt gatgactact cacaagatgt gtgcaaattg gagtacaatc     600
cctaatttca gattcttagc tgggacttac gatatgtttt tctctaggat agatcatctc     660
tatggagcta tcagagtagg aaccgttgta acagcttacg aagattgcac cggattggtt     720
tctttcacag gatttcttaa gcagataaat cttactgcag gagaagctat gctgtacttt     780
ttccacaaga acttcgagga agagtttaag agaatgttca agcctggtca agaaacggct     840 accctcact cctacttcgt gcatttcagg tctttaggac tgagtgggaa atctccttac       900
tcatctaatg cggttggtca catgtttaac ttgatacatt ttgtggggtg ctacatgggt     960
cagatcagat ctctaaatgc aactgtcatt cagacatgtg cacctcatga aatgtcggtt    1020
ttgggaggtt acttaggaga ggaattcttt gggaaggaa cattcgagag aagattcttt      1080
agaaacattg aagaaatgaa aacctatgaa gagttagaag aaagacgagt cgaggcagcg    1140
ctagaagacg acggcactgt tgattctggg gaagaagacg attggacagg ggagtctaga    1200
tccccagagg cggtgtttaa tcgcatcatg gtaaacaaag gaagattgcg tcctcatcac    1260
atcaagaggt ttagaaacgt cagtgcaaat catcaggcaa gaccgaattc ttttgcagaa    1320
ttcctttcta aagtatattc tgatacatca                                      1350
```